US011638751B2

(12) United States Patent
Baize et al.

(10) Patent No.: US 11,638,751 B2
(45) Date of Patent: *May 2, 2023

(54) IMMUNOGENIC COMPOSITION COMPRISING A RECOMBINANT ATTENUATED MOPEIA VIRUS WITH A MODIFIED NUCLEOPROTEIN DISPLAYING REDUCED EXONUCLEASE ACTIVITY

(71) Applicant: INSTITUT PASTEUR, Paris (FR)

(72) Inventors: Sylvain Baize, Lyons (FR); Audrey Page, Villeurbanne (FR); Xavier Carnec, Lyons (FR); Mathieu Jean Simon Mateo, Lyons (FR); Stephanie Reynard, La Mulatiere (FR); Alexandra Fizet, Les Echets (FR)

(73) Assignee: INSTITUT PASTEUR, Paris (FR)

( * ) Notice: Subject to any disclaimer, the term of this patent is extended or adjusted under 35 U.S.C. 154(b) by 68 days.

This patent is subject to a terminal disclaimer.

(21) Appl. No.: 17/106,928

(22) Filed: Nov. 30, 2020

(65) Prior Publication Data
US 2021/0205436 A1 Jul. 8, 2021

Related U.S. Application Data

(63) Continuation of application No. 15/770,210, filed as application No. PCT/EP2016/075573 on Oct. 24, 2016, now Pat. No. 10,849,969.

(60) Provisional application No. 62/245,631, filed on Oct. 23, 2015.

(51) Int. Cl.
| | |
|---|---|
| *A61K 39/12* | (2006.01) |
| *C12N 7/00* | (2006.01) |
| *C12N 9/16* | (2006.01) |
| *A61K 39/00* | (2006.01) |
| *C12N 9/22* | (2006.01) |

(52) U.S. Cl.
CPC ............... *A61K 39/12* (2013.01); *C12N 7/00* (2013.01); *C12N 9/16* (2013.01); *A61K 2039/5254* (2013.01); *C12N 9/22* (2013.01); *C12N 2760/10021* (2013.01); *C12N 2760/10022* (2013.01); *C12N 2760/10034* (2013.01); *C12N 2760/10041* (2013.01); *C12N 2760/10062* (2013.01)

(58) Field of Classification Search
CPC ............. A61K 39/12; C12N 7/00; C12N 2760/10062; C12N 2760/10041
See application file for complete search history.

(56) References Cited

PUBLICATIONS

Manning J. T., et al., Oct. 2015, Lassa virus isolates from Mali and the Ivory Coast represent an emerginig fifth lineage, Front. Microbiol. vol. 6, Article 1037, pp. 1-10.*

Fisher-Hoch, S. P., et al., Jan. 1989, Protection of rhesus monkeys from fatal Lassa fever by vaccination with a recombinant vaccinia virus containing the Lassa virus glycoprotein gene, Proc. Natl. Acad. Sci. USA 86:317-321.*
Carnec, X., et al., Nov. 2011, Lassa virus nucleoprotein mutants generated by reverse genetics induce a robust type I interferon response in human dendritic cells and macrophages, J. Virol. 85(22):12093-12097.*
Russier, M., et al., Dec. 2014, The exonuclease domain of Lassa virus is involved in antigen-presenting-cell mediated NK cell responses, J. Virol. 88(23):13811-13820.*
Schaeffer, J., et al., 2019, Non-pathogenic Mopeia virus induces more robust activation of plasmacytoid dendritic cells than Lassa virus, Viruses 11, 287; doi:10.3390/v11030287, pp. 1-9.*
Pannetier, D., et al., Aug. 2011, Human dendritic cells infected with the nonpathogenic Mopeia virus induce stronger T-cell responses than those infected with Lassa virus, J. Virol. 85(16):8293-8306.*
McCormick, J.B., et al., "A Prospective Study of the Epidemiology and Ecology of Lassa Fever" J. Infect. Dis. 155 (3):437-444 (1987).
Frame, J.D., et al., "Lassa Fever, a New Virus Disease of Man from West Africa I. Clinical Description and Pathological Findings" Am. J. Trop. Med. Hyg. 19(4):670-676 (1970).
Cummins, D. et al., "Acute Sensorineural Deafness in Lassa Fever" Jama 264(16):2093-2096 (1990).
Haas, W.H. et al., "Imported Lassa Fever in Germany: Surveillance and Management of Contact Persons" Clin. Infect. Dis. 36:1254-1258 (2003).
Briese, T. et al., "Genetic Detection and Characterization of Lujo Virus, a New Hemorrhagic Fever-Associated Arenavirus from Southern Africa" PLoS Pathogens 5(5), e1000455 (2009).
Parodi, A.S., et al., "Characteristics of Junin Virus. Etiological Agent of Argentine Hemorrhagic Fever" Arch. Gesamte. Virusforsch 19:393-402 (1966).
Delgado, S. et al. "Chapare Virus, a Newly Discovered Arenavirus Isolated from a Fatal Hemorrhagic Fever Case in Bolivia" PLoS Pathogens 4(4), e1000047 (2008).
Webb, P.A., et al., "Some Characteristics of Machupo Virus, Causative Agent of Bolivian Hemorrhagic Fever" Am. J. Trop. Med. Hyg. 16(4):531-538 (1967).
Lisieux, T. et al., "New Arenavirus Isolated in Brazil", Lancet 343(8894):391-392 (1994).
Salas, .R et al., "Venezuelan Haemorrhagic Fever" Lancet 338:1033-1036 (1991).
Milazzo, M.L., et al., "Novel Arenavirus Infection in Humans, United States" Emerg. Infect. Dis. 17(8):1417-20 (2011).
McKee, K.T., et al., "Candid No. 1 Argentine Hemorrhagic Fever Vaccine Protects Against Lethal Junin Virus Challenge in Rhesus Macaques" Intervirology 34:154-163 (1992).
Fisher-Hoch, S.P. et al., "Protection of Rhesus Monkeys from Fatal Lassa Fever by Vaccination with a Recombinant Vaccinia Virus Containing the Lassa Virus Glycoprotein Gene" Proc. Natl. Acad. Sci. U.S.A. 86:317-321 (1989).

(Continued)

*Primary Examiner* — Jeffrey S Parkin
(74) *Attorney, Agent, or Firm* — Arrigo, Lee, Guttman & Mouta-Bellum LLP

(57) ABSTRACT

A recombinant attenuated Mopeia virus (MOPV) comprising a recombinant genomic S segment that encodes a nucleoprotein having attenuated exonuclease activity, and optionally further encodes a non-MOPV arenavirus glycoprotein. Use of the recombinant attenuated MOPV to induce an immune response in a subject.

19 Claims, 17 Drawing Sheets

Specification includes a Sequence Listing.

(56) References Cited

PUBLICATIONS

Carnec, X. et al., "Lassa Virus Nucleoprotein Mutants Generated by Reverse Genetics Induce a Robust Type I Interferon Response in Human Dendritic Cells and Macrophages", J. Virol. 85(22):12093-12097, (2011).

Hastie, K.M., et al., "Structure of the Lassa Virus Nucleoprotein Reveals a dsRNA-Specific 3' to 5' Exonuclease Activity Essential for Immune Suppression", Proc. Natl. Acad. Sci. U.S.A. 108(6):2396-2401 (2011).

Qi, X. et al., "Cap Binding and Immune Evasion Revealed by Lassa Nucleoprotein Structure" Nature 468 (7325):779-783 (2010).

La Posta, V.J., et al., "Cross-Protection Against Lymphocytic Choriomeningitis Virus Mediated by a CD4+ T-cell Clone Specific for an Envelope Glycoprotein Epitope of Lassa Virus", J. Virol. 67(6):3497-506 (1993).

Jiang, X. et al., "Yellow Fever 17D-Vectored Vaccines Expressing Lassa Virus GP1 and GP2 Glycoproteins Provide Protection Against Fatal Disease in Guinea Pigs", Vaccine 29:1248-1257 (2011).

Fisher-Hoch, S.P., et al., "Effective Vaccine for Lassa Fever" J. Virol. 74(15):6777-6783 (2000).

Kerber, R. et al., "Cross-Species Analysis of the Replication Complex of Old World Arenaviruses Reveals Two Nucleoprotein Sites Involved in L Protein Function" J. Virol. 85(23):12518-12528 (2011).

Auperin, D.D. et al., "Nucleotide Sequence of the Lassa Virus (Josiah Strain) S Genome RNA and Amino Acid Sequence Comparison of the N and GPC Proteins to Other Arenaviruses" Virology 168:421-425 (1989).

Raju, R. et al., "Nontemplated Bases at the 5' Ends of Tacaribe Virus mRNAs" Virology 174:53-59 (1990).

Baize, S. et al., "Role of Interferons in the Control of Lassa Virus Replication in Human Dendritic Cells and Macrophages", Microbes Infect 8:1194-1202 (2006).

Wilson, E.B et al., "Blockade of Chronic Type I Interferon Signaling to Control Persistent LCMV Infection" Science 340 (6129):202-207 (2013).

Lange, J.V. et al., "Kinetic Study of Platelets and Fibrinogen in Lassa Virus-Infected Monkeys and Early Pathologic Events in Mopeia Virus-Infected Monkeys" Am. J. Trap. Med. Hyg. 34(5):999-1007 (1985).

Baize, S et al., "Lassa .Virus Infection of Human Dendritic Cells and Macrophages is Productive but Fails to Activate Cells", J. Immunol. 172(5):2861-2869 (2004).

Pannetier, D. et al., "Human Macrophages, but not Dendritic Cells, Are Activated and Produce Alpha/Beta Interferons in Response to Mopeia Virus Infection" J. Virol. 78(19): 10516-10524 (2004).

Reynard et al., "Exonuclease Domain of the Lassa Virus Nudeoprotein Is Critical To Avoid RIG-I Signaling and To Inhibit the Innate Immune Response", Journal of Virology, 88(23) 13923-13927 (2014).

Martinez-Sobrido et al., "Identification of Amino Acid Residues Critical for the Anti-Interferon Activity of the Nucleoprotein of the Prototypic Arenavirus Lymphocytic Choriomeningitis Virus", Journal of Virology 83 (21):11330-11340 (2009).

Carrion et al., "Vaccine Platforms to Control Arenaviral Hemorrhagic Fevers", Journal of Vaccines & Vaccination 3 (7):1-22(2012).

Lukashevich et al., "Advanced Vaccine Candidates for Lassa Fever", Viruses 4:2514-2557 (2012).

Lukashevich et al., "A Live Attenuated Vaccine for Lassa Fever Made by Reassortment of Lassa and Mopeia Viruses", Journal of Virology 79(22): 13934-13942 (2005).

Kiley, M. P., et al., "Protection of Rhesus Monkeys From Lassa Virus by Immunisation With Closely Related Arenavirus," The Lancet, Oct. 6, 1979, p. 738.

Carnec X, Mateo M, Page A, Reynard S, Hortion J, Picard C, Yekwa E, Barrot L, Barron S, Vallve A, Raoul H, Carbonnelle C, Ferron F, Baize S. 2018. A vaccine platform against arenaviruses based on a recombinant hyperattenuated Mopeia virus expressing heterologous glycoproteins. J Virol 92:e02230-17. https://doi.org/10.1128/JVI.02230-17.

Natasha Kushnir, et al., "Virus-like particles as a highly efficient vaccine platform: Diversity of targets and production systems and advances in clinical development," Vaccine 31 (2012) 58-83.

Ulery BD, Kumar D, Ramer-Tait AE, Metzger DW, Wannemuehler MJ, et al. (2011) Design of a Protective Single-Dose Intranasal Nanoparticle-Based Vaccine Platform for Respiratory Infectious Diseases. PLoS ONE 6(3): e17642. doi:10.1371/journal.pone.0017642.

\* cited by examiner

FIG. 1A

MOPV_NP Protein

DEDDH domain
→ Exonucleasic function
PNAKTWIDIEGRPED

N-term ▬▬▬▬▬▬▬▬▬▬▬▬▬▬▬▬ C-term

Substitutions: D390A/G393A → Loss of exonucleasic function
*Other positions currently being screened : E392 – H430 – D467 – H529 – D534*

FIG. 1B Modifications of MOPV_Small segment 1. 5' ──GPC──▶ ⌒ ◀──NP── 3'
2. 5' ──LASV-GPC──▶ ⌒ ◀──NP── 3'
3. 5' ──LASV-GPC──▶ ⌒ ◀──NP── 3'

FIG. 1C

Obtention of MOPV-ExoN, MOPV-GP$_{LASV}$ and enhanced viruses

Pol I promoter — pPOLI_Sag (MOPV_S) — Pol I terminator

Reverse Genetic in BHK-T7/9 cells

Rescue of
MOPV-ExoN
MOPV-ExoN-GP$_{LASV}$
MOPV-ExoN$_{enhanced}$
MOPV-ExoN$_{enhanced}$-GP$_{LASV}$
MOPV-ExoNM6b
MOPV-ExoNM6b-GPC

*Graph 1 (top): titer (ffu/ml) vs days post infection (0–4), showing natMOPV, recMOPV, and MOPV-ExoN*

*Graph 2 (bottom): titer (ffu/ml) vs days post infection (0–4), showing natMOPV, recMOPV, and MOPV-ExoN*

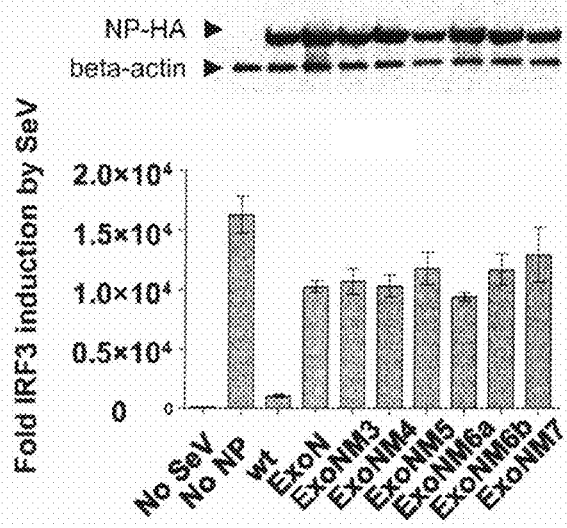

IFNα1

IFNα2

IFNβ

☐ Mock
■ MOPV-wt
▨ MOPV-ExoNM6b
☰ MOPV-ExoNM6b-GPC$_{LASV}$
▦ MOPV-ExoNM6b-GPC$_{MACV}$

Figure 9

Simplified presentation of the Mopeia reverse genetic system

IMMUNOGENIC COMPOSITION COMPRISING A RECOMBINANT ATTENUATED MOPEIA VIRUS WITH A MODIFIED NUCLEOPROTEIN DISPLAYING REDUCED EXONUCLEASE ACTIVITY

SEQUENCE LISTING

The instant application contains a Sequence Listing which has been submitted electronically in ASCII format and is hereby incorporated by reference in its entirety. Said ASCII copy, created on Apr. 22, 2018, is named 373946_D36598_CMB_SL.txt and is 84,079 bytes in size.

INTRODUCTION

Mopeia virus (MOPV) is an old-world arenavirus, phylogenetically closely related to Lassa (LASV). MOPV was first isolated in Mastomys rodent in Mozambique, whereas LASV is endemic in West Africa. On the contrary to LASV, MOPV infection was never observed in human and experimental infection of monkeys with MOPV is asymptomatic. LASV, the etiological agent of Lassa Fever (LF), infects 100,000 to 300,000 persons each year, killing about 5,000 of them[1]. The virus is naturally present in Mastomys rodents and human contamination occurs through direct contact with rodents or their dejections. After a relatively short incubation period, the onset of the disease starts with flu-like symptoms, such as fever, myalgia, headaches. In the severe forms, haemorrhages and oedema are then observed[2]. In the late stages, death of patients occurs in a hypovolemic, hypotensive and hypoxic shock context. For those who survive, severe complications have been reported, such as persistent myalgia and deafness[3]. To date, no licensed vaccine or efficient treatment is available for use on the field. Moreover, the virus is also sometimes exported to industrial countries[4]

Other arenaviruses are also responsible for severe hemorrhagic fevers, with a similar clinical picture: Lujo virus[5] (belonging to the old world arenavirus Clade), Junin[6], Chapare[7], Machupo[8], Sabia[9], Guanarito[10] and Whitewater Arroyo[11] (all belonging to the New World Clade). New arenaviruses are frequently isolated, either in humans or in rodents, and the area affected by these viruses are expanding, demonstrating the dynamism of this viral family and the threat they represent for public health.

To date, no treatment is available to fight against those deadly agents. The only FDA-approved vaccine available is the Candid #1 vaccine[12], a natural attenuated strain of Junin virus, which is able to protect humans against this virus. Thus, the development of a vaccine strategy directed against arenavirus-induced diseases is an important challenge and probably represents the most valuable approach to cope with this threat.

Experimental vaccination of non-human primates (NHP) with MOPV protected them against an experimental challenge with LASV, shedding light on the protective potential of MOPV against LASV. However, the administration of such a natural virus in humans is not feasible, due to the lack of full knowledge regarding its safety in human and more particularly in immunocompromised people, elderly people and pregnant women. Moreover, administration of a live, natural virus as a vaccine raises ethical concerns and for a variety of reasons is not feasible.

Accordingly, there is a need in the art for a vaccine platform and vaccines against pathogenic arenaviruses, including against LASV, for use as a vaccine and/or therapeutic against arenaviruses responsible for hemorrhagic fevers and other conditions in humans. The inventions disclosed and provided herein meet these and other needs.

SUMMARY

The inventors have made the discovery that the nucleoprotein (NP) of MOPV has an exonuclease function similar to that of LASV. In LASV, the exonuclease function plays a role in pathogenicity because it digests double-stranded RNA (dsRNA), which is an important Pathogen Associated Molecular Pattern (PAMPs) which is expected to be recognized by the innate immune system to fight against infection. Because LASV NP is able to digest these dsRNA, their recognition by the immune system and subsequent IFN activation is thus avoided[14], leading to relentless virus replication and dissemination. It is surprising that the NP of MOPV also exhibits this exonuclease function because the MOPV is non pathogenic. As described in the examples, the inventors have generated a recombinant MOPV, in which the exonuclease function has been abrogated (MOPV-ExoN). The examples characterize this virus for its replicative properties and immunogenicity, and identified that this virus is poorly replicative in immune cells, able to strongly activate dendritic cells (DC) and macrophages (MP), and is much more immunogenic than its wild type counterpart. Based in part on this data, this invention provides a new vaccine platform against pathogenic arenaviruses.

The examples describe making of exemplary recombinant attenuated MOPV comprising an NP having attenuated exonuclease activity and optionally a heterologous glycoprotein (GP), notably a heterologous glycoprotein precursor (GPC) from a pathogenic arenavirus (e.g., Lasso). As demonstrated in the examples, the recombinant attenuated MOPV exhibit several desirable properties demonstrating that recombinant attenuated MOPVs of the invention are particularly useful as agents for inducing immunogenic responses in a subject against an arenavirus, such as for immunizing against or treating an arenavirus infection.

Accordingly, this invention provides recombinant attenuated Mopeia virus (MOPV). In some embodiments, the recombinant attenuated MOPV comprises a heterologous nucleic acid and a nucleic acid encoding a nucleoprotein having attenuated exonuclease activity. The recombinant attenuated MOPV are useful, for example, to induce an immunogenic response against an arenavirus in a subject.

In some embodiments of the recombinant attenuated MOPV, the nucleoprotein comprises an amino acid substitution at amino acid position D390 or G393. In some embodiments of the recombinant attenuated MOPV, the nucleoprotein comprises amino acid substitutions at amino acid positions D390 and G393.

In some embodiments of the recombinant attenuated MOPV, the nucleoprotein comprises amino acid substitution at amino acid position D390 or G393, and further comprises at least one amino acid substitution at a position selected from E392, H430, D467, H529, and D534. In some embodiments of the recombinant attenuated MOPV, the nucleoprotein comprises amino acid substitutions at amino acid positions D390 or G393, and further comprises amino acid substitution at position E392. In some embodiments of the recombinant attenuated MOPV, the nucleoprotein comprises amino acid substitutions at amino acid positions D390 or G393, and further comprises amino acid substitutions at positions E392 and H430. In some embodiments of the recombinant attenuated MOPV, the nucleoprotein comprises amino acid substitutions at amino acid positions D390 or G393, and further comprises amino acid substitutions at positions E392, H430 and D467. In some embodiments of the recombinant attenuated MOPV, the nucleoprotein comprises amino acid substitutions at amino acid positions 0390 or G393, and further comprises amino acid substitutions at positions E392, H430, D467 and H529. In some embodiments of the recombinant attenuated MOPV, the nucleoprotein comprises amino acid substitutions at amino acid positions D390 or G393, and further comprises amino acid substitutions at positions E392, H430, D467 and D534. In some embodiments of the recombinant attenuated MOPV, the nucleoprotein comprises amino acid substitutions at amino acid positions D390 or G393, and further comprises amino acid substitutions at positions E392, H430, D467, H529 and D534. In some embodiments of the recombinant attenuated MOPV, the nucleoprotein comprises amino acid substitutions at amino acid positions D390 and G393, and further comprises at least one amino acid substitution at a position selected from E392, H430, 0467, H529, and D534. In some embodiments of the recombinant attenuated MOPV, the nucleoprotein comprises amino acid substitutions at amino acid positions D390 and G393, and further comprises amino acid substitutions at position E392. In some embodiments of the recombinant attenuated MOPV, the nucleoprotein comprises amino acid substitutions at amino acid positions D390 and G393, and further comprises amino acid substitutions at positions E392 and H430. In some embodiments of the recombinant attenuated MOPV, the nucleoprotein comprises amino acid substitutions at amino acid positions 0390 and G393, and further comprises amino acid substitutions at positions E392, H430 and D467. In some embodiments of the recombinant attenuated MOPV, the nucleoprotein comprises amino acid substitutions at amino acid positions D390 and G393, and further comprises amino acid substitutions at positions E392, H430, D467 and H529. In some embodiments of the recombinant attenuated MOPV, the nucleoprotein comprises amino acid substitutions at amino acid positions D390 and G393, and further comprises amino acid substitutions at positions E392, H430, D467 and 0534 (designated MOPV-ExoNM6b). In some embodiments of the recombinant attenuated MOPV, the nucleoprotein comprises amino acid substitutions at amino acid positions D390 and G393, and further comprises amino acid substitutions at positions E392, H430, D467, H529 and 0534.

In some embodiments of the recombinant attenuated MOPV, the nucleoprotein comprises a D390A or a G393A amino acid substitution. In some embodiments of the recombinant attenuated MOPV, the nucleoprotein comprises the D390A and G393A amino acid substitutions. In some embodiments of the recombinant attenuated MOPV, the nucleoprotein further comprises at least one amino acid substitution selected from E392A, H430A, D467A, H529A, and D534A. In some embodiments of the recombinant attenuated MOPV, the nucleoprotein further comprises amino acid substitutions at position E392A (designated MOPV-ExoNM3). In some embodiments of the recombinant attenuated MOPV, the nucleoprotein further comprises amino acid substitutions at positions E392A and H430A (designated MOPV-ExoNM4). In some embodiments of the recombinant attenuated MOPV, the nucleoprotein further comprises amino acid substitutions at positions E392A, H430A and D467A (designated MOPV-ExoNM5). In some embodiments of the recombinant attenuated MOPV, the nucleoprotein further comprises amino acid substitutions at positions E392A, H430A, D467A and H529A (designated MOPV-ExoNM6a). In some embodiments of the recombinant attenuated MOPV, the nucleoprotein further comprises amino acid substitutions at positions E392A, H430A, D467A and D534A (designated MOPV-ExoNM6b). In some embodiments of the recombinant attenuated MOPV, the nucleoprotein further comprises amino acid substitutions at positions E392A, H430A, D467A, H529A and D534A (designated MOPV-ExoNM7).

In some embodiments of the recombinant attenuated MOPV, the heterologous nucleic acid encodes a non-MOPV arenavirus glycoprotein (GP), notably a non-MOPV arenavirus glycoprotein precursor (GPC). In some embodiments of the recombinant attenuated MOPV, the non-MOPV arenavirus is a Lasso virus (LASV).

In some embodiments, the recombinant attenuated MOPV is poorly replicative in immune cells, strongly activates at Least one of dendritic cells (DC) and macrophages (MP), and/or is more immunogenic than unmodified MOPV. In some embodiments, the recombinant attenuated MOPV is poorly replicative in immune cells. In some embodiments, the recombinant attenuated MOPV is strongly activates at least one of dendritic cells (DC) and macrophages (MP). In some embodiments, the recombinant attenuated MOPV is more immunogenic than unmodified MOPV.

In some embodiments, the recombinant attenuated MOPV is poorly replicative in immune cells and strongly activates at least one of dendritic cells (DC) and macrophages (MP).

In some embodiments, the recombinant attenuated MOPV strongly activates at least one of dendritic cells (DC) and macrophages (MP), and is more immunogenic than unmodified MOPV.

In some embodiments, the recombinant attenuated MOPV is poorly replicative in immune cells and is more immunogenic than unmodified MOPV.

The invention also provides immunogenic compositions that comprise at least one of the recombinant attenuated MOPVs disclosed herein.

The invention also provides methods of inducing an immune response against an arenavirus in a subject. In some embodiments, the method is a method of inducing a protective immune response against an arenavirus in a subject at risk of infection with the arenavirus. Such methods may comprise administering an effective amount of an arenavirus of the invention, such as in the form of an immunogenic composition comprising an arenavirus of the invention, to the subject.

In some embodiments, the method is a method of inducing a therapeutic immune response against an arenavirus in a subject Infected with the arenavirus. Such methods may comprise administering an effective amount of an arenavirus of the invention, such as in the form of an immunogenic composition comprising an arenavirus of the invention, to a subject infected with the arenavirus.

The invention also provides a eukaryotic cell comprising a recombinant MOPV of the invention.

BRIEF DESCRIPTION OF THE DRAWINGS

FIGS. 1A to IC show rational design used herein to make the disclosed anti-LASV vaccine prototype. (A) Identification of critical residues in NP protein which are important for abrogation of MOPV NP exonuclease function, localisation of the DEDDH domain. SEQ ID NO. 6: PNAKTWIDIEGRPED (B) Genetic manipulation of the MOPV Short segment. 1. Site-directed mutagenesis was used to introduce D390A/6393A (and others) toss of function mutations in NP open-reading frame. 2. Swapping of GPc gene in MOPV short genomic segment. 3. Combination of both approaches resulting in MOPV-ExoN-GP$_{LASV}$. (C)

Reverse genetics strategy for the obtention of the mutated recombinant viruses. The engineered pPOLI-MOPV-Sag was transfected together with PTM1-LPol, PTM1-NP, pPOL1-MOPV-Lag in T7 polymerase harboring cells, leading to production of rec-MOPV, MOPV-ExoN, MOPV-ExoN$_{enhanced}$, MOPV-ExoNM6b, MOPV-GP$_{LASV}$, MOPV-ExoN-GP$_{LASV}$, MOPV-ExoN$_{enhanced}$-GP$_{LASV}$ and MOPV-ExoNM6b-GPC viruses expressing other GPCs.

Figure 2A:
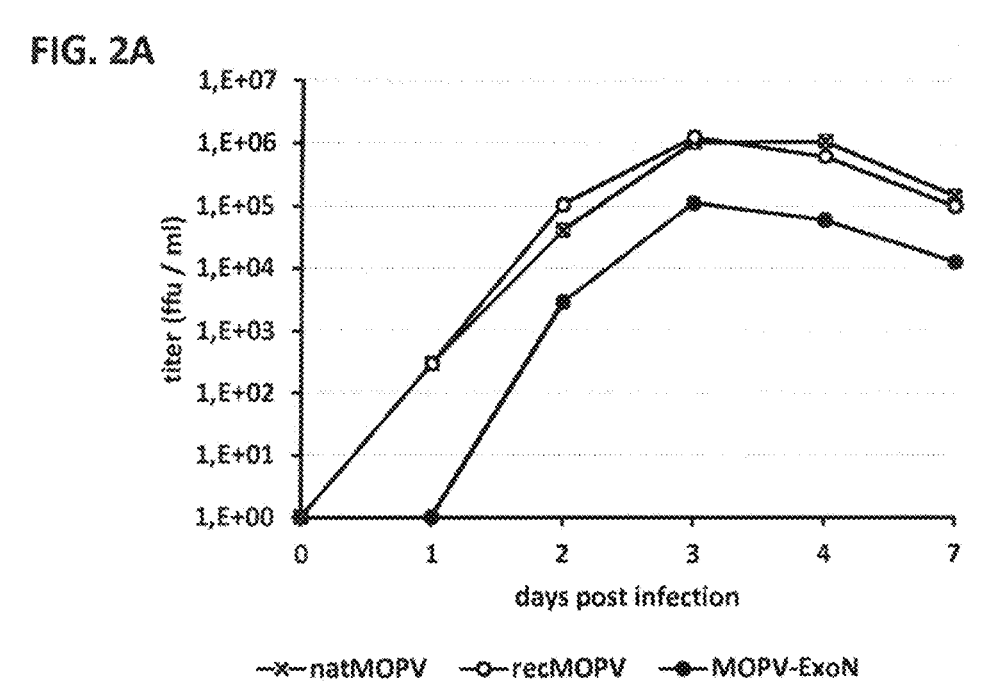

FIGS. 2A to 2B show replicative properties of MOPV-ExoN. (A) Vero E6 cells were infected at a MOI of 0.01. Celt supernatants were collected daily for up to 7 days, and virus concentration was determined by plaque assay. Results are expressed in tog of Focus-Forming Unit/ml (log FFU/ml). (B) Monocytes-derived Dendritic Cells (left panel) and Macrophages (right panel) were infected with rec-, nat-MOPV or MOPV-ExoN, at a MOI of 0.1. Supernatants were harvested daily for up to 4 days, and viral titers were determined. Data are representative of 3 different experiments, error bars mean Standard Error.

Figure 3A:
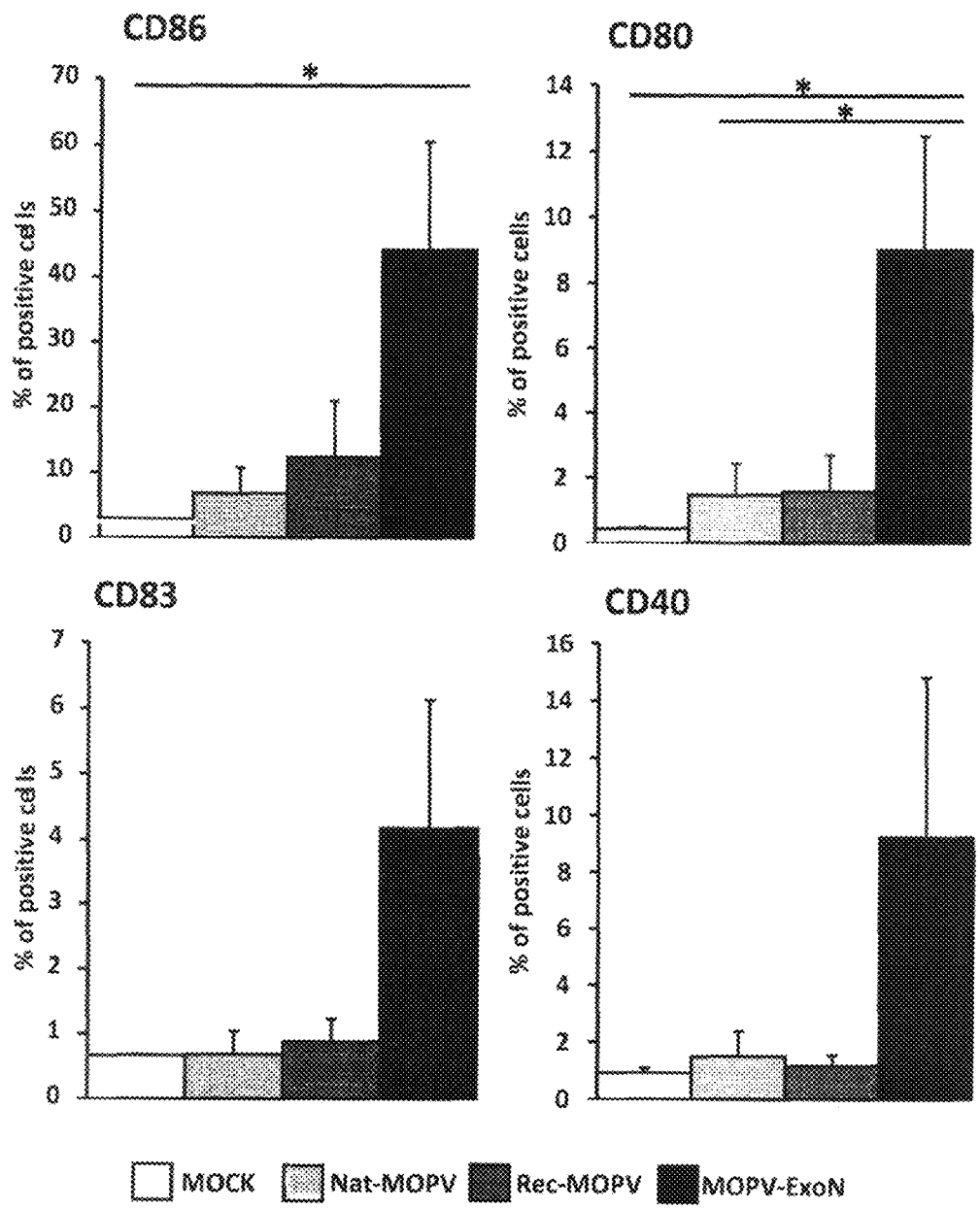
Figure 3B:
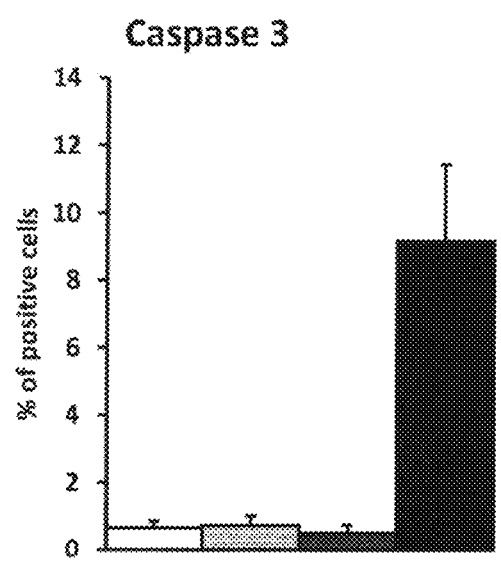

FIGS. 3A to 3B show immunological properties of MOPV ExoN. Monocytes-derived Dendritic Cells (panel A) or Monocytes-derived Macrophages (panel B) were infected at a MOI of 1 with nat-, rec-MOPV or MOPV-ExoN, or MOCK-infected. 48 h post-infection, cells were harvested and analysed by Flow Cytometry for expression of CD80, CD83, CD40 and CD86 surface markers, and in the case of Macrophages, for intra-cellular presence of activated Caspase 3. Data are expressed in percentage of total cells. Data are expressed as the mean of 4 different experiments, and error bars mean Standard Errors. (*): $P<0.05$; (): $P<0.01$; (*): $P<0.001$.

Figure 4A:
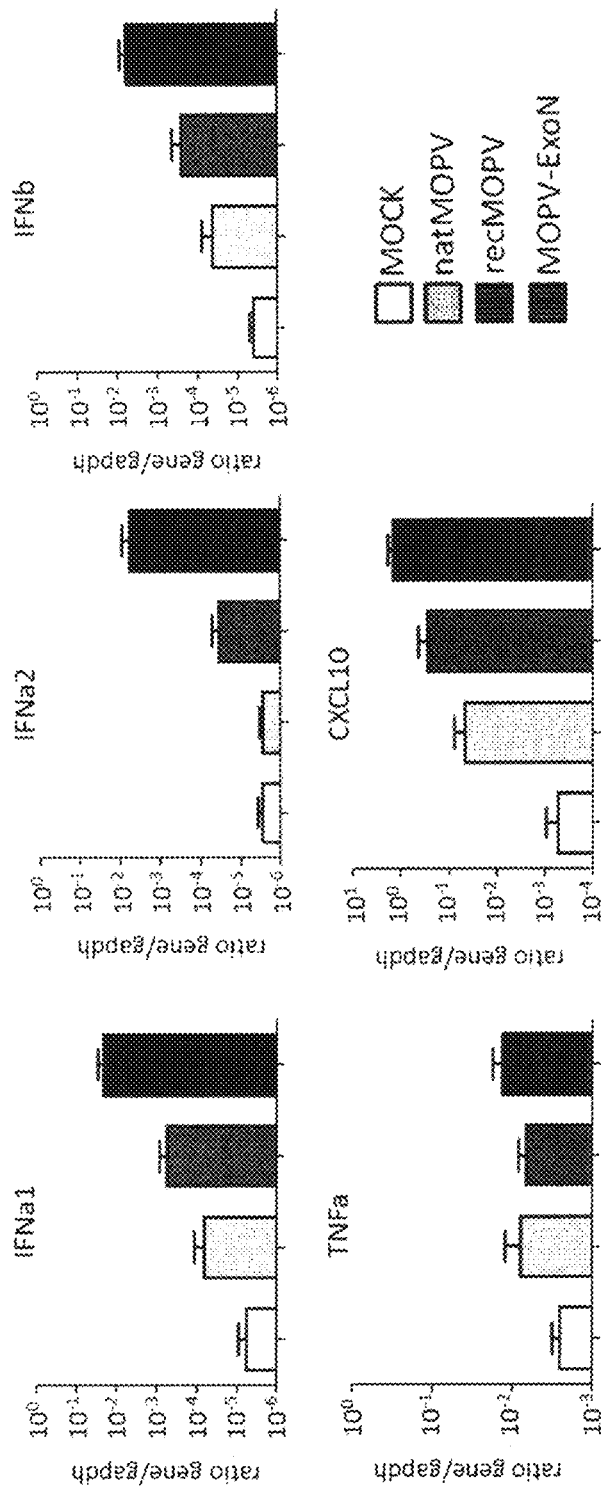
Figure 4B:
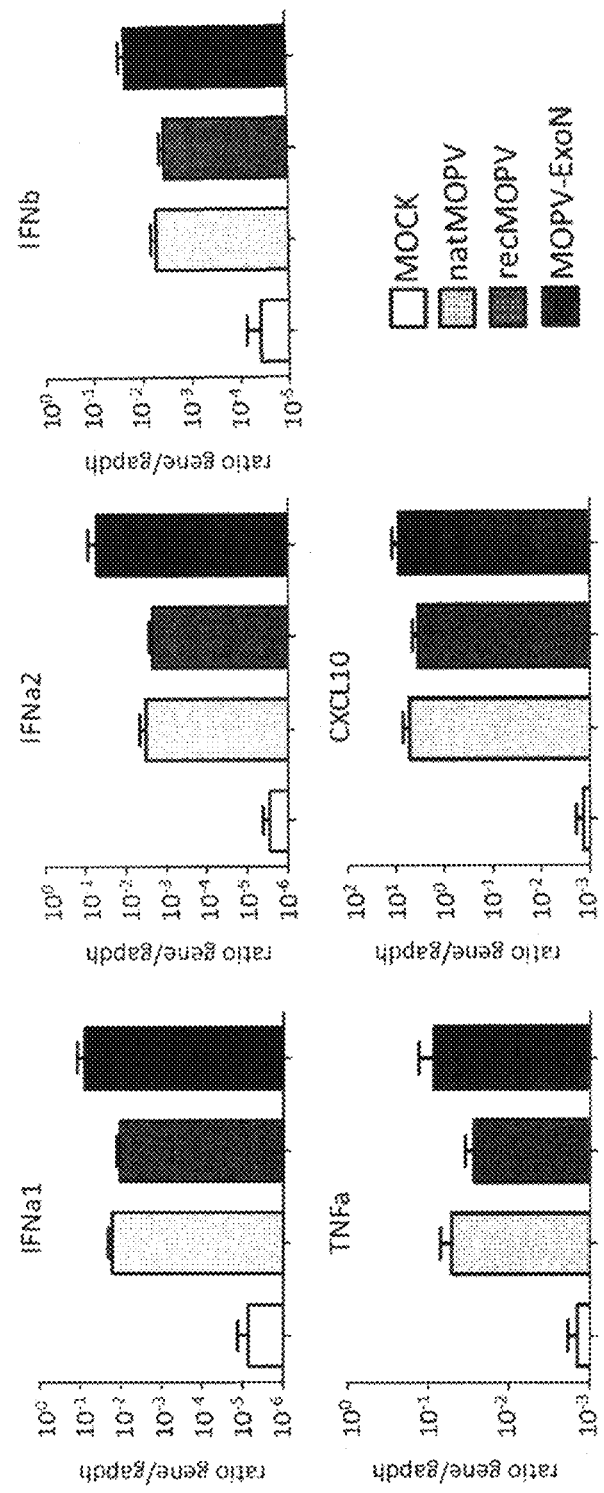

FIGS. 4A to 4B show activation of innate immunity by MOPV-ExoN. Monocytes-derived Dendritic Cells (panel A) or Monocytes-derived Macrophages (panel B) were infected at a MOI of 1 with nat-, rec-MOPV or MOPV-ExoN, or MOCK-infected. 24 h post-infection, cells were harvested and cellular RNA was extracted, reverse-transcribed using oligo-dT primers, and submitted to quantitative PCR for IFNalpha1, IFNalpha2, IFNbeta, TNFalpha and CXCL10. Data are represented as normalized expression to GAPDH housekeeping gene, and are the mean of 4 independent experiments, error bar mean Standard Errors. (*): $P<0.05$.

Figure 5:
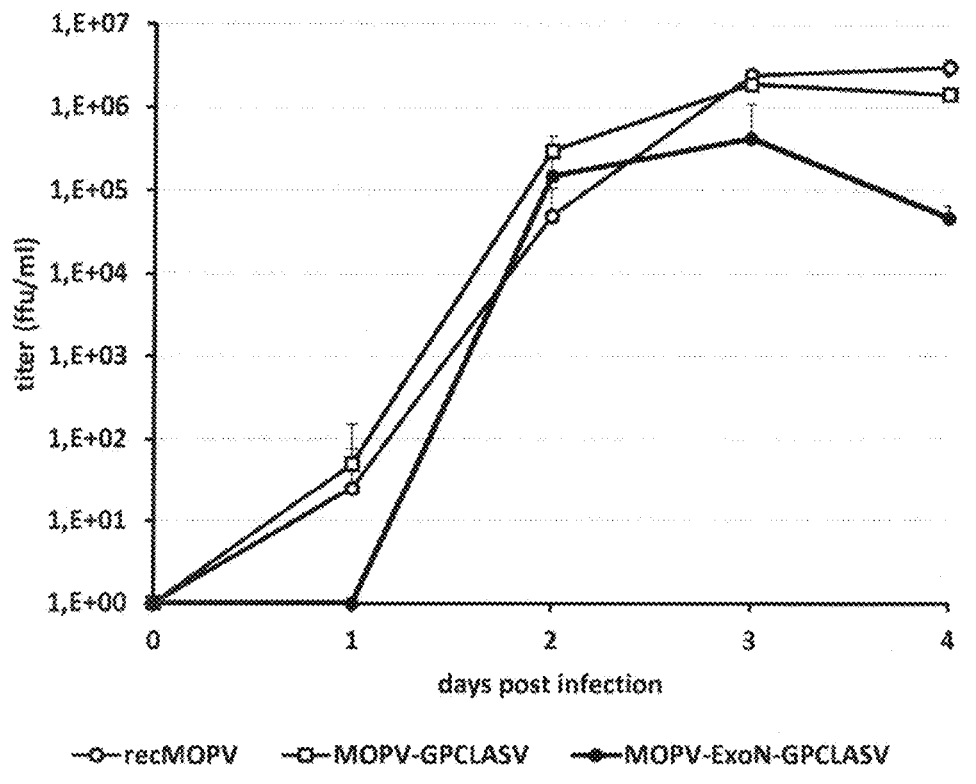

FIG. 5 shows the impact of swapping of gp genes on viral replication. Vero E6 cells infected with rec-MOPV, rec-MOPV-GP$_{LASV}$ or rec-MOPV-ExoN-GP$_{LASV}$, at a MOI of 0.01. Cell supernatants were collected 24, 48, 72 and % hours post-infection, and viral titers, determined by plaque assays, are expressed in tog of Focus Forming Units/mi (log FFU/ml). Data represent means of two concomitant experiments, for which each titre was determined twice. Error bars mean Standard Error.

Figures 6A, 6B:
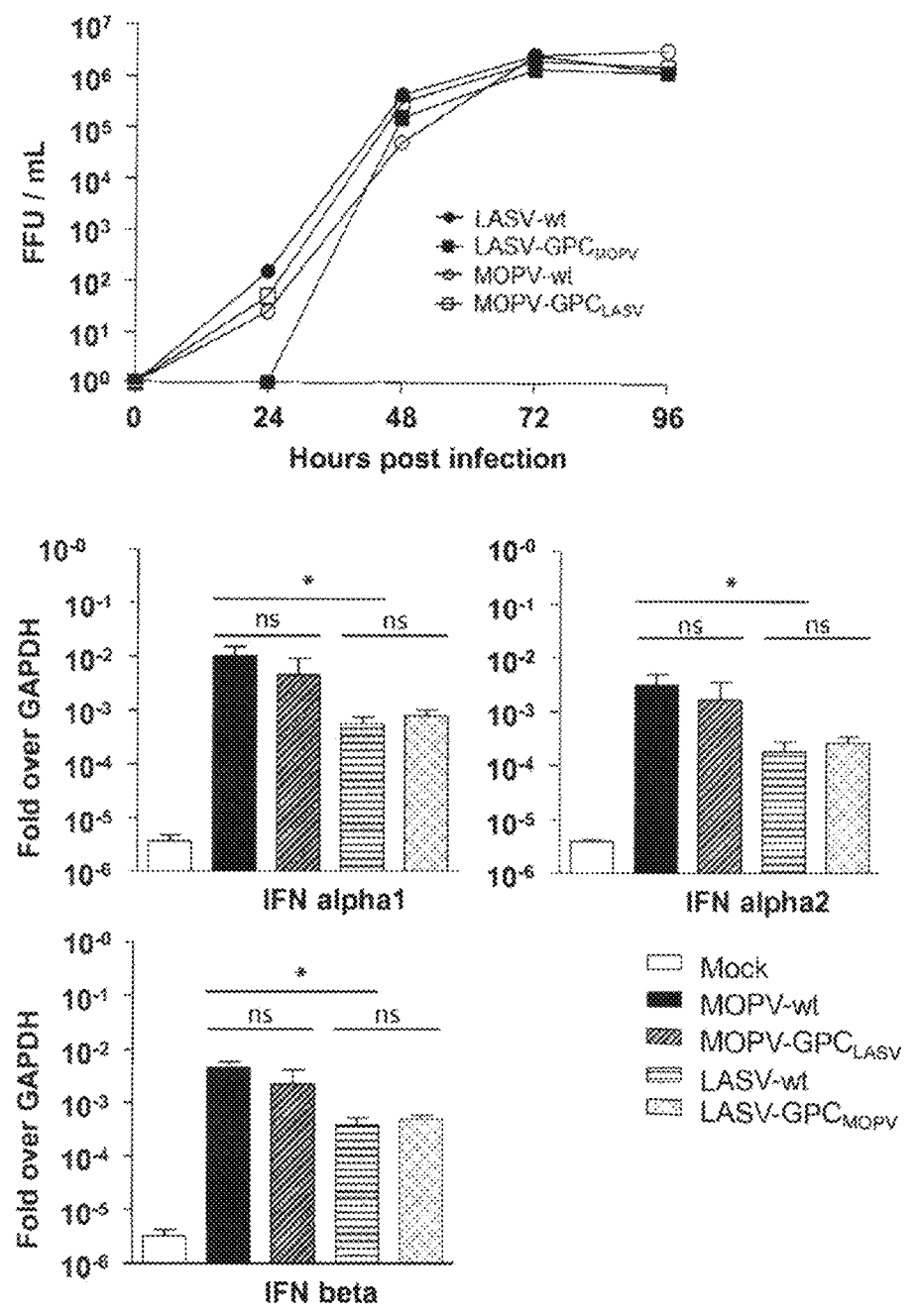

FIGS. 6A to 6B show that Lassa GPC is not involved in the type I IFN response during infection. (A) Kinetics of LASV-wt, LASV-GPC$_{MOPV}$, MOPV-wt and MOPV-GPC$_{LASV}$ viruses in VeroE6 cells infected at MOI of 0.01. Viral titers were determined by titration of culture supernatants in VeroE6 and expressed as logs of Focus Forming Units/ml (FFU/mL). (B)

Human monocyte-derived macrophages were mock infected or infected at MOI of 1 with LASV-wt, LASV-GPC$_{MOPV}$, MOPV-wt and MOPV-GPC$_{LASV}$. Total cellular RNA was extracted using RLT reagent (Qiagen). The levels of IFN-alpha1 (left graph), IFN-alpha2 (middle graph), and IFN-beta (right graph) mRNAs in mock infected or infected cells were determined by quantitative RT-PCR 24 h after infection. The results reported are the numbers of copies of the mRNA considered/number of copies of GADPH mRNA and represent the mean±standard error from three independent experiments (different donors). *=$P<0.05$; ns=not statistically relevant.

FIGS. 7A to 7E show the consolidation of the ExoN KO activity. (A) Residues involved in the coordination of the divalent cation mandatory for the ExoN activity of the nucleoprotein NP and proposed mutants; SEQ ID NO. 8: D390, E392, G393, H430, 0467, H529, D534; SEQ ID NO. 9: ExoNM; SEQ ID NO. 10: ExoNM3; SEQ ID NO. 11: ExoNM4; SEQ ID NO. 12: ExoNM5; SEQ ID NO. 13: ExoNM6a; SEQ ID NO. 14: ExoNM6b; SEQ ID NO. 15: ExoNM7. (B) IFN-antagonist activity of the NP mutants in a reporter gene assay. In this assay, the induction of an IFN-derived promoter by Sendai virus (SeV) is assessed in transfected cells expressing different NP mutants. Kinetics of MOPV-wt, MOPV-ExoNM2 and MOPV-ExoNM6b mutant viruses (C) in VeroE6 cells infected at MOI of 0.01 and (D) in human monocyte-derived macrophages infected at MOI of 0. 5. Viral titers were determined by titration of culture supernatants in VeroE6 as mentioned above. (E) Total cellular RNAs were extracted from mock infected or infected macrophages and the levels of IFN-α1 (upper graph), IFN-α2 (middle graph), and IFN-β (lower graph) mRNAs were determined by quantitative RT-PCR 24 h after infection. The results are reported as shown in FIG. 6B.

FIGS. 8A to 8D show that Mopeia M6b based viruses harbouring GPC of cognate arenaviruses activate immune cells and are strong Inducers of the type I IFN response. (A) Infectious foci induced in VeroE6 cells by the different recombinant MOPV-wt and -ExoNM6b based viruses expressing GPC Lassa (Josiah), Lujo, Machupo (Carvallo), Guanarito (INH95551), Chapare and Sabia viruses and revealed by immunostaining. (B) Kinetics of MOPV-wt, MOPV-ExoNM6b, MOPV-ExoNM6b-GPC$_{LASV}$ and MOPV-ExoNM6b-GPC$_{MACV}$ viruses in human monocyte-derived macrophages infected at MOI of 0.05. (C, D) Human monocyte-derived macrophages mock infected or infected at MOI of 0.5 with MOPV-wt, MOPV-ExoNM6b, MOPV-ExoNM6b-GPC$_{LASV}$ and MOPV-ExoNM6b-GPC$_{MACV}$. Flow cytometry detection of cell surface activation markers CD40, CD80 and CD86 in mock or infected human macrophages 48 h post infection (C). Total cellular RNAs were extracted and the levels of IFN-α1 (left graph), IFN-α2 (middle graph), and IFN-β (right graph) mRNAs were determined by quantitative RT-PCR 24 h or 48 h after infection (D). The results are reported as shown in FIG. 66.

FIG. 9 shows a simplified schematic of the Mopeia reverse genetic system.

DETAILED DESCRIPTION

A. Arenaviruses

Arenavirus is a genus of virus that infects rodents and occasionally humans. At least eight arenaviruses are known to cause human disease. The diseases derived from arenaviruses range in severity. Aseptic meningitis, a severe human disease that causes inflammation covering the brain and spinal cord, can arise from the Lymphocytic choriomeningitis virus (LCMV) infection. Hemorrhagic fever syndromes may be derived from infections by guanarito virus (GTOV), junin virus (JUNV), lassa virus (LASV), lujo virus (LUJV), machupo virus (MACV), sabia virus (SABV), or whitewater arroyo virus (WWAV). Arenaviruses are divided into two groups: the Old World and the New World viruses. The differences between these groups are distinguished geographically and genetically.

Arenaviruses are round, pleomorphic, and enveloped with a diameter of 60 to 300 nm. Although they are often miscategorized as negative sense viruses, they are in fact ambisense. This confusion stems from the fact that while sections of their genome are considered negative sense, and encode genes in the reverse direction, other sections encode genes in the opposite (forward/positive sense) direction. This complex gene expression structure is theorized to be the viruses primitive regulatory system, allowing the virus to control what proteins are synthesized when. The life cycle of the arenavirus is restricted to the cell cytoplasm. Virus particles, or virions, are pleomorphic because they vary in appearances but in many cases they are spherical in shape and covered with surface glycoprotein spikes.

Arenaviruses have a segmented RNA genome that consists of two single-stranded ambisense RNAs. The genomic RNA alone is not infectious and the viral replication machinery is required to initiate infection within a host cell. Genomic sense RNA packaged into the arenavirus virion is designated negative-sense RNA, and must first be copied into a positive-sense mRNA in order to produce viral protein. The two RNA segments are denoted Small (S) and Large (L), and code for four viral proteins in a unique ambisense coding strategy. Each RNA segment codes for two viral proteins in opposite orientation such that the negative-sense RNA genome serves as the template for transcription of a single mRNA and the positive-sense copy of the RNA genome templates a second mRNA. Specifically, the S-segment RNA encodes the viral nucleocapsid protein (NP) and the glycoprotein (GP), notably the glycoprotein precursor (GPC); and the L-segment RNA encodes the viral RNA-dependent RNA-polymerase (L) and a small RING-domain containing protein (Z). The separate coding sequences of the two viral proteins are divided by an intergenic region RNA sequence that is predicted to fold into a stable hairpin structure. The skilled person will appreciate that genomic sequences of the various arenaviruses, as well as of the proteins encoded by these viruses, are publicly available. They can be found e.g., on the web site of the Virus Sequence Database(VSD) established and maintained by the Center for Immunology and Pathology, National Institute of Health, Korea Centers for Disease Control and Prevention.

In the application, when reference is made a (RNA) virus, reference is equally (and implicitly) made to a clone of said (RNA) virus, such as a RNA, DNA or cDNA clone.

The extreme termini of each RNA segment contains a highly conserved sequence for recruitment of the viral replication machinery and initiation of viral mRNA transcription and genomic replication. The conserved 5' and 3' RNA termini sequences are complementary and allow each RNA segment to adopt a double-stranded RNA panhandle structure that maintains the termini in close proximity and results in a circular appearance to purified arenavirus genomic templates visualized by electron microscopy.

The Z protein forms homo oligomers and a structural component of the virions. The formation of these oligomers is an essential step for particle assembly and budding. Binding between Z and the viral envelope glycoprotein complex is required for virion infectivity. Z also interacts with the L and NP proteins. Polymerase activity appears to be modulated by the association between the L and Z proteins. Interaction between the Z and NP proteins is critical for genome packaging. The glycoprotein (GP) is synthesised as a precursor molecule (glycoprotein precursor, GPC). It is post-translationally cleaved into three parts: the mature virion glycoproteins GP1 and GP2, and a stable signal peptide (5SP). These reactions are catalysed by cellular signal peptidases and the cellular enzyme Subtilisin Kexin Isozyme-1 (SKI-1)/Site-1 Protease (SIP).

Arenaviruses can be divided into two serogroups, which differ genetically and by geographical distribution. When the virus is classified "Old World", this means it was found in the Eastern Hemisphere in places such as Europe, Asia, and Africa. When it is found in the Western Hemisphere, in places such as Argentina, Bolivia, Venezuela, Brazil, and the United States, it is classified "New World". Lymphocytic choriomeningitis virus (LCMV) is the only Arenavirus to exist in both areas but is classified as an Old World virus. The Old World complex includes Gairo virus, Gbagroube virus, Ippy virus, Kodoko virus, Lassa virus, Lujo virus, Luna virus, Lunk virus, Lymphocytic choriomeningitis virus, Merino Walk virus, Menekre virus, Mobata virus, Morogoro virus, Mopeia virus, Wenzhou virus, and Tacaribe virus. The New World complex includes Amapari virus, Chapare virus, Flexal virus, Guanarito virus, Junin virus, Latino virus, Machupo virus, Oliveros virus, Paraná virus, Patawa virus, Pichinde virus, Pirital virus, Sabia virus, Tacaribe virus, Tamiami virus, and Whitewater Arroyo virus.

A "heterologous nucleic acid" is a nucleic acid sequence that is inserted into a genomic segment of an arenavirus where it does not naturally occur. The heterologous nuclei acid is generally at least 15 nucleotides in length. In some embodiments, it is at least 20, at least 25, at least 30, at least 35, at least 40, at least 45, at least 50, at least 75, or at least 100 nucleotides in length. In some embodiments, the heterologous nucleic acid is a nucleic acid sequence from the genome of a first arenavirus that is Inserted into the genome of a second arenavirus. For example, the first arenavirus may be a pathogenic arenavirus (such as LASV) and the second arenavirus may be a non-pathogenic arenavirus (such as MOPV). In some embodiments, the heterologous nucleic acid encodes an arenavirus protein, such as an arenavirus GP, preferably an arenavirus GPC.

A nucleoprotein is said to have "attenuated exonuclease activity" when the exonuclease activity of the nucleoprotein is reduced by at least 60%, at least 70%, at Least 80%, at least 90%, at least 95%, or at least 98% relative to the exonuclease activity of a reference nucleoprotein in an in vitro exonuclease assay. In some embodiments, the exonuclease activity is abrogated. In some embodiments, the reference nucleoprotein is a naturally occurring nucleoprotein of an arenavirus, such as the nucleoprotein of MOPV strain AN21366 (accession numbers JN561684 and JN561685). The techniques for measuring said exonuclease activity are well known in the art. Such techniques are explained fully in the literature. See, for example Qi, X. et at. Cap binding and immune evasion revealed by Lassa nucleoprotein structure. Nature 468, 779-83 (2010). See also, for example, Hastie K. M. et al. Structure of the Lassa virus nucleoprotein reveals a dsRNA-specific 3' to 5' exonuclease activity essential for immune suppression. Proc Natl Acad Sci USA 108, 2396-401 (2011).

B. Reverse Genetic System for MOPV

The Examples describe a reverse genetic system that may be used to make recombinant attenuated MOPV. Skilled artisans will appreciate that in view of the teachings of this disclosure alternative embodiments of systems may be provided and utilized to practice embodiments of this invention and to make the disclosed recombinant attenuated MOPV and compositions.

The systems typically comprise a recombinant eukaryotic cell that comprises a first nucleic acid sequence comprising a coding sequence for an L segment antigenomic transcript of an MOPV. In some embodiments, the MOPV strain AN21366 (accession numbers JN561684 and JN561685: SEQ ID Nos. 1 & 2) L segment coding sequence is used.

In some embodiments, the coding sequence for an L segment antigenomic transcript of an MOPV is a sequence that is at least 80%, at least 85%, at least 90%, at least 91%, at least 92%, at least 93%, at least 94%, at least 95%, at least 96%, at least 97%, at least 98%, at least 99%, or 100% identical at the nucleotide level to the coding sequence of the L segment antigenomic transcript of MOPV strain AN21366 (accession numbers JN561684 and JN561685: SEQ ID Nos. 1 & 2). In some embodiments, the coding sequence for an L segment antigenomic transcript of an MOPV is a sequence that encodes Z and L(pol) proteins that are each independently at least 80%, at least 85%, at least 90%, at least 91%, at least 92%, at least 93%, at least 94%, at least 95%, at least 96%, at least 97%, at least 98%, at least 99%, or 100% identical at the amino acid level to the Z and L(pol) proteins of MOPV strain AN21366 (accession numbers JN561684 and JN561685: SEQ ID Nos. 1 & 2).

The recombinant eukaryotic cell typically further comprises a second nucleic acid sequence comprising a coding sequence for an S segment antigenomic transcript of an MOPV. In some embodiments, the MOPV strain AN21366 (accession numbers JN561684 and JN561685: SEQ ID Nos. 1 & 2) S segment coding sequence is used. In some embodiments, the coding sequence for an S segment antigenomic transcript of an MOPV is a sequence that is at least 80%, at least 85%, at Least 90%, at least 91%, at least 92%, at least 93%, at least 94%, at least 95%, at least 96%, at least 97%, at least 98%, at least 99%, or 100% identical at the nucleotide level to the coding sequence of the S segment antigenomic transcript of MOPV strain AN21366 (accession numbers JN561684 and JN561685: SEQ ID Nos. 1 & 2). In some embodiments, the coding sequence for an 5 segment antigenomic transcript of an MOPV is a sequence that encodes NP and GPC precursor proteins that are each independently at least 80%, at least 85%, at least 90%, at least 91%, at least 92%, at least 93%, at least 94%, at least 95%, at least 96%, at least 97%, at least 98%, at least 99%, or 100% identical at the amino acid level to the GPC and NP precursor proteins (SEQ ID NOS. 3 & 4, respectively) of MOPV strain AN21366 (accession numbers JN561684 and JN561685: SEQ ID Nos. 1 & 2).

In some embodiments, the second nucleic acid sequence comprises a coding sequence for a chimeric S segment antigenomic transcript of an arenavirus. The second nucleic acid sequence may be a chimeric S segment coding sequence that comprises a coding sequence for an antigenomic transcript for an MOPV nucleoprotein or an attenuated MOPV nucleoprotein, and a coding sequence for an antigenomic transcript for glycoprotein precursor (GPC) of an arenavirus that is not MOPV. In some embodiments, the arenavirus that is not MOPV is LASV. The LASV may be strain Josiah (accession number J04324).

In some embodiments, the MOPV strain AN21366 (accession numbers JN561684 and JN561685: SEQ ID Nos. 1 & 2) S segment nucleoprotein coding sequence is used. In some embodiments, the S segment nucleoprotein coding sequence is a sequence that is at least 80%, at least 85%, at least 90%, at least 91%, at least 92%, at least 93%, at least 94%, at least 95%, at Least 96%, at least 97%, at least 98%, at least 99Y, or 100% identical at the nucleotide level to the coding sequence of the nucleoprotein of MOPV strain AN21366 (accession numbers JN561684 and JN561685: SEQ ID Nos. 1 & 2). In some embodiments, the S segment nucleoprotein coding sequence is a sequence that encodes a nucleoprotein that is at least 80%, at least 85%, at least 90%, at least 91%, at least 92%, at least 93%, at least 94%, at least 95%, at Least 96%, at least 97%, at least 98%, at least 99%, or 100% identical at the amino acid level to the nucleoprotein of MOPV strain AN21366 (accession numbers JN561684 and JN561685: SEQ ID Nos. 1 & 2).

In some embodiments, the encoded nucleoprotein differs from a reference (wild-type) arenavirus nucleoprotein sequence at position D390 or G393. In some embodiments, the encoded nucleoprotein differs from a reference (wild type) arenavirus nucleoprotein sequence at positions D390 and G393. In some embodiments, the encoded nucleoprotein further differs from a reference (wild type) arenavirus nucleoprotein sequence at one, two, three, four, or five positions selected from E392, H430, D467, H529, and D534. In some embodiments, the reference arenavirus nucleoprotein sequence is the MOPV strain AN21366 (accession numbers JN561684 and JN561685) nucleoprotein sequence (SEQ ID NO. 4). In some embodiments, the encoded nucleoprotein differs from a reference (wild-type) arenavirus nucleoprotein sequence by comprising D390A or G393A amino acid substitution. In some embodiments, the encoded nucleoprotein differs from a reference (wild type) arenavirus nucleoprotein sequence by comprising D390A and G393A amino acid substitutions. In some embodiments, the encoded nucleoprotein differs from a reference (wild type) arenavirus nucleoprotein sequence by further comprising one, two, three, four, or five of the amino acid substitutions E392A, H430A, D467A, H529A, and D534A.

The first and/or second nucleic acid sequences may be any suitable vector including a plasmid. The vectors may be the same except that they comprise different coding sequences for the L and the S segment or they may be different. The first and/or second nucleic acid sequences typically further comprise transcription regulatory sequences sufficient to drive expression of the coding sequences for the L and the S segments in a host cell of interest. In some embodiments, the host cell of interest is BHKT7/9 cells. In some embodiments, the first and/or second nucleic acid sequences are present in plasmids that comprise sequences necessary to drive expression by mouse RNA polymerase I.

The systems may further comprise a third nucleic acid sequence encoding an MOPV L(poi) protein. In some embodiments, the systems may further comprise a fourth nucleic acid sequence encoding an MOPV nucleoprotein. In some embodiments, the systems may further comprise a third nucleic acid sequence encoding an MOPV L(pol) protein and a fourth nucleic acid sequence encoding an MOPV nucleoprotein. The third and/or fourth nucleic acid sequences may be present on any suitable vector such as a plasmid. The vector will typically comprise sequences necessary to drive expression of the third nucleic acid sequence encoding an MOPV L(pol) protein and/or the fourth nucleic acid sequence encoding an MOPV nucleoprotein. Suitable sequences necessary to drive expression include a T7 promoter.

The reverse genetic system is useful, for example, to assemble recombinant MOPV. Typically, the recombinant MOPV comprises the NP encoded by the S segment antigenomic transcript present in the recombinant MOPV, however in certain embodiments the recombinant MOPV may be produced such that the NP sequence encoded by the S segment antigenomic transcript present in the recombinant MOPV is different than at least some of the NP protein present in the recombinant MOPV. Typically, the recombinant MOPV comprises GPs, preferably GPCs encoded by the 5 segment antigenomic transcript present in the recombinant MOPV, however in certain embodiments the recombinant MOPV may be produced such that the GP precursor sequence encoded by the S segment antigenomic transcript present in the recombinant MOPV is different than at least some of the GPCs present in the recombinant MOPV.

C. Attenuation of MOPV

LASV NP contains an exonuclease that circumvents the host IFN response by digesting double-strand RNA (dsRNA). dsRNA are not normally present in mammalian cells, and as such, when they appear during viral replication, they are recognized as PAMP (Pathogen-Associated-Molecular-Pattern). Digestion of these replication intermediates allows the virus to escape from the innate defense system. Alignment of MOPV-NP with LASV-NP showed that amino acids critical for this function were conserved between LASV and MOPV, suggesting that exonuclease activity (and subsequent escape to IFN response) was also present in MOPV virus. The inventors confirmed that MOPV NP is able to digest dsRNA using an in vitro approach. This result is surprising because MOPV is non-pathogenic while LASV is.

Mutations were introduced in the MOPV nucleoprotein and the modified nucleoprotein used to generate a recombinant attenuated MOPV.

Advantageously, the recombinant attenuated MOPV of the application still is a live virus.

In the context of the present application, the expression "recombinant MOPV" designates a virus obtained by reverse genetics, i.e. is one which has been manipulated in vitro, e.g. using recombinant DNA techniques to introduce changes to the viral genome. In the meaning of the present application, a recombinant wild-type MOPV (also termed "rec-MOPV") is a Mopeia virus which is obtained by reverse genetics and which comprises a nucleic sequence coding for the reference (wild-type) nucleoprotein. In some embodiments, the recombinant MOPV of the invention is a Mopeia virus in which at least one mutation has been Introduced in the MOPV nucleoprotein and results in the partial or total lost of exonuclease activity of said nucleoprotein.

A "mutation," as used herein, refers to a change in nucleic acid or polypeptide sequence relative to a reference sequence (which is preferably a naturally-occurring normal or «wild-type» or «reference» sequence), and includes translocations, deletions, insertions, and substitutions/point mutations.

A mutation by "substitution" as used with respect to amino acids, refers to the replacement of one amino acid residue by any other amino acid residue, excepted the substituted amino acid residue. Advantageously, small amino acid residues are used for substitution in order to limit any effect on the overall protein structure. For example, alanine residues are used to substitute charged and polar amino acid residues and serine residues are used to substitute apolar amino acids. In some embodiments, the said "any amino acid residue" is an alanine residue. In some embodiments, there may be at least 1, at least 2, at least 3, at least 4, at least 5, at least 6, at least 7 substitutions. The term "amino acid substitution set" or "substitution set" refers to a group of amino acid substitutions. A substitution set can have 1, 2, 3, 4, 5, 6, 7 or more amino acid substitutions.

Attenuation is herein intended in accordance with its ordinary meaning in the field. More particularly, the term "attenuated" (by reference to the expression «recombinant attenuated MOPV») refers to a recombinant Mopeia virus (RNA) or (RNA, DNA or cDNA) clone, which comprises a heterologous glycoprotein (GP), more particularly a precursor (GPC), from a pathogenic arenavirus (i.e., from a non-MOPV arenavirus), and which has a reduced pathogenic phenotype compared to the wild-type pathogenic arenavirus (i.e., compared to the infectious and/or virulent arenavirus), more particularly compared to a wild-type virus of the same genus, species, type or subtype (i.e., compared to an infectious and/or virulent virus of the same genus, species, type or subtype).

A reduced pathogenic phenotype encompasses a reduced infection capacity and/or a reduced replication capacity, and/or a reduced and/or restricted tissue tropism, and/or a default or defect in the assembly of the viral particles, more particularly a reduced infection capacity.

A reduced pathogenic phenotype, more particularly a reduced infection capacity, encompasses a (viral) infection, which is impeded, obstructed or delayed, especially when the symptoms accompanying or following the infection are attenuated, delayed or alleviated or when the infecting virus is cleared from the host.

The application thus provides a recombinant attenuated MOPV or clone thereof which is able to replicate to an extent that is sufficient for inducing an immune response but that is not sufficient for inducing a disease.

Specifically, the data in the examples demonstrate that substitution of amino acid positions D390 and G393 of the MOPV nucleoprotein attenuates the function of the nucleoprotein and that recombinant MOPV comprising the nucleoprotein having attenuated exonuclease activity are also attenuated. In some embodiments, the amino acid substitutions are D390A and G393A and the recombinant attenuated MOPV is named MOPV-ExoN. In some embodiments, the recombinant attenuated MOPV replicates weaker in Vero cells and has a continuous lower titer over time in comparison to non-attenuated MOPV. In some embodiments, replication of the recombinant attenuated MOPV in DC and/or MP is reduced by at least about 10%, at least about 20%, at least about 25%, at least about 30%, at least about 35%, at least about 40%, at least about 50%, at least about 60%, at least about 70%, at least about 80%, at least about 90%, or more, compared to replication of recombinant wild type (rec-MOPV) or wild type MOPV (nat-MOPV) in the same cell type. The techniques for evaluating the replicative properties of a virus are well known for the man skilled in the art. Such techniques are explained fully in the literature. See, for example Baize, S. et al. Lassa virus infection of human dendritic cells and macrophages is productive but fails to activate cells. J Immunol. 172(5): 2861-9 (2004). See also, for example Pannetier, D. et at. Human macrophages, but not dendritic cells, are activated and produce alpha/beta interferons in response to Mopeia virus infection. J Virol. 78(19):10516-24 (2004).

The examples also demonstrate activation of DC and MP by a prototype recombinant attenuated MOPV. Specifically, the examples demonstrate that both recombinant and natural MOPV exhibit a strong activation profile in MP, illustrated by the induction of CD86, CD80, and, to a lesser extent, of CD40, but do not induce DC. However, in both MOPV-ExoN infected MP and DCs, a strong level of expression of CD80, CD83 and CD40 was observed, indicating that cells were activated by MOPV-ExoN, and probably prone to present antigens to lymphocytes. The Level of CD86 was also strongly increased in DC infected with MOPV-ExoN, as compared to MOCK or nat-/rec-MOPV infected cells. This marker is important for co-stimulation and maturation of T lymphocytes, thus indicating that priming of lymphocytes should be efficient in response to infection with MOPV- ExoN. Together, these results obtained with a prototype recombinant attenuated MOPV demonstrate the utility of the recombinant attenuated MOPVs of the invention. Accordingly, in some embodiments the recombinant attenuated MOPV of the invention induces an immune response in DC. In some embodiments, the recombinant attenuated MOPV of the invention Induces an immune response in MP. In some embodiments, the recombinant attenuated MOPV of the invention induces an immune response characterized by an increase in expression of at least one molecule selected from CD80, CD83, CD40, and CD86.

The examples also demonstrate that both MP and DC were controlling MOPV-ExoN replication, and that MOPV-ExoN infection induced apoptosis of infected MP, as reflected by a strong increase in the level of Caspase 3 in MOPV-ExoN-infected MP. Accordingly, in some embodiments, replication of the recombinant attenuated MOPV of the invention in DC and/or MP is controlled. In some embodiments, infection of MP by the recombinant attenuated MOPV of the invention induces expression of Caspase 3. In some embodiments, Infection of MP by the recombinant attenuated MOPV of the invention induces MP cell death.

The examples also demonstrate Induction of an innate immune response in DC and MP infected with a recombinant attenuated MOPV of the invention. Specifically, the examples show that expressions of mRNA in rec-MOPV- and nat-MOPV-infected cells is quite similar, but that the innate response is stronger when DC are infected with MOPV-ExoN, as compared with infection with MOPV (rec- or nat-). This result was also observed in MP, as type I IFNs, TNFalpha and CXCL10 levels were higher in response to MOPV-ExoN than to wild type MOPV. Accordingly, in some embodiments, administration of a recombinant attenuated MOPV of the invention induces an innate immune response in DC and/or MP. In some embodiments, the innate immune response comprises expression of at Least one of type I IFNs, TNFalpha and CXCL10.

The examples demonstrate that introduction of D390A and G393A amino acid substitutions in the nucleoprotein of MOPV produces a recombinant attenuated MOPV that is poorly replicative in immune cells, strongly activates at least one of dendritic cells (DC) and macrophages (MP), and/or is more immunogenic than unmodified MOPV. By adding at least one further amino acid substitution at a position selected from E392, H430, D467, H529, and 0534, a recombinant attenuated MOPV having attenuated ExoN function without reduction in replicative properties is provided. In some embodiments, the further substitution is selected from E392A, H430A, D467A, H529A, and D534A.

In some embodiments, the recombinant attenuated MOPV comprises a heterologous nucleic acid and a nucleic acid encoding a nucleoprotein having attenuated exonuclease activity. The recombinant attenuated MOPV are useful, for example, to induce an immunogenic response against an arenavirus in a subject.

In some embodiments of the recombinant attenuated MOPV, the nucleoprotein comprises an amino acid substitution at amino acid position D390 or G393. In some embodiments of the recombinant attenuated MOPV, the nucleoprotein comprises an amino acid substitution at amino acid position D390 or G393, and further comprises at least one amino acid substitution at a position selected from E392, H430, 0467, H529, and D534. In some embodiments of the recombinant attenuated MOPV, the nucleoprotein comprises amino acid substitutions at amino acid positions D390 and G393.

In some embodiments of the recombinant attenuated MOPV, the nucleoprotein comprises amino acid substitutions at amino acid positions D390 and G393, and further comprises at least one amino acid substitution at a position selected from E392, H430, D467, H529, and D534.

In some embodiments of the recombinant attenuated MOPV, the nucleoprotein comprises a D390A or G393A amino acid substitution. In some embodiments of the recombinant attenuated MOPV, the nucleoprotein comprises D390A and G393A amino acid substitutions. In some embodiments of the recombinant attenuated MOPV, the nucleoprotein further comprises at least one amino acid substitution selected from E392A, H430A, D467A, H529A, and D534A. The recombinant attenuated MOPV comprising amino acid substitutions at amino acid positions D390A, G393A, E392A, H430A, D467A, H529A, and D534A is named MOP-ExoN enhanced.

In some embodiments of the recombinant attenuated MOPV, the heterologous nucleic acid encodes a non-MOPV arenavirus glycoprotein, more preferably a non-MOPV arenavirus glycoprotein precursor. In some embodiments of the recombinant attenuated MOPV, the non-MOPV arenavirus is a Lassa virus (LASV).

In some embodiments, the recombinant attenuated MOPV is poorly replicative in immune cells, strongly activates at least one of dendritic cells (DC) and macrophages (MP), and/or is more immunogenic than unmodified MOPV. In some embodiments, the recombinant attenuated MOPV is poorly replicative in immune cells. In some embodiments, the recombinant attenuated MOPV is strongly activates at least one of dendritic cells (DC) and macrophages (MP). In some embodiments, the recombinant attenuated MOPV is more immunogenic than unmodified MOPV.

In some embodiments, the recombinant attenuated MOPV is poorly replicative in immune cells and strongly activates at least one of dendritic cells (DC) and macrophages (MP).

In some embodiments, the recombinant attenuated MOPV is strongly activates at least one of dendritic cells (DC) and macrophages (MP), and is more immunogenic than unmodified MOPV.

In some embodiments, the recombinant attenuated MOPV is poorly replicative in immune cells and is more immunogenic than unmodified MOPV.

In some embodiments, the recombinant attenuated MOPV comprises a coding sequence for an L segment antigenomic transcript of an MOPV. In some embodiments, the coding sequence for an L segment antigenomic transcript of an MOPV is a sequence that is at least 80%, at least 85%, at least 90%, at least 91%, at least 92%, at least 93%, at least 94%, at least 95%, at least 96%, at least 97%, at least 98%, at least 99%, or 100% identical at the nucleotide level to the coding sequence of the L segment antigenomic transcript of MOPV strain AN21366 (accession numbers JN561684 and JN561685: SEQ ID Nos. 1 & 2). In some embodiments, the coding sequence for an L segment antigenomic transcript of an MOPV is a sequence that encodes Z and L(pol) proteins that are each Independently at least 80%, at least 85%, at least 90%, at least 91%, at least 92%, at least 93%. at least 94%, at least 95%, at least 96%, at least 97%, at least 98%, at least 99%, or 100% identical at the amino acid level to the Z and L(pol) proteins of MOPV strain AN21366 (accession numbers JN561684 and JN561685: SEQ ID Nos. 1 & 2). In some embodiments, any Z and L(pol) proteins present in the recombinant attenuated MOPV are proteins encoded by the coding sequence for an L segment antigenomic transcript of an MOPV that is present in the recombinant attenuated MOPV.

In some embodiments, the recombinant attenuated MOPV comprises a coding sequence for an S segment antigenomic transcript of an MOPV. In some embodiments, the coding sequence for an S segment antigenomic transcript of an MOPV is a sequence that is at least 80%, at least 85%, at least 90%, at least 91%, at least 92%, at least 93%, at least 94%, at least 95%, at least 96%, at least 97%, at least 98%, at least 99%, or 100% identical at the nucleotide level to the coding sequence of the S segment antigenomic transcript of MOPV strain AN21366 (accession numbers JN561684 and JN561685: SEQ ID Nos. 1 & 2). In some embodiments, the coding sequence for an S segment antigenomic transcript of an MOPV is a sequence that encodes NP and GP precursor proteins that are each independently at least 80%, at Least 85%, at least 90%, at least 91%, at least 92%, at least 93%, at least 94%, at least 95%, at least 96%, at least 97%, at least 98%, at least 99%, or 100% identical at the amino acid level to the NP and GP precursor proteins of MOPV strain AN21366 (accession numbers JN561684 and JN561685: SEQ ID Nos. 1 & 2). In some embodiments, any NP and GP proteins present in the recombinant attenuated MOPV are proteins encoded by the coding sequence for an S segment antigenomic transcript of an MOPV that is present in the recombinant attenuated MOPV.

In some embodiments, the coding sequence for an S segment antigenomic transcript of an MOPV present in a recombinant attenuated MOPV of the invention encodes a nucleoprotein that differs from a reference (wild type) arenavirus nucleoprotein sequence at positions D390 and G393. In some embodiments, the encoded nucleoprotein further differs from a reference (wild type) arenavirus nucleoprotein sequence at one, two, three, four, or five positions selected from E392, H430, D467, H529, and 0534. In some embodiments, the reference arenavirus nucleoprotein sequence is from an MOPV strain. In some embodiments, the reference arenavirus nucleoprotein sequence is the MOPV strain AN21366 (accession numbers JN561684 and JN561685: SEQ ID Nos. 1 & 2) nucleoprotein sequence. In some embodiments, the encoded nucleoprotein differs from a reference (wild type) arenavirus nucleoprotein sequence by comprising D390A and G393A amino acid substitutions. In some embodiments, the encoded nucleoprotein differs from a reference (wild type) arenavirus nucleoprotein sequence by further comprising one, two, three, four, or five of the amino acid substitutions E392A, H430A, D467A, H529A, and D534A.

The recombinant attenuated MOPV also comprises a heterologous nucleic acid. The heterologous nucleic acid may be inserted anywhere in the genome of the MOPV. in some embodiments, it is inserted into the S segment. In some embodiments, it is inserted into the L segment. In some embodiments, it is inserted into Z protein coding region. In some embodiments, it is inserted into the L(Pol) coding region. In some embodiments, it is inserted into the NP coding region, in some embodiments, it is inserted into the GP precursor coding sequence. In some embodiments, the heterologous nucleic acid is inserted without deleting bases present in the starting MOPV genome while in other embodiments bases present in the starting MOPV genome are deleted at the site of insertion. In some embodiments, the inserted heterologous nucleic acid is the same size as a corresponding region that is deleted at the site of insertion.

In some embodiments, the recombinant attenuated MOPV comprises a recombinant genomic S segment encoding a non-MOPV arenavirus glycoprotein. The examples demonstrate incorporation of an LASV glycoprotein into a recombinant attenuated MOPV. In such an embodiment, the recombinant attenuated MOPV may be used to induce an immune response against LASV glycoprotein, more preferably against LASV glycoprotein precursor which may be protective or therapeutic against infection by LASV In a host. Accordingly, in the exemplified embodiment, LASV is the targeted arenavirus. In other embodiments, the targeted arenavirus is any non-MOPV arenavirus. In some embodiments, the targeted arenavirus is selected from Gairo virus, Gbagroube virus, Ippy virus, Kodoko virus, Lassa virus, Lujo virus, Luna virus, Lunk virus, Lymphocytic choriomeningitis virus, Merino Walk virus, Menekre virus, Mobala virus, Morogoro virus, Wenzhou virus, Tacaribe virus, Amapari virus, Chapare virus, Flexal virus, Guanarito virus, Junin virus, Latino virus, Machupo virus, Oliveros virus, Parana virus, Patawa virus, Pichinde virus, Pirital virus, Sabiá virus, Tacaribe virus, Tamiami virus, and Whitewater Arroyo virus.

The examples provide strong evidence that introduction of mutations that abrogate exonuclease function of MOPV-NP results in strong attenuation of MOPV. In order to better enhance specific protection against a target arenavirus, the inventors engineered a vaccine candidate against LASV, and to produce a chimeric virus in which the surface GP, more preferably the surface GPC, of MOPV is replaced by the GP, more preferably the surface GPC, of LASV. The examples demonstrate that swapping of the GP, more preferably the surface GPC, coding sequence in the MOPV backbone did not significantly affect the replication properties of MOPV, as MOPV-GPC$_{LASV}$ replicates similarly to rec-MOPV. However, the replication of MOPV-ExoN-GPC$_{LASV}$ was to some extent attenuated compared to rec-MOPV, as also observed for MOPV-ExoN. This indicates that attenuation of the replication capacity of MOPV-ExoN-GPC$_{LASV}$ is due to the defect in the NP exonuclease function and not to the swapping of gp genes between LASV and MOPV. Therefore, this result demonstrates that the recombinant attenuated MOPV platform provided herein is useful for vaccinating against a targeted arenavirus.

D. Compositions

The application also relates to a composition. The term "composition" encompasses pharmaceutical composition, antiviral composition, immunogenic composition and vaccine, more particularly antiviral composition, immunogenic composition and vaccine. The composition of the application comprises at least one recombinant attenuated virus of the application, such as at least one live and attenuated virus of the application.

The invention also includes immunogenic compositions comprising a recombinant attenuated MOPV as described herein. The immunogenic compositions can be formulated according to standard procedures in the art. In certain embodiments, the immunogenic compositions are administered in combination with an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a recombinant attenuated MOPV present in the immunogenic composition, but when the compound is administered alone does not generate an immune response to the recombinant attenuated MOPV. Adjuvants can enhance an immune response by several mechanisms including, e.g., lymphocyte recruitment, stimulation of B and/or T cells, stimulation of macrophages, and stimulation of dendritic cells. When a vaccine or immunogenic composition of the invention comprises adjuvants or is administered together with one or more adjuvants, the adjuvants that can be used include, but are not limited to, mineral salt adjuvants or mineral salt get adjuvants, particulate adjuvants, microparticulate adjuvants, mucosal adjuvants, and immunostimulatory adjuvants. Examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 222021 1), MF59 (Novartis), AS03 (GlaxoSmithKline). AS04 (GlaxosmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et ah, in Vaccine Design: The Subunit and Adjuvant Approach (eds. Powell & Newman, Plenum Press, NY, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et ah, N. Engl. J. Med. 336, 86-91 (1997)).

In certain embodiments, the immunogenic compositions comprise the recombinant attenuated MOPV alone or, preferably, together with a pharmaceutically acceptable carrier. Suspensions or dispersions of the recombinant attenuated MOPV, especially isotonic aqueous suspensions or dispersions, can be used. The pharmaceutical compositions may be sterilized and/or may comprise excipients, e.g., preservatives, stabilizers, wetting agents and/or emulsifiers, solubilizers. salts for regulating osmotic pressure and/or buffers and are prepared in a manner known per se, for example by means of conventional dispersing and suspending processes. The dispersions or suspensions may comprise viscosity-regulating agents. The suspensions or dispersions may be kept at temperatures around 2-4° C., or for longer storage may be frozen and then thawed shortly before use. For injection, the vaccine or immunogenic preparations may be formulated in aqueous solutions, such as in physiologically compatible buffers such as Hanks's solution, Ringer's solution, or physiological saline buffer. The solution may contain formulatory agents such as suspending, stabilizing and/or dispersing agents.

In certain embodiments, the compositions described herein additionally comprise a preservative, e.g., the mercury derivative thimerosal. In some embodiments, the pharmaceutical compositions described herein comprises 0.001% to 0.01% thimerosal. In other embodiments, the pharmaceutical compositions described herein do not comprise a preservative.

The immunogenic compositions may comprise from about $10^2$ to about $10^{12}$ focus forming units of the recombinant attenuated MOPV. Unit dose forms for parenteral administration are, for example, ampoules or vials. e.g., vials containing from about $10^2$ to $10^{12}$ focus forming units or $10^4$ to $10^{14}$ physical particles of recombinant attenuated MOPV.

In some embodiments, an immunogenic composition provided herein is administered to a subject by, including but not limited to, oral, intradermal, intramuscular, intraperitoneal, intravenous, subcutaneous, percutaneous, intranasal and inhalation routes, and via scarification (scratching through the top layers of skin, e.g., using a bifurcated needle). In some embodiments, a subcutaneous or intravenous route is used.

For administration intranasally or by inhalation, the preparation for use according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflators may be formulated containing a powder mix of the compound and a suitable powder base such as lactose or starch.

As skilled artisans will appreciate, the dosage of the recombinant attenuated MOPV depends upon the type of vaccination and upon the subject, and their age, weight, individual condition, the individual pharmacokinetic data, and the mode of administration.

E. Use of Recombinant Attenuated MOPV

This invention also provides methods of inducing an immunogenic response in a subject. The methods comprise administering to the subject recombinant attenuated MOPV of the invention, typically in the form of an immunogenic composition of the invention.

In another aspect, the invention also relates to the subject recombinant attenuated MOPV of the invention for use in inducing an immunogenic response in a subject. in a preferred embodiment, said subject recombinant attenuated MOPV is in the form of an immunogenic composition of the invention.

In yet another aspect, the invention provides a use of the subject recombinant attenuated MOPV of the invention for making a vaccine for inducing an immunogenic response in a subject. in a preferred embodiment, said subject recombinant attenuated MOPV is in the form of an immunogenic composition of the invention.

The term "immunogenic response" is intended in accordance with its ordinary meaning in the field, and includes one or several from antibody production, induction of cell mediated immunity, complement activation, development of immunological tolerance, alteration of cytokine production and alteration of chemokine production, more particularly antibody production. Antibody production encompasses neutralizing antibody production, such as seroneutralization.

The subject is typically a mammal, such as a human, a primate, or a non-human primate. In some embodiments, the subject is a mouse, a rat, or a rabbit. In some embodiments, the subject is a domesticated animal, such as, but not limited to, a cow, a horse, a sheep, a pig, a goat, a cat, a dog, a hamster, and a donkey. in some embodiments, the immunogenic response comprises a response to the glycoprotein portion of a recombinant attenuated MOPV of the invention.

The subject recombinant attenuated MOPV or the composition of the application can be used in the prevention and/or treatment and/or palliation, of an arenavirus infection and/or of a disease or disorder induced by an arenavirus. Thus, the invention also relates to the subject recombinant attenuated MOPV or the composition for use in the prevention and/or treatment and/or palliation, of an arenavirus infection and/or of a disease or disorder induced by do arenavirus. The invention also relates to the use of the subject recombinant attenuated MOPV or the composition for making a vaccine for preventing and/or treating and/or palliating, an arenavirus infection and/or a disease or disorder induced by an arenavirus. In some embodiments, the recombinant attenuated MOPV or the composition is used to prevent an arenavirus infection and/or a disease or disorder induced by an arenavirus. In some embodiments the immunogenic response is protective. A protective response is a response that confers immunity to the subject. For example, in some embodiments, the subject is administered a recombinant attenuated MOPV, the recombinant attenuated MOPV comprising a glycoprotein of an arenavirus, preferably a precursor thereof, or an immunogenic composition comprising said recombinant attenuated MOPV and following the administration the subject mounts and immune response to the glycoprotein of the arenavirus. If the immune response confers to the subject an immunity to the arenavirus from which the glycoprotein is derived then the immunogenic response in the subject is protective. As a skilled artisan will appreciate a protective immune response is one that reduces the risk that a subject will become infected with an arenavirus and/or reduces the severity of an infection with an arenavirus. Accordingly, protective immune responses include responses of varying degrees of protection.

According to another embodiment, the invention also relates to the subject recombinant attenuated MOPV of the invention for use in inducing a protective immune response in a subject, in a preferred embodiment, said subject recombinant attenuated MOPV is in the form of an immunogenic composition of the invention.

In yet another embodiment, the invention provides a use of the subject recombinant attenuated MOPV of the invention for making a vaccine for inducing a protective immune response in a subject. In a preferred embodiment, said subject recombinant attenuated MOPV is in the form of an immunogenic composition of the invention.

In some embodiments, the subject is infected with an arenavirus prior to administration of the recombinant attenuated MOPV of the invention or of a composition comprising said recombinant attenuated MOPV, and administration of said recombinant attenuated MOPV or of said composition is therapeutic. In such embodiments, administration of said recombinant attenuated MOPV or of said composition to the subject infected with the arenavirus may have the effect of ameliorating at least one symptom of the arenavirus infection in the subject. In some embodiments, administration of said recombinant attenuated MOPV or said composition to the subject infected with the arenavirus may have the effect of reducing the risk of death of the subject.

In some embodiments, administering the recombinant attenuated MOPV or a composition thereof reduces the risk that a subject will develop an infection with a targeted arenavirus by at least about 10%, at least about 20%, at least about 25%, at least about 30%, at least about 35%, at least about 40%, at least about 50%, at least about 60%, at least about 70%, at least about 80%, at least about 90%, or more, compared to the risk of developing an infection with the targeted arenavirus in the absence of administering the recombinant attenuated MOPV or a composition thereof.

In some embodiments, recombinant attenuated MOPV or a composition thereof reduces the symptoms of an infection of the subject with a targeted arenavirus by at least about 10%, at least about 20%, at least about 25%, at least about 30%, at least about 35%, at least about 40%, at least about 50%, at least about 60%. at least about 70%, at least about 80%. at least about 90%, or more, compared to the manifestation of the symptoms of an infection with the targeted arenavirus in the absence of administering the recombinant attenuated MOPV or a composition thereof.

Other characteristics and advantages of the invention appear in the continuation of the description with the examples and the figures whose legends are represented below.

EXAMPLES

Materials and Methods
Viruses
The MOPV, strain AN21366 (accession numbers JN561684 and JN561685: SEQ ID Nos. 1 & 2) and the LASV, strain Josiah (accession number J04324) were used[20,21] and passaged no more than 4 times on VeroE6 cells. Cell culture supernatants were collected 4 days post-infection and clarified by centrifugation 5 min at 5000 rpm. Viruses were tittered and used as viral stocks for further experiments. Hereafter, this virus is named nat-MOPV to distinguish it from recombinant wild-type MOPV obtained by reverse genetics (rec-MOPV).
Cells
Stably expressing the T7 polymerase. BHK T7/9 cells, were used to rescue recombinant viruses and were maintained as described elsewhere[14]. VeroE6 cells, grown in Glutamax Dulbecco Modified Eagle's Medium (DMEM—Life Technologies) supplemented with 5% FCS and 0.5% Penicillin-Streptomycin, were used for amplification and titration of viral stocks.
Plasmids
The pTM1 plasmid was used to drive the expression of the LPol and the NP proteins under the T7 promoter. pTM1 plasmids expressing MOPV LPol (pTM1-LPol) and MOPV NP (pTM1-NP) were obtained by cloning respectively the LPol and the NP ORFs between the NcoI and XhoI sites of the plasmid. To obtain a complete transcription of both viral segments, the L and 5 sequences in antigenomic orientation of the MOPV were reverse transcribed from viral RNA extracts and the cDNA finally cloned into a plasmid that drives the correct transcription under the control of the mouse RNA polymerase I. For both correct transcription and replication of the viral segments, an extra non templated-G base, was included at the beginning of the cloned sequences[14,22]. All plasmids were sequenced and corrected by site directed mutagenesis to match the consensus sequence of the AN21366 MOPV strain, except for purposely-introduced mutations to discriminate between rec- and nat-MOPV.

The swap of GPC ORFs in pPOLI-MOPV Sag plasmid was generated by the introduction of the BsmBI restriction sites downstream and upstream the Start and Stop codons of MOPV GPC ORF respectively. The GPC ORF of Lassa (Josiah, SEQ ID NO. 16), Lujo (NC_012776; SEQ ID NO. 17), Machupo (Carvallo, KM198592.1; SEQ ID NO. 18), Guanarito (INH95551, AF485258.1; SEQ ID NO. 19), Chapare (NC_010562.1; SEQ ID NO. 20) or Sabia (NC_006317.1; SEQ ID NO. 21) was then inserted into the aforementioned modified plasmid deleted of the MOPV GPC ORF. To generate a pPOLI MOPV Sag based minigenome, a similar strategy was used to generate a pPOLI MOPV Sag FF Luc, where the NP ORF is replaced by the Firefly Luciferase ORF.
Site-Directed Mutagenesis
All mutations were introduced using the site directed mutagenesis strategy accordingly to manufacturer instructions (Agilent). Plasmids were then sequenced to confirm the presence of the desired mutations.

Virus Titration

Supernatants of infected cells were collected and clarified by centrifugation at 5000 rpm for 5 min. Ten-fold serial dilutions of viral supernatants were added to subconfluent VeroE6 cells. One hour after incubation, the cells were covered with a 1:1 mixture of 5% 5VF-DMEM and Carboxy-Methyl Cellulose (CMC), and incubated for 7 days. Cells were then fixed with paraformaldehyde (PFA, SIGMA Aldrich, France), permeabilized with triton, and the presence of the virus revealed with a mix of mouse antibody against the GP (or GPC) and the NP proteins. Results were expressed in FFU/ml (Focus Forming Unit/ml).

Rescue Experiments $4 \times 10^6$ BHK-T7/9 cells were seeded in 75 cm$^2$ flasks. The following day, cells were transfected with pPOLI MOPV SAg and pPOLI MOPV LAg using Fugene 6 reagent (Promega, France). Transfection was performed for 6 h at 37° C. Cells were then washed and left for 5 days in DMEM 2.5% SVF. Supernatants of BHK-T7/9 cells constitute the seed stock. The virus of the seed stock was then amplified on VeroE6 cells. The first passage of seed stock on VeroE6 constitute the "passage 1" virus stock. After titration, the "passage 1" virus was used to infect VeroE6 cells at a multiplicity of infection (MOI) of 0.001 or 0.01. Infection was carried out for 3 or 4 days, before the supernatant collection. This tittered second passage on VeroE6 cells provides the viral stocks used for all other experiments. For all viral stocks, the absence of *mycoplasma* contamination was determined using *Mycoplasma* detection kit (Lonza, Switzerland). Viral RNAs were extracted from stocks using QIAmp (QJAGEN) and amplified by One step RT-PCR (Titan, Roche Applied Biosciences). PCR products were sequenced by Sanger sequencing (GATC, Konstanz, Germany).

Generation of Monocytes Derived Dendritic Cells and Macrophages

Blood samples were obtained from Etablissement Français du Sang (EFS). Mononuclear cells were purified by Ficoll density gradient centrifugation (GE Healthcare). Autologous plasma was collected and decomplemented for 30 min at 56° C. Monocytes were separated from peripheral Blood Leucocytes by centrifugation on a cushion of 50% Percoll (GE Healthcare) in PBS. Remaining PBL were removed from the monocytes fraction with anti-CD3, anti-CD19 and anti-CD56 dynabeads (Life Technologies) or with the Monocyte Isolation Kit Ii, human (Miltenyl Biotec). Macrophages (MP) were obtained by incubating monocytes for 4 to 6 days in RPMI, 10% SVF, 10% autologous plasma supplemented with 100 ng/ml of M-CSF (Macrophage-Colony Stimulating Factor, Miltenyi Biotec). Dendritic cells (DC) were differentiated for 6 days in RPMI 10% SVF supplemented with 1,000. U/mL of GM-CSF (Granulocytes Macrophages Colony Stimulating Factor) and 500 U/mL of IL-4 (both from Peprotech). For both cell types (DC and MP), cytokines were added every 2 days and one-third of the culture medium was replaced.

Flow Cytometry

Surface molecules were stained using fluorescent dye conjugated monoclonal antibodies against CD83, CD80, CD86, CD40, (BD Biosciences) for 30 min at 4° C. Intracellular staining for Caspase 3 was performed using Phycoerythrin conjugated anti-Caspase 3 monoclonal antibody (BD Biosciences) for 20 min, after Cytofix/Cytoperm permeabilization (Beckton Dickinson). Cells were finally washed and resuspended in PBS 1% PFA, before analyse by Flow Cytometry using a Gallios cytometer (Beckman Coulter). Data were analysed using Kaluza software (Beckman Coulter).

RT, cDNA Synthesis and gPCR

RNA was isolated from infected cells using RNeasy Mini Kit (Qiagen), according to manufacturer's instructions. Reverse Transcription (RT) was then performed on total RNAs, using oligo dT primers and Superscript III reverse transcriptase kit according to manufacturer instructions (Life Technologies). For cDNA amplification and cloning, the KOD DNA polymerase (EMD Millipore) and gene specific primers were used.

For RT-qPCR experiments, cDNAs were amplified using Gene Expression Master Mix kit and primer/probe mix developed and optimized for each gene (Applied Biosystems Thermo Scientific), except for type I IFNs developed in house[23]. qPCR assays were run in LightCycler 480 (Roche Applied Biosciences). For all genes, expression was standardized to GAPDH gene, and expressed as fold induction compared to GAPDH.

Statistical Analysis

Statistical analyses were performed using SigmaPlot software (Systat Software Inc, California) or GraphPad Prism 6. Differences among groups were assayed running one-way ANOVA followed by post hoc Holm-Sidak test.

Example 1: Set Up of a Reverse Genetic System for MOPV

The reverse genetic system for MOPV developed here was similar to that used previously for LASV[14]. The short and long segments of MOPV in antigenomic sense were cloned in a plasmid that drives the transcription through the mouse RNA polymerase I. These plasmids were transfected, along with pTM1-NP and pTM1-LPol, into BHKT7/9 cells. The expression of genomic length segments and viral proteins Lpol and NP allowed reconstituting the viral transcription and replication unit RNPs (ribonucleoproteins) from which expression of the four viral genes occurs, ultimately leading to the assembly and the budding of recombinant MOPV (rec-MOPV).

Example 2: Abrogation of Exonuclease Activity in MOPV NP

Previous work[14-16] has shown that LASV NP is able to circumvent IFN response thanks to its exonuclease function, which is able to digest double-strand RNA (dsRNA). Indeed, dsRNA are not normally present in mammalian cells, and as such, when they appear during viral replication, they are recognized as PAMP (Pathogen-Associated-Molecular-Pattern). Digestion of these replication intermediates allows the virus to escape from the innate defence system. Interestingly, this exonuclease function is borne by a DEDDH domain. Alignment of MOPV-NP with LASV-NP showed that amino acids critical for this function were conserved between LASV and MOPV, suggesting that exonuclease activity (and subsequent escape to IFN response) was also present in MOPV virus. We have confirmed that MOPV NP is able to digest dsRNA using an in vitro approach and block the IFN response to dsRNA in cells (data not shown). In addition, mutations of the DDEDH domain (D390, E392, 0530, D534 and H430) abrogate the IFN-antagonist activity of MOPV NP without reducing its ability to support viral transcription/replication. Thus, by analogy with LASV, we designed a MOPV-ExoN virus by introducing the mutations D390A and G393A to knock-down exonuclease function of MOPV in the live virus (FIG. 1). Mutations were introduced in the pPOLI-MOPV-Sag, and this modified plasmid was used as described previously to generate a MOPV-ExoN virus. Both recombinants viruses were passaged twice in Vero E6 cells, and virus sequences were verified. The only mutations retrieved were those introduced purposely, either for abrogation of the Exonuclease function of MOPV, or for the discrimination between natural and recombinant MOPV (silent mutations).

Both rec-MOPV (wild-type virus obtained by reverse genetic system) and MOPV-ExoN (rec-MOPV in which NP 0390 and NP G393 were substituted to Alanine) were characterized for their replicative properties in Vero E6 cells, and compared to the naturally isolated nat-MOPV virus (FIG. 2A). in both cases, viruses were replicating similarly, reaching a replicative peak at 12 hours post-infection, and slightly decreasing afterwards. Nat-MOPV and rec-MOPV have a similar replication pattern. In contrast, MOPV-ExoN is replicating weaker, as reflected by its continuous lower titre over time, even though this virus reaches also a peak 3 days post-infection.

Similarly, replication of those three viruses was measured in DC (FIG. 2B, left panel) and MP (FIG. 2B, right panel). As expected, recombinant and natural MOPV presented a similar behaviour, with a peak at 3 days after infection of DC, and to a lower extent, at 2 days after infection of MP. MOPV-ExoN replication was totally abrogated in both cells. These results indicate that Antigen-Presenting Cells (APC) strongly control replication of our vaccine prototype, thus excluding the possibility of massive and long-lasting replication of this agent after inoculation.

Example 3: Characterization of Dendritic Cells and Macrophages Following MOPV-ExoN Infection In order to evaluate vaccine potential of the MOPV-ExoN prototype, we analyzed its capacity to activate DC and MP. To this end, monocytes-derived DC and MP were either MOCK infected, or infected with nat-MOPV, rec-MOPV or MOPV-ExoN, at a MOI of 1 for 48 hours. Expression profile of CD80, CD83, CD40, and CD86 was quite similar when cells were infected with rec-MOPV or nat-MOPV virus (FIGS. 3A and B). Compared to MOCK-infected cells, both rec- and nat-MOPV showed a strong activation profile in MP, illustrated by the induction of CD86, CD80, and, to a lesser extent, of CD40. This activation was not observed in DC. However, in both MOPV-ExoN infected MP and DCs, a strong level of expression of CD80, CD83 and CD40 was observed, indicating that cells were activated by MOPV-ExoN, and probably prone to presents antigens to lymphocytes. interestingly, CD86 level was also strongly increased in DC infected with MOPV-ExoN, as compared to MOCK or nat-/rec-MOPV infected cells. This marker is important for co-stimulation and maturation of T lymphocytes, thus indicating that priming of lymphocytes should be efficient in response to infection with MOPV-ExoN.

An important feature for a live vaccine candidate is the capacity of cells to eliminate this agent. In our case, both MP and DC were controlling MOPV-ExoN replication, and even more, MOPV-ExoN infection induced apoptosis of infected MP, as reflected by the strong increase in Caspase 3 level in MOPV-ExoN-infected MP. This is an important feature as some arenaviruses, such as lymphochoriomeningitis virus (LCMV), are known to induce persistent infections in cells[24].

We also looked for induction of an innate immune response in DC and MP infected with nat- or rec-MOPV or with MOPV-ExoN (FIG. 4). The expressions of mRNA observed in rec-MOPV- and nat-MOPV-infected cells were quite similar. Interestingly, the innate response was stronger when DC were infected with MOPV-ExoN, as compared with infection with MOPV (rec- or nat-). Even if it was more moderated, this result was also observed in MP, as type I IFNs, TNFalpha and CXCL10 levels were higher in response to MOPV-ExoN than to wild type MOPV.

Altogether, these results concerning the activation of APC in response to MOPV-ExoN virus shed light on the properties of this attenuated virus to be a valuable vaccine prototype: Indeed, this virus is able to strongly induce both innate and probably adaptive immune response, and, on the other hand, its replication remains under control into these cells. Even more, induction of apoptosis of MOPV-ExoN Infected MP is consistent with an absence of persistence in infected cells.

Example 4: Production and preliminary characterization of MOPV-ExoN-GP$_{LASV}$

Nat-MOPV was previously shown to be an efficient vaccine against LASV. However, its safety is difficult to prove and some minor lesions have been described after MOPV infection in mice and non-human primates[25]. Here, we provide strong evidences that introduction of mutations that abrogate Exonuclease function of MOPV-NP results in strong attenuation of MOPV. In order to better enhance specific protection against LASV, we thought to engineer our vaccine candidate, and to produce a chimeric virus in which the surface GP of MOPV has been replaced by the one of LASV. To do so, we manipulated the pPOLI_Sag_MOPV plasmid to replace MOPV gp ORF by LASV gp ORF, in both wild type pPOL_Sag_MOPV and pPOLI_Sag_MOPV_ExoN. Chimeric MOPV-GP$_{LASV}$ and MOPV-ExoN-GP$_{LASV}$ were rescued, titrated, and amplified.

Replication properties of these viruses were assayed by infecting VeroE6 cells at a MOI of 0.01, and collecting supernatants daily for 4 days. Virus titres were determined for each time point, and compared to those obtained for rec-MOPV (FIG. 5).

Swapping of gp gene in MOPV backbone did not significantly affect replication properties of MOPV, as MOPV-GP$_{LASV}$ replicates similarly to rec-MOPV. However, the replication of MOPV-ExoN-GP$_{LASV}$ was to some extent attenuated compared to rec-MOPV, as it was also observed for MOPV-ExoN. Thus, attenuation of replication capacity of MOPV-ExoN-GP$_{LASV}$ is rather due to the defect in NP exonuclease function than to the swapping of gp genes between LASV and MOPV. indeed, the exonuclease activity of NP of arenaviruses might have important role in the conservation of genome integrity, and shutting down this function could imply substantially replication capacity of arenaviruses, even in Vero E6 cells, which are deficient for type I IFN response. All the viruses we generated in this study are able to replicate and to be produced at good infectious titres in Vero E6 cells, which is an important parameter to the required specifications of a vaccine prototype.

Example 5: GPC Swapping does not Affect the Immunogenic Properties of Recombinant Viruses In order to evaluate whether exchange of the GPC of MOPV by the GPC of LASV could affect the immune response of Antigen Presenting Cells (APC), we generated recombinant MOPV and LASV viruses respectively expressing the GPC of LASV or MOPV.

As shown on FIG. 6A, these viruses presented similar growth kinetics on VeroE6 cells, with LASV-GPC$_{MOPV}$ replicating to lower titers at 24 hours post infection but to similar titers than all other viruses by 48 hours post infection and until the end of the replication kinetics. We then infected primary human macrophages with these viruses at a MOI of 1 and analysed their type I IFN responses at 24 hours by RT-qPCR. As shown on FIG. 68, exchanging the GPC protein had no effect on the ability of recombinant viruses to induce type I IFN expression in macrophages. In addition, MOPV-wt an MOPV-GPC$_{LASV}$ were slightly more immunogenic than LASV-wt and LASV-GPC$_{MOPV}$, confirming previously observed results and suggesting than the attenuation of MOPV is not dependent on the GPC protein.

Example 6: Consolidation of the ExoN KO Activity

To avoid any possible reversion of two mutations introduced in the np gene to abrogate the ExoN activity, we thought about mutating more residues in the ExoN site. At least 7 residues have been involved in the function of the ExoN domain: D390, E392, G393, H430, D467, H529 and D534. In addition to the two previously described mutations, D390A and G393A (ExoN), we proximally mutated all the residues of the ExoN domain, thus generating 6 additional mutants (FIG. 7A). We first checked the effect of these mutations on the ExoN activity in a reporter gene assay. In this assay, cells transfected with a plasmid encoding an IRF-3-promoter driven luciferase and a plasmid encoding wild type (wt) or mutant forms of NP were infected with SeV, a strong inducer of IRF-3 and IFN responses. FIG. 7B demonstrate that NP-wt can block the Induction of the luciferase expression in response to SeV. On the contrary, all the mutants of the ExoN domain were affected in their ability to reduce induction of the reporter gene expression.

Figures 7C, 7D:
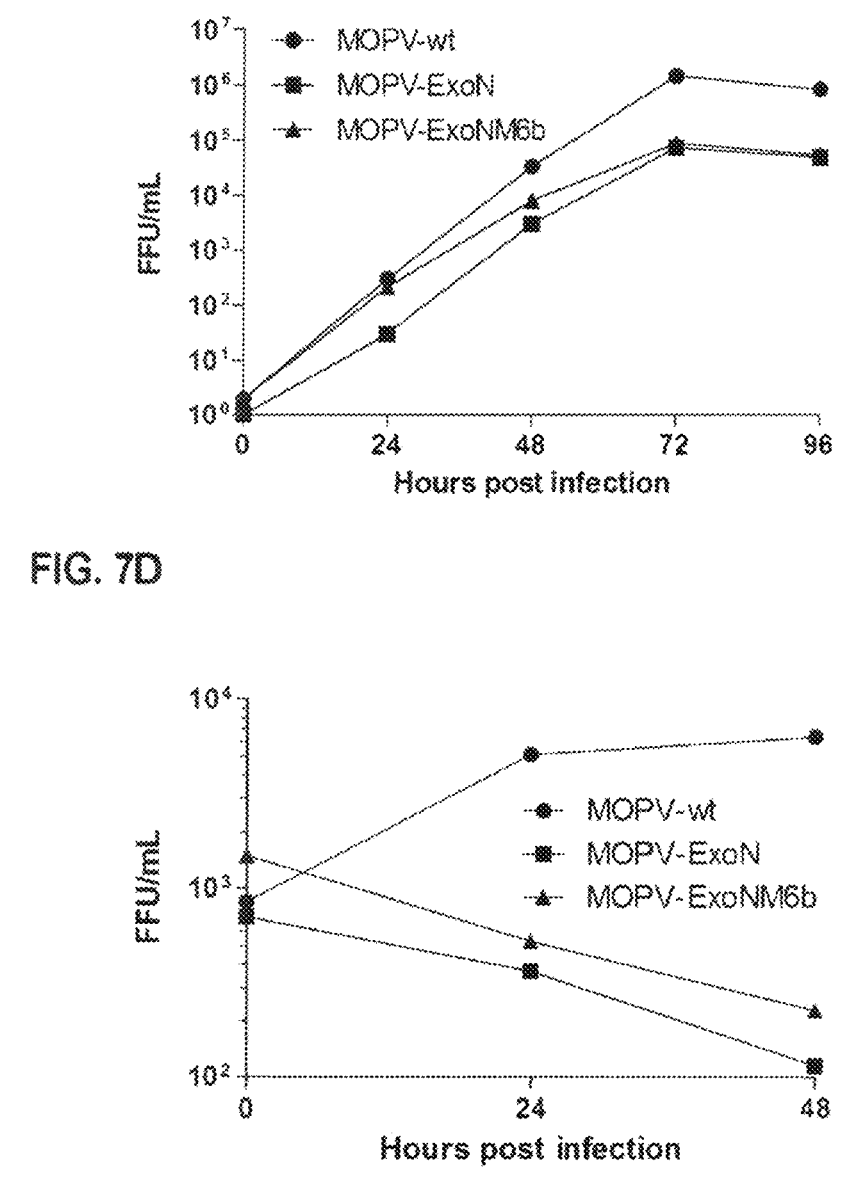
Figure 7E:
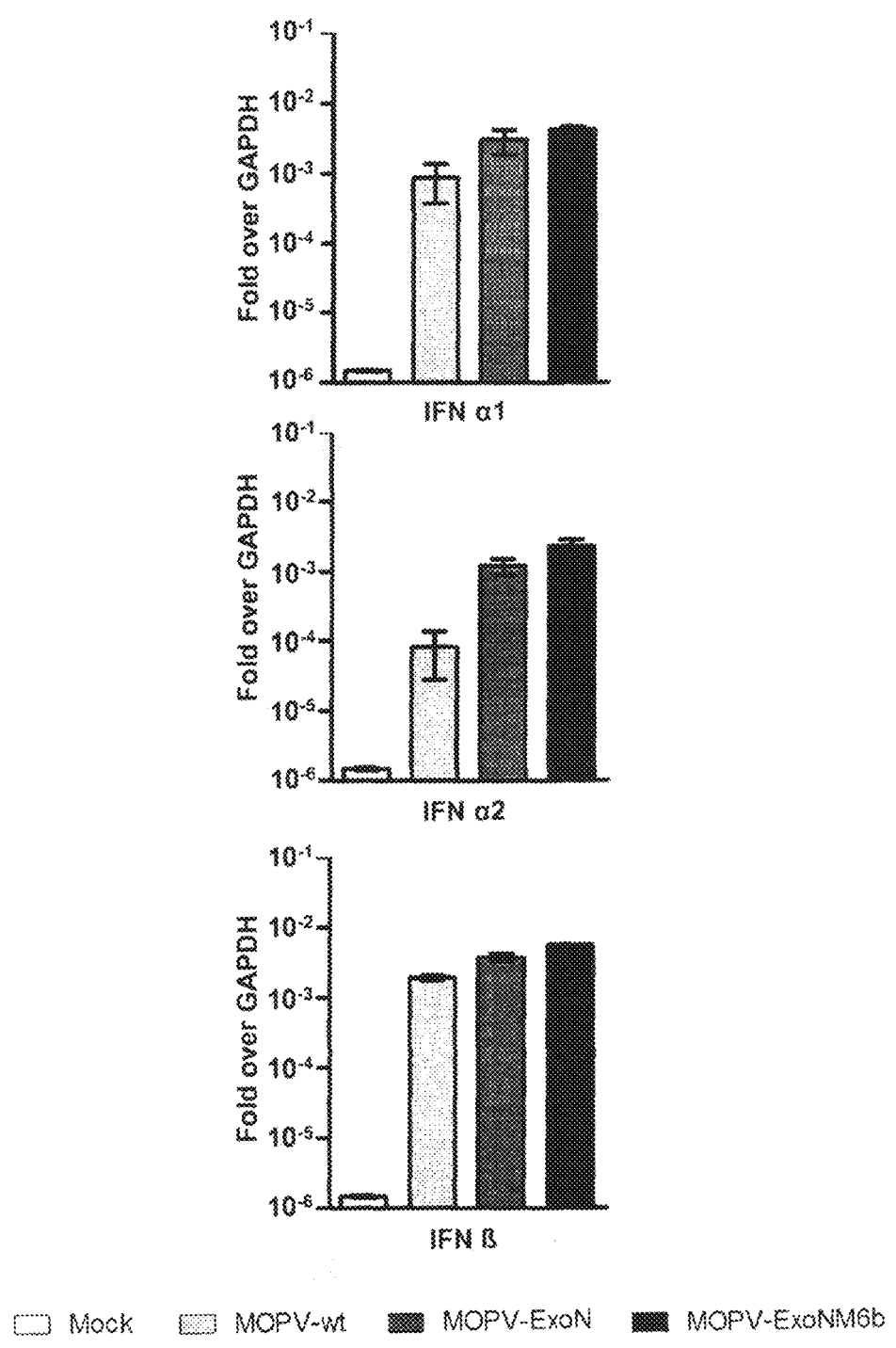

We then introduced the corresponding mutations in reverse genetics plasmids in order to generate recombinant viruses harbouring these mutations. All viruses could be rescued except for MOPV-ExoNM6a and ExoNM7. To avoid the smallest chance to observe any reversion of the NP mutations, the MOPV-ExoNM6b was chosen, containing 6 mutations, as our vaccine platform. We demonstrated that MOPV-ExoNM6b replication in VeroE6 cells was similar to the replication of MOPV-ExoN (FIG. 7C), confirming that additional mutations in the ExoN domain had no additional effect on the capacity of NP to support viral transcription/replication. On the contrary, replication of MOPV-ExoNM6b was abrogated in immune-competent macrophages compared to MOPV-wt, as observed with MOPV-ExoN (FIG. 7D). In infected macrophages, mutant MOPV-ExoN and MOPV-ExoNM6b also induced slightly more type I IFN than MOPV-wt (FIG. 7E). Altogether, these results support the choice of MOPV-ExoNM6b as a vaccine platform.

Figure 8A:
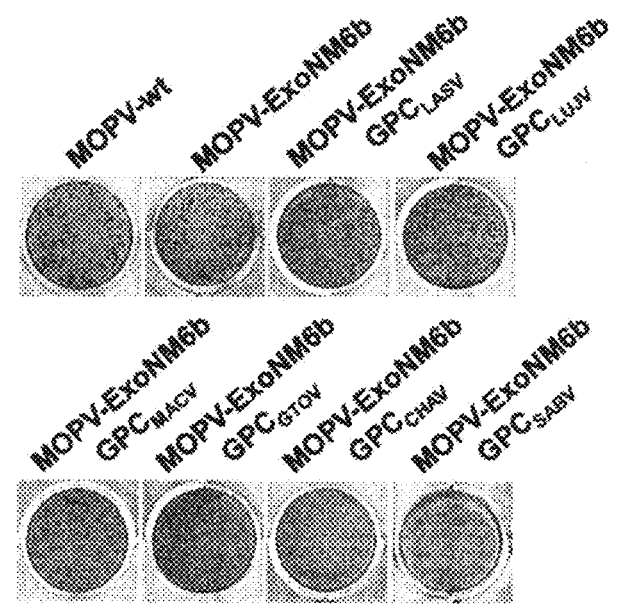

Example 7: Characterization and Immunogenic Properties of MOPV-Based Vaccine Candidates Having chosen the MOPV-ExoNM6b as a vaccine platform, we replaced the GPC protein of MOPV by the GPC protein of other pathogenic arenaviruses: old-world Lassa and Lujo viruses; new-world Machupo, Guanarito, Chapare and Sabia. All recombinant viruses were rescued and replicated on VeroE6 cells (FIG. 8A).

Figures 8B, 8C:
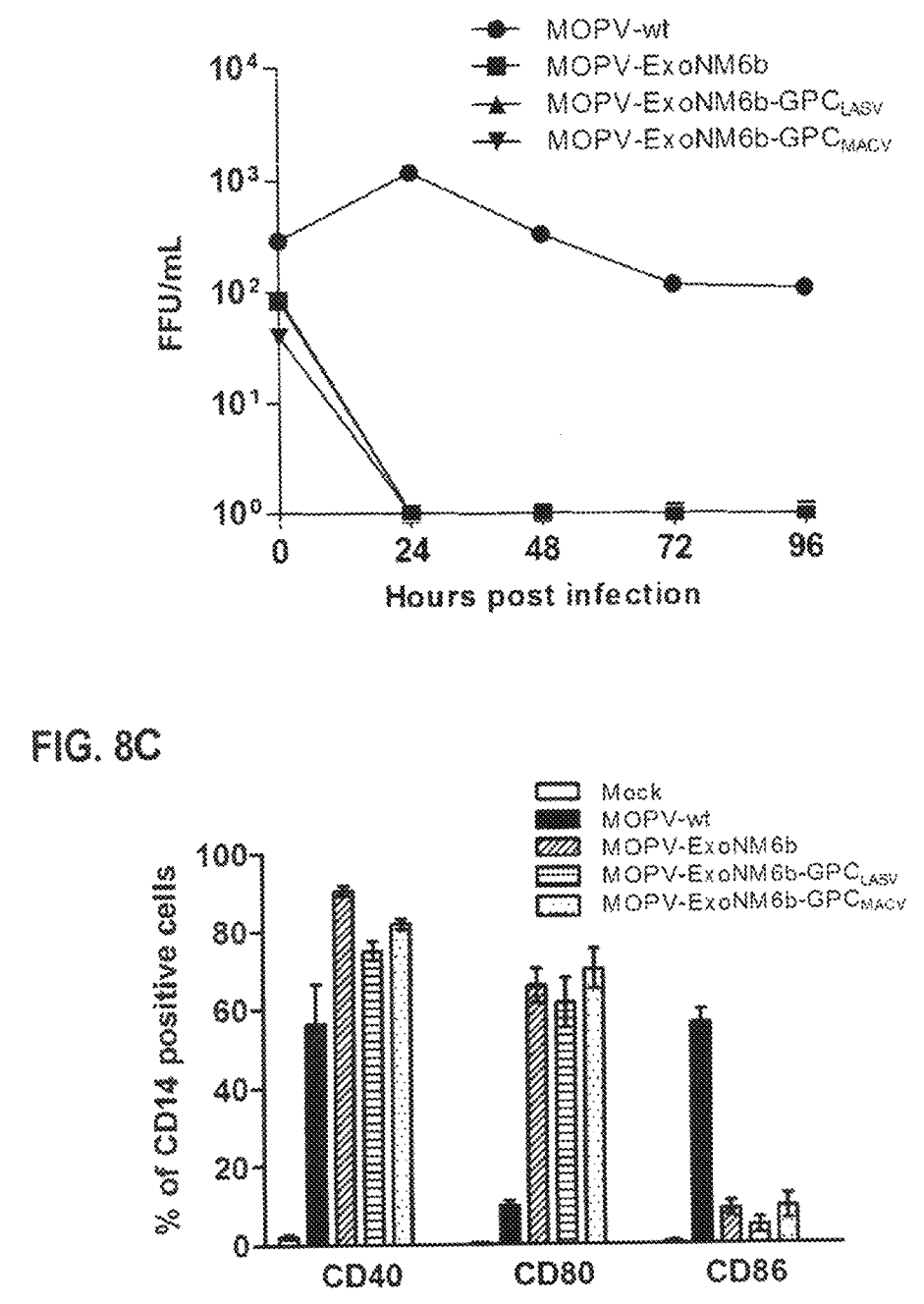

As a proof of principle, we characterized the replication and immunogenic properties of two vaccine candidates, namely MOPV-ExoNM6b-GPC$_{LASV}$ and MOPV-ExoNM6b-GPC$_{MACV}$ in immune-competent macrophages. As expected, while MOPV-wt could replicate in macrophages, MOPV-ExoNM6b-GPC$_{LASV}$ and MOPV-ExoNM6b-GPC$_{MACV}$ could not replicate efficiently in these cells like the parental MOPV-ExoNM6b (FIG. 88), suggesting a control by the immune response. We analysed the expression of activation molecules on the surface of infected macrophages using flow cytometry and showed that all viruses were inducing an upregulation of CD40, CD80 and CD86 compared to non-infected macrophages, with higher CD40 and CD86 induction for ExoNM6b viruses compared to MOP-wt (FIG. 8C). In accordance with these results, all viruses induced high levels of type I IFN genes expression (FIG. 8D).

REFERENCES

1. McCormick, J. B., Webb, P. A., Krebs. J. W., Johnson, K. M. & Smith, E. S. A prospective study of the epidemiology and ecology of Lassa fever. J Infect Dis 155, 437-44 (1987).
2. Frame, J. D., Baldwin, J. M., Jr., Gocke, D. J. & Troup, J. M. Lassa fever, a new virus disease of man from West Africa. I. Clinical description and pathological findings. Am J Trop Med Hyg 19, 670-6 (1970).
3. Cummins, D. et al. Acute sensorineural deafness in Lassa fever. Jarna 264, 2093-6 (1990).
4. Haas, W. H. et at. Imported Lassa fever in Germany: surveillance and management of contact persons. Clin Infect Dis 36, 1254-8 (2003).
5. Briese, T. et at. Genetic detection and characterization of Lujo virus, a new hemorrhagic fever-associated arenavirus from southern Africa. PLoS Pathog 5, e1000455 (2009).
6. Parodi, A. S., Coto, C. E., Boxaca. M., Lajmanovich, S. & Gonzalez. S.
   Characteristics of Junin virus. Etiological agent of Argentine hemorrhagic fever. Arch Gesamte Virusforsch 19, 393-402 (1966).
7. Delgado, S. et at. Chapare virus, a newly discovered arenavirus isolated from a fatal hemorrhagic fever case in Bolivia. PLoS Pathog 4, e1000047 (2008).
8. Webb, P. A., Johnson, K. M., Mackenzie, R. B. & Kuns, M. L. Some characteristics of Machupo virus, causative agent of Bolivian hemorrhagic fever. Am J Trop Med Hyg 16, 531-8 (1%7).
9. Lisieux, T. et at. New arenavirus isolated in Brazil. Lancet 343, 391.2 (1994).
10. Salas, R. et al. Venezuelan haemorrhagic fever. Lancet 338, 1033-6 (1991).
11. Milazzo, M. L., Campbell, G. L. & Fulhorst, C. F. Novel arenavirus infection in humans, United States. Emerg infect Dis 17, 1417-20.
12. McKee, K. T., Jr., Oro, J. G., Kuehne, A. I., Spisso, J. A. & Mahlandt, B. G. Candid No. 1 Argentine hemorrhagic fever vaccine protects against lethal Junin virus challenge in rhesus macaques. Intervirology 34, 154-63 (1992).
13. Fisher-Hoch, S. P. et at. Protection of rhesus monkeys from fatal Lassa fever by vaccination with a recombinant vaccinia virus containing the Lassa virus glycoprotein gene. Proc Natl Acad Sci USA 86, 317-21 (1989).
14. Carnec, X. et at. Lassa virus nucleoprotein mutants generated by reverse genetics induce a robust type I interferon response in human dendritic cells and macrophages. J Virol 85, 12093-7.
15. Hastie, K. M., Kimberlin, C. R., Zandonatti, M. A., MacRae, I. J. & Saphire, E. O. Structure of the Lassa virus nucleoprotein reveals a dsRNA-specific 3 to 5' exonuclease activity essential for immune suppression. Proc Natl Acad Sci USA 108, 2396-401.
16. Qi, X. et al. Cap binding and immune evasion revealed by Lassa nucleoprotein structure. Nature 468, 779-83.
17. La Posta, V. J., Auperin, D. D., Karmin-Lewis, R. & Cole. G. A. Cross-protection against lymphocytic choriomeningitis virus mediated by a CD44- T-cell clone specific for an envelope glycoprotein epitope of Lassa virus. J Viral 67, 3497-506 (1993).
18. Jiang, X. et al. Yellow fever 17D-vectored vaccines expressing Lassa virus GP1 and GP2 glycoproteins provide protection against fatal disease in guinea pigs. Vaccine 29, 1248-57.
19. Fisher-Hoch, S. P., Hutwagner. L., Brown, B. & McCormick, J. B. Effective vaccine for lassa fever. J Viral 74, 6777-83 (2000).
20. Kerber, R. et at. Cross-species analysis of the replication complex of Old World arenaviruses reveals two nucleoprotein sites involved in L protein function. J Viral 85, 12518-28.
21. Auperin, D. D. & McCormick, J. B. Nucleotide sequence of the Lassa virus (Josiah strain) S genome RNA and amino acid sequence comparison of the N and GPC proteins to other arenaviruses. Virology 168, 421-5 (1989).
22. Raju, R. et. at. Nontemplated bases at the 5 ends of Tacaribe virus mRNAs. Virology 174, 53-9 (1990).
23. Baize, S. et at. Role of interferons in the control of Lassa virus replication in human dendritic cells and macrophages. Microbes infect 8, 1194-202 (2006).
24. Wilson, E. B. et at. Blockade of chronic type I interferon signaling to control persistent LCMV infection. Science 340, 202-7.
25. Lange, J. V. et at. Kinetic study of platelets and fibrinogen in Lassa virus-infected monkeys and early pathologic events in Mopeia virus-infected monkeys. Am J Trop Med Hyg 34, 999-1007 (1985).
26. Baize, S. et at. Lassa virus infection of human dendritic ceils and macrophages is productive but fails to activate cells. J Immunol. 172(5):2861-9 (2004).
27. Pannetier, D. et at. Human macrophages, but not dendritic cells, are activated and produce alpha/beta interferons in response to Mopeia virus infection. J Virol. 78(19): 10516-24 (2004).

The invention claimed is:

1. An immunogenic composition comprising a plurality of different types of recombinant attenuated Mopeia viruses (MOPV),
wherein each different type of recombinant attenuated MOPV comprises a heterologous nucleic acid encoding a different non-MOPV arenavirus glycoprotein and a nucleic acid encoding an MOPV nucleoprotein having attenuated exonuclease activity,
wherein the attenuated MOPV nucleoprotein comprises the amino acid substitutions D390X and G393X, wherein said numbering is based upon the isolate AN21366, and
wherein replication of the recombinant attenuated MOPV in dendritic cells (DC) and/or in macrophages (MP) is reduced by at least 10% compared to replication of recombinant wild type (rec-MOPV) or wild type MOPV (nat-MOPV) in the same cell type.

2. The immunogenic composition according to claim 1, wherein the attenuated MOPV nucleoprotein further comprises at least one amino acid substitution selected from E392X, H430X, D467X, H529X, and D534X, wherein said numbering is based upon the isolate AN21366.

3. The immunogenic composition according to claim 1, wherein the amino acid substitution D390X is D390A or the amino acid substitution G393X is G393A.

4. The immunogenic composition according to claim 1, wherein the amino acid substitution D390X is D390A and the amino acid substitution G393X is G393A.

5. The immunogenic composition according to claim 3, wherein the nucleoprotein further comprises at least one amino acid substitution selected from E392A, H430A, D467A, H529A, and D534A, wherein said numbering is based upon the isolate AN21366.

6. The immunogenic composition according to claim 4, wherein the nucleoprotein further comprises at least one amino acid substitution selected from E392A, H430A, D467A, H529A, and D534A, wherein said numbering is based upon the isolate AN21366.

7. The immunogenic composition according to claim 3, wherein the nucleoprotein further comprises the amino acid substitutions E392A, H430A, D467A and D534A, wherein said numbering is based upon the isolate AN21366.

8. The immunogenic composition according to claim 4, wherein the nucleoprotein further comprises the amino acid substitutions E392A, H430A, D467A and D534A, wherein said numbering is based upon the isolate AN21366.

9. The immunogenic composition according to claim 1, wherein the recombinant attenuated MOPV is poorly replicative in immune cells, strongly activates at least one of dendritic cells (DC) and macrophages (MP), and/or is more immunogenic than unmodified MOPV.

10. The immunogenic composition according to claim 1, wherein the attenuated MOPV nucleoprotein is the same in each of the different types of recombinant attenuated MOPV of the immunogenic composition.

11. The immunogenic composition according to claim 1, wherein the attenuated MOPV nucleoprotein is different in at least two of the different types of recombinant attenuated MOPV of the immunogenic composition.

12. The immunogenic composition according to claim 1, wherein the attenuated MOPV nucleoprotein is different in all of the different types of recombinant attenuated MOPV of the immunogenic composition.

13. The immunogenic composition according to claim 1, wherein the non-MOPV arenavirus is selected from the group consisting of: Gairo virus, Gbagroube virus, Ippy virus, Kodoko virus, Lassa virus (LASV), Lujo virus (LUJV), Luna virus, Lunk virus, Lymphocytic choriomeningitis virus (LCMV), Merino Walk virus, Menekre virus, Mobala virus, Morogoro virus, Wenzhou virus, Tacaribe virus, Amapari virus, Chapare virus, Flexal virus, Guanarito virus (GTOV), Junin virus (JUNV), Latino virus, Machupo virus (MACV), Oliveros virus, Paraná virus, Patawa virus, Pichinde virus, Pirital virus, Sabiá virus (SABV), Tacaribe virus, Tamiami virus, and Whitewater Arroyo virus (WWAV).

14. The immunogenic composition according to claim 1, wherein the non-MOPV arenavirus is Lassa virus.

15. The immunogenic composition according to claim 1, wherein the non-MOPV arenavirus glycoprotein is a non-MOPV arenavirus glycoprotein precursor.

16. The immunogenic composition according to claim 1, further comprising an adjuvant, a pharmaceutically acceptable carrier, an excipient, a preservative, or any combination thereof.

17. A method for inducing an immunogenic response against an arenavirus in a subject, comprising administering to said subject the immunogenic composition of claim 1.

18. The method according to claim 17, the immunogenic composition is administered in combination with an adjuvant, wherein the adjuvant is administered before, concomitantly with, or after administration of the immunogenic composition.

19. A vaccine against pathogenic arenaviruses, comprising the immunogenic composition of claim 1.

* * * * *

SEQUENCE LISTING

```
<160> NUMBER OF SEQ ID NOS: 21

<210> SEQ ID NO 1
<211> LENGTH: 6588
<212> TYPE: DNA
<213> ORGANISM: Mopeia mammarenavirus

<400> SEQUENCE: 1
ggagatgggg cagatagtca ccttctttca agaggtgcca cacatccttg aagaagtgat      60
gaacattgtg ctgatgaccc tctcaatctt ggccatccta aagggcatct acaatgtgat     120
gacctgtgga atcatcggtt tgataacatt tttgttcttg tgtgggagat catgctcaag     180
catctataag gacaactatg agttcttctc tctcgacctc gacatgtctt cactgaatgc     240
aacgatgcct ctctcctgct caaagaacaa ctcccatcac tacatccaag ttgggaatga     300
gacaggccta gagctgacat tgacaaacac tagcataatt gatcataagt tttgcaacct     360
gtctgatgct cacaggagga atctttatga caaagcactt atgtcaatct tgacaacatt     420
ccacctaagc attccagatt ttaaccaata tgaggcaatg tcatgtgatt ttaacggagg     480
gaagatctca attcaataca acctgtccca ctcaaattat gtggatgccg gcaaccactg     540
tggcactatt gcaaatggca ttatggatgt ttttagaaga atgtattgga gcacctccct     600
ttcggttgcc tctgacataa gtgggactca atgcatacag accgattata agtatttgat     660
tattcagaac acatcatggg aggatcattg catgttctca agaccctcac ccatgggatt     720
tttaagcctt ctgtcacaga gaaccaggaa tttctacatc tcaagaagac ttttgggtct     780
ttttacatgg acttgagtg actcggaagg gaacgacatg ccaggtggtt actgtctcac     840
aaggtctatg ctaatagggc ttgatctgaa atgctttggg aacactgcca ttgcgaagtg     900
taatcaggca catgatgaag aattctgtga catgctccgc ctttttgatt ttaataaaca     960
agcaattagc aaactgaggt ctgaagttca gcagagcata aatttgataa ataaagctgt    1020
caacgccctc atcaatgatc aactggtcat gaggaaccat tgagagatc taatgggtat    1080 tccttattgc aactactcta agttttggta cttgaatgat actaggacag ggagaacatc    1140
```

```
cctcccaaag tgttggcttg tgaccaatgg gtcataccta aatgaaaccc agttctcaac    1200
agaaattgag caagaagcca ataacatgtt cactgacatg ttgaggaagg agtatgagaa    1260
aaggcagagc acaacacctc tggggttagt agatcttttt gttttctcca ctagctttta    1320
tttgatctcc gtgttcctcc acctaatcaa aattccaaca catagacaca taaaaggcaa    1380
gccttgcccg aaaccacaca gactcaatca catggcaatc tgttcctgtg gcttctataa    1440
gcaaccaggt ctccccacac aatggaaaag gtgaagaaca ggggcacccc cgagacccac    1500
cgccttcggc ggtgggtctc gggggcctgg agtgactgtt ccttgatggc ctccacgacc    1560
caccgccaga ggcggtgggt cgtggaggtg tcccttctta caggacaact ctgggaggac    1620
ctgttctaaa caccaggtct ctactcaaga ctggtctggg ggttggaatt tgtggactcc    1680
ctatgactgc tgcttcaaac atgagacaat ccagcaatgc acagtgtggt gtcacttctt    1740 cctttgccacc tctcttcttc ttttgcgtta caatccccgt atgcattcta caaaggtgtt    1800
tgtattcatc ccagatctta tcctcaaatt ttcttgcatc gtctttctgc atggacacat    1860
caatcagttt tatgtccctc ctgttctggg agtcaagaag cttctgatg tcatcagcac     1920 cttgacacga caagaccatg ttcttttggca ggctctcaat tacagcactt gtcaaccccg    1980
gctgaactga gaataggtct tggatgtcaa tgccatgaga gtgtttggag tcttgtttga    2040
attgtttaat gtctgttggt tccctgtaaa aatgaatata ctgaccatta ttaggttgat    2100
agatagctat ctccacgggg tcttcaggtc tcccttctat gtcaatccat gtcttagcat    2160
ttggatccaa ttgcaacatg ctgtctttga gttccattgt ctgagagtag gtcaaaccag    2220
caggcatgcc ttgggcctga gcgagtctgt tggagttacc tttgtcaggc tttgcattct    2280
gttgcacatc accactcaga tcaacagttg tgttatccca agccctgccg acgatcgatg    2340
ttcttgatgc tatgtaaggc caaccctctc cagaaagaca tagtttgtag aggagatttt    2400
cataagggtt ccttttccccct ggcgtgtcag agacaaacat tcccaaagaa cgcttgactt    2460
tcaaggcagc cttcaaaatt ccttccaaat tggattttgt tactttgatg gtctccagca    2520
tgtttccgcc gtctattaga caagcaccag ctttcaccgc agctgacagg ctaaaattgt    2580
accctgatat gtttatggca cttttcttgg gctcaatgat ccccaagatt gggtgggtct    2640
gagagagttt gtctaagtca gacatgtttg gatactttgc agtgtacaca agccccaagt    2700
ctgacaacga ttggatcaca tcattcagat ctgcctgccc ttgtttgcac atgcaagcaa    2760
tcgtcaggct tggcattgtc ccaaactgat tgtttaaaag ctctgggttt cgaacatccc    2820
acactctaac aatgccatct ccgagagtgt ttcctgcccg gaacccgcca cccattccga    2880
ccatctgtaa caaaaccctc ctctgttcta gctgctgagc tgttaggttg cccatataga    2940
ctccagcagc aagaggcctc tcacctctga tgacttttgc tttgagtctg tccaggtcgg    3000
cagcaaggac gaggaggtca tcagaggtta gtgtccccac tctcaaaaca ttcttctgtt    3060
ggactgactt taactcaact agattgttca ctgcctggtt taggtccctc aatcttttca    3120
ggtcagagtc atccctcttc tcctttctca tcaacctttg aacattggca acttcagaga    3180
agtccagccc atgaagaagt gcttgagcat cctgatgac ttggatcttt atgttggagc     3240
agtaccctga gagttctctc ctcaggctct gtgtccacaa gaaggacttc acctcctttg    3300
aattggacat tgttggaggc ttttcggtgc agagtctcaa tcttggccat cctaaagggc    3360
atctacaatg tgatgacctg tggaatcatc ggtttgataa cattttttgtt cttgtgtggg    3420 agatcatgct caagcatcta taaggacaac tatgagttct tctctctcga cctcgacatg    3480
```

-continued

```
tcttcactga atgcaacgat gcctctctcc tgctcaaaga caactccca tcactacatc    3540
caagttggga atgagacagg cctagagctg acattgacaa acactagcat aattgatcat    3600
aagttttgca acctgtctga tgctcacagg aggaatcttt atgacaaagc acttatgtca    3660
atcttgacaa cattccacct aagcattcca gattttaacc aatatgaggc aatgtcatgt    3720
gattttaacg gagggaagat ctcaattcaa tacaacctgt cccactcaaa ttatgtggat    3780
gccggcaacc actgtggcac tattgcaaat ggcattatgg atgtttttag aagaatgtat    3840
tggagcacct cccttttcggt tgcctctgac ataagtggga ctcaatgcat acagaccgat    3900
tataagtatt tgattattca gaacacatca tgggaggatc attgcatgtt ctcaagaccc    3960
tcacccatgg gattttaag ccttctgtca cagagaacca ggaatttcta catctcaaga    4020
agacttttgg gtcttttac atggactttg agtgactcgg aagggaacga catgccaggt    4080
ggttactgtc tcacaaggtc tatgctaata gggcttgatc tgaaatgctt tgggaacact    4140
gccattgcga agtgtaatca ggcacatgat gaagaattct gtgacatgct ccgccttttt    4200
gattttaata acaagcaat tagcaaactg aggtctgaag ttcagcagag cataaatttg    4260
ataaataaag ctgtcaacgc cctcatcaat gatcaactgg tcatgaggaa ccatttgaga    4320
gatctaatgg gtattcctta ttgcaactac tctaagtttt ggtacttgaa tgatactagg    4380
acagggagaa catccctccc aaagtgttgg cttgtgacca atgggtcata cctaaatgaa    4440
acccagttct caacagaaat tgagcaagaa gccaataaca tgttcactga catgttgagg    4500
aaggagtatg agaaaaggca gagcacaaca cctctggggt tagtagatct ttttgttttc    4560
tccactagct tttatttgat ctccgtgttc ctccacctaa tcaaaattcc aacacataga    4620
cacataaaag gcaagccttg cccgaaacca cacagactca atcacatggc aatctgttcc    4680
tgtggcttct ataagcaacc aggtctcccc acacaatgga aaaggtgaag aacagggggca    4740
cccccgagac ccaccgcctt cggcggtggg tctcggggc ctggagtgac tgttccttga    4800
tggcctccac gacccaccgc cagaggcggt gggtcgtggga ggtgtccctt cttacaggac    4860
aactctggga ggacctgttc taaacaccag gtctctactc aagactggtc tggggggttgg    4920
aatttgtgga ctccctatga ctgctgcttc aaacatgaga caatccagca atgcacagtg    4980
tggtgtcact tcttctttgc cacctctctt cttcttttgc gttacaatcc ccgtatgcat    5040
tctacaaagg tgtttgtatt catcccagat cttatcctca aattttcttg catcgtctt    5100
ctgcatggac acatcaatca gttttatgtc cctcctgttc tgggagtcaa gaagctttct    5160
gatgtcatca gcaccttgac acgacaagac catgttctt ggcaggctct caattacagc    5220
acttgtcaac cccggctgaa ctgagaatag gtcttggatg tcaatgccat gagagtgttt    5280
ggagtcttgt ttgaattgtt taatgtctgt tggttccctg taaaaatgaa tatactgacc    5340
attattaggt tgatagatag ctatctccac ggggtcttca ggtctccctt ctatgtcaat    5400
ccatgtctta gcatttggat ccaattgcaa catgctgtct ttgagttcca ttgtctgaga    5460
gtaggtcaaa ccagcaggca tgccttgggc ctgagcgagt ctgttggagt taccttgtc    5520
aggctttgca ttctgttgca catcaccact cagatcaaca gttgtgttat cccaagccct    5580
gccgacgatc gatgttcttg atgctatgta aggccaaccc tctccagaaa gacatagttt    5640
gtagaggaga ttttcataag ggttcctttc ccctggcgtg tcagagacaa acattcccaa    5700
agaacgcttg actttcaagg cagccttcaa aattccttcc aaattggatt tgttacttt    5760
gatggtctcc agcatgtttc cgccgtctat tagacaagca ccagcttcca ccgcagctga    5820
caggctaaaa ttgtaccctg atatgtttat ggcacttttc ttgggctcaa tgatccccaa    5880
```

```
gattgggtgg gtctgagaga gttttgtctaa gtcagacatg tttggatact ttgcagtgta    5940
cacaagcccc aagtctgaca acgattggat cacatcattc agatctgcct gcccttgttt    6000
gcacatgcaa gcaatcgtca ggcttggcat tgtcccaaac tgattgttta aaagctctgg    6060
gtttcgaaca tcccacactc taacaatgcc atctccgaga gtgtttcctg cccggaaccc    6120
gccacccatt ccgaccatct gtaacaaaac cctcctctgt tctagctgct gagctgttag    6180
gttgcccata tagactccag cagcaagagg cctctcacct ctgatgactt ttgctttgag    6240
tctgtccagg tcggcagcaa ggacgaggag gtcatcagag gttagtgtcc ccactctcaa    6300
aacattcttc tgttggactg actttaactc aactagattg ttcactgcct ggtttaggtc    6360
cctcaatctt ttcaggtcag agtcatccct cttctccttt ctcatcaacc tttgaacatt    6420
ggcaacttca gagaagtcca gcccatgaag aagtgcttga gcatccttga tgacttggat    6480
ctttatgttg gagcagtacc ctgagagttc tctcctcagg ctctgtgtcc acaagaagga    6540
cttcacctcc tttgaattgg acattgttgg aggcttttcg gtgcagag                 6588
```

<210> SEQ ID NO 2
<211> LENGTH: 14462
<212> TYPE: DNA
<213> ORGANISM: Mopeia mammarenavirus

<400> SEQUENCE: 2

```
cgcaccgggg atcctaggca attttgtgga tctttgctga tacttcattc tgcactcaaa      60
gccgcatccg gcaagagtca tggggaaaac gcagtccaag ggacagccca gcacaaatct     120
cctcaaggag acagaaccaa ggcatccagt aataccagat gccaggggaa ctggccctga     180
attctgcaag agctgctggt tcgaaaggag ggggttagtc aggtgcaacg atcactacct     240
atgtttgaac tgtcttacac ttttacacac agtgtcagat aggtgcccca tctgcaaaca     300
caaactaccc ttcagactag agctccagac ccagccgaca gcaccaccag aaatcccacc     360
atcccaaaat cccccacccct acagccctg aggcagaact ccgccccgaa gcccctccca     420
aacacccctc ccctccccc cgggggggacc cccgccggg gctccccccg ggggagatg       480 cgcgagctgt tctcggagca cctactcaat gtcgaggga ggcccaccct cttcaaagag     540
gggcctgcac agcctccctc ttaatctaaa cttcccctct gaagactgga tcatcagtga    600
agcctgcgat ctactgtagc agagactata gcctttaaaa tctgcccaga gtcaattcc    660 ggagaacact ctagtaagga gttttcgta gccttcaggc atgcatcgtc ccacaacccc    720
tataatatca agttgtagcc agtgtagtcc ttggtccatt ctggatctca gcatcttgct    780
caaagatctc tccaagattt cggaatgatc ctccattagc tcaccaataa aaacattaag    840
atcctggtca tggatgttgg ggttgaaggg caggagtttc ctggtccctt caataaggta    900
tcctgagtca acaactaagg ggatttcaac atgctcaggc cctatatgcg tgaaatcatg    960
ttcctccagg tccaggatct cctcattcaa taagacggac aagggtatca catcaggaat    1020 ggggggaacta tccctcaagt agtcacaaat attttcagtg acagcaacc aaattgatgt    1080 ggttttccctt ttaaaccatg tagatgtctg tgcaactctc cagcaatctt taattgcgga    1140
tctttgaaca ctaccactgt aagttacatc aagggaatga ggcttgaata atccaccttc    1200
caacaccacc cctttgaaaa ggaggtggag actaaatttc tctttcaatg attcaccctg    1260
acttctcacc tgaaaatta ctgtgacaga aatttgaacg ctcccaacac tgaggtcggc    1320
aaaagcttca agcagctcac ttaccgactc aaagacgtgc tgctcggtta atcctgatgc    1380
```

```
tatgagctgt cctaagttta gaattgctgg tgcacattca aaatccagcc aagcataacc    1440
tgagtaaaga tcatgcctgt acatgggtct ttcaacaccc ttataaataa ccttttctat    1500
aaaagaagaa aaggggccga ggttgtcaag cccttccgac tcaggaattg aagatctatg    1560
tggaaaccaa gtaaaagaac ctaaagtcct gcttgttgca acgaatggtc tgatgaagga    1620
ctcaaagtag atttgtctca ggaaattttg taccacatca taagtggtca ccacccttc    1680
atccgtgatt gggagatgag acctctcatg tgctattgct aaatctgaag acagaaccac    1740
ataatgctct tctctcttcc acttgacaac atgagaaatt aatgacattg cctcacaatt    1800
cacatctaga accacacaaa gatcaagaaa cttaatcctt ggtgtccacc tcattttcgt    1860
tgatgctagg tcactcatga agggcaagag gtgtctctca aatagagatg ggtaaagtct    1920
tctgaatgag tgaataatat ggttaaaccc caccttgtct tccaagagtt ttgtggtagt    1980
gggcttcatt gggaaatagt cacatggctt gaagggaatt gaggatgttt tctccttcac    2040
tttgggttca cccaacaccc aggaacccag ctcaagtgat gtagataagg ctatgcagaa    2100
gtaatcccaa aggacaggtc tcaagaaacc taacgcttcc tcagctgcct ttgtgtgctc    2160
cttacccaag atccaaagat cgacgcccct aactttcaag ctggaaacag aatccaatgc    2220
tgacagtctt gaaactaatg attttatata ggcggtggac ctatctgaga atcgaacaca    2280
tttgctacct agtgtcttgc aaagacctat gaaacctgat gctatcccac tctgaaaggc    2340
acttttgttg acggcttcac agagcaactt ttgtgcccct cttgtgaaat tagaggataa    2400
cttgctttgc aatgttttca ccaaggtagg cagttttct tccccgagtt caacagcacc    2460
tgtgtaaatg accttctgtc tcatgaccat cttaaaggg tgatgagttg tcaaattaag    2520
ccaacacacc gataaatcct cttctgagag ggtgtcatca ccaacaaggc tggtaagttt    2580
cttgaaggaa tctgcggggt ctcctgacaa gtagatggct gtgaattctt catgaagctc    2640
tcctaatttc agcttattaa aaactgtcct taggaccttc ctaactttct gagtgctttc    2700
tggtaggatt gcctcaatgt tcctcataat cctatagccc ctattgccat caacccaatc    2760
tttaacatca gaatccaaaa acaacaagaa aggatcaatg ggatattgtg catatctaag    2820
tagattcagt gttctctcct gaatagcgtt acatagtgtg acaggcacac cattggccac    2880
tgactgatca atgatagtgt caatagtttc agctaattga tgtggctcct tacacttaac    2940
gttgtggagg gcggcagcca cgaatttcgt taacaatgga acttcatcac cccagacata    3000
aaaccttgat ttgaactcag caacaaatga accaataaca ctctttggac tgatgaattt    3060
attcaattga tcacttagga aatagtgaaa ttctagaatg gcttggaatt cctcaggctc    3120
atttgagagt aaatctgaaa gatccttgcc aaatagtgat atttgatcat cactagaggt    3180
atatgaatca acttcatctt caaatagaca cttaatgcaa taatttatga atctctcact    3240
cactagaccg tagaagtcag aagcattgtg caagatccct tgccccatgt caattattga    3300
gctgagatgt gatggtatcc tgttttgttt aaagtattca aagaagaaag cttctgttga    3360
cgtttggtgg agtgattttt tcaaacctaa cctagactta agataagatc tcatcattgc    3420
attcacaaca ttgaaaggta cctcaattaa cttgtgaatg tgccacgaca gcaaagtgga    3480
cacgtaatcc ttacttttta tgtcctctat atcatctcct gtctcccatc gcaaattttg    3540
aagaaacacc aggaaaagaa aagggggacat cataggcccc cacttgctgt gatcgaggct    3600
ataagagacc tgacctagtg aaacattcaa tttcatggct agaatggcat tgtggaattc    3660
cttttcatta ttaagacagc tccctctata ttgcttagtt agtgcctcaa aataatcctc    3720
aattaggcgt gtgaacattt ttgtcctcag gtcacctata taaagttccc tgttccctcc    3780
```

```
aacttgttct tgtaagata aggaaaactt gagccttcca gtatcaggac ccaaggatgt   3840
gtatgactgt ggggattctt gactgtaaaa acataggttc tttagaactg cagttgtaca   3900
atttgtcaat gacagtgctt tacctaatgc ctcagaattg ctctctcttt cactgatcct   3960
aacatcattc atcagccttt ctctatcaat cttgaagttt aagcatttgt ttttgtaatg   4020
gctgtatttt ccagccaatt tccctgcatt catctgaaga agtagtgact gaagcactg    4080 aaaaaactgc tggtcattga atgttctggt ggagacagct tgggtgatgc atgttattgg   4140
gcaagagtcc aaggaatcca aatagaaata ctttgacctt aactccaaat ccttaaaaaa   4200
gcctttgcag atcatctcat aagcatctcc aggtagtagt gactcatcaa aatcttccac   4260
catgtggtgt gctatctctg cctggatcag tctgtagtaa acacagccca catcttcagt   4320
acctaaaacc ttcctcaagt ctgtcaagga cttctcctct gacccatttc ccacagggaa   4380
cttcctgtca tatctatact ctcaaggac gacatcaaca gatttcttca catcctctag    4440
acagtcaagt gcacaactat ccaagaataa ctcatctaat tcgtcaggag ccccttgtga   4500
attgggattt gaggaacctg acttcttccc cacaacaagg tcactaatgg ccttttgcac   4560
cttataatca taatcctcct tactcaagag gtatttagtt ttcctctgga atacctctga   4620
tagctggcaa acagaagcag ccactagttt atcatgatcg taattaagta tcctctctcc   4680
gtcagtatac ttattcacaa ccacacttt gttgcttgca aggtcaagag ctgttgcaca   4740
cccagcagta actaatggat cttaaaccc acttaggtca tctcctttct tgaaaagaga    4800
gccattgtta aaagaagacg tcatcattga gaagaatttt cttgacacac caggaacttt   4860
ataagatatt ctgttgttac tcatactggt ttctttggat aaaaatttgt ttgctgattc   4920
aagcagcagc atcctttcat cttcatcccc ctcttcagat gggttgatgt taatactgtc   4980
aaactccaac ttgggctcca atacttctc aaagcactta atctgatctg tcaacctatc    5040
tggagtttcc ttagttataa aatgacacat gtatgatagg tttaacacaa acttaaatct   5100
attagtcaac atagtgctca ccccttcacc caggatgatg ttgagaatgc tcctcaccac   5160
actatacaag aggtgctccg gctctgttat gagatcctcc ctcaacttt ccattaactg    5220 cttatggtgg aagtctgaaa caaaggccat tatgaagtat cgcagacctt gcaagaactt   5280
ctgtgctctt tgctagggt tcacaagtat gaggatcatg gtgattttga gcaataattt    5340 taaagtttt tgttgatctc tgagttctat acattcagac aaccaactca tcatggtgtt    5400
gatagtctca tagataacac agtgtgagaa aattgcagga aaaaccttt ttggatctgc    5460 atagaatgaa caaatctccc ccttctcagg attgttaatg gcataacatt ttgagcactc   5520
tcctgttttc tgataaatta agttgaaatt cccgcttccc atgataaagc tttgattaaa   5580
agcttcctta caacgtacac gtttgtacct tgcagcacca tactcatttt gcctcacttt   5640
ggctactgat gatgtcttca ttgaattcac caatgccaaa gagatgctag atagtcttct   5700
caggtcttct atggaatcag cttccaactc aataagaggg taggggaatt gattcccctc   5760
ttctttctca tagctcattg ttggctgaat ccctcttttc tccattaaca taagcctctc   5820
gtaactgtcc tcctccagta tatcttcctc tttaacataa tctctaaagc acaaactggc   5880
agaggataat gcctctttgg cctttgtgag gagtttgttt atgatgtcaa agaatataag   5940
ctcagatctc tgacacagag ttcctacacc tcccttcttc ttcattgcac tcaccattct   6000
cctttcaatc cactttttaa ggtccttttg tgtttcttgt agtgacacca atctgtcgtt   6060
cacacttaag aatgaggagc caagccattc tgatcctaac agctcgccgt gacatttaag   6120
```

-continued

```
atcctttaag tgggccaaaa ggatgattgc gtcaaaagtc agcattagtt ttcttctggt    6180
gttcaataac tttagtgatt ttattttatt caacagtgac ttccatccag gcacagagct    6240
ttggaagtga ttctgcaagc agctgtctcg atcaactccc tcttgcctat aacggtcgta    6300
gtcaccatag agcgctgtta ccataggcga ggattttaca aacctctctt ttagaggatc    6360
aatctctgag ggtgtgtccc cctctctgtc aatataaagg ttgttgaaat ctctcaagag    6420
ctgtcgccta tctgtcctga caaattgtct ttctatctca ccctctttaa gcttattcct    6480
aaaagcatga aattctgata caatctcttt tttcacatca agaatggaca ttttgttatt    6540
gatgcctctg tggcagagct ccaacaccct ctcataatga tcagatcgag aatctgtcaa    6600
aacattgagg ctctcaatgc ccgatgttct cactcctgct tttgttaaag attcacaaag    6660
ccttgagtac tcagattctt caaacatttt tgatgactgc tgcgagaatt caagtaagct    6720
aaataggata tgcctaaacc tctcattggc ccattctgga aacaaatcag tgtagaaatt    6780
ggttctgccg tctatcaagg gcaacagaat gatgtcaaca gatgataagt caggctttaa    6840
agactctagc ttaatggtat cttctttata cttttgctca aagtttattg gtgaagtcct    6900
gacaaagcat tccagtaata ttaatgtgtt cccactgaat ttgaatccat ctggcaccac    6960
aaatggtaga ccagggcaca gaacaccttg tctctgcaga aggatttcaa cagaaaggtc    7020
ttctgagttg tgctcacaac cattggcttt gcaactgtct atctcaatac agagtgacaa    7080
caacttaagg ccctcaatta atagcattct cggctctgtc tgaactagga aggctagctt    7140
ctgttttgaa agcctctcat cctctaagag gtacctgctc acaagatctt gctctcgga     7200
cagcaactcc tccatcacca cacacttgtt cctcagaaga gagagtcaca atgcctagga    7260
tcctcggtgc gtggggaaaa cgcagtccaa gggacagccc agcacaaatc tcctcaagga    7320
gacagaacca aggcatccag taataccaga tgccagggga actggccctg aattctgcaa    7380
gagctgctgg ttcgaaagga gggggttagt caggtgcaac gatcactacc tatgtttgaa    7440
ctgtcttaca cttttacaca cagtgtcaga taggtgcccc atctgcaaac acaaactacc    7500
cttcagacta gagctccaga cccagccgac agcaccacca gaaatcccac catcccaaaa    7560
tcccccaccc tacagcccct gaggcagaac tccgccccga agcccctccc aaacacccct    7620
cccctccccc ccgggggac ccccgccgg ggctccccc ggggggagat gcgcgagctg       7680
ttctcggagc acctactcaa tgtcgagggg aggcccacc tcttcaaaga ggggcctgca     7740
cagcctccct cttaatctaa acttcccctc tgaagactgg atcatcagtg aagcctgcga    7800
tctactgtag cagagactat agcctttaaa atctgcccag aagtcaattc cggagaacac    7860
tctagtaagg aagttttcgt agccttcagg catgcatcgt cccacaaccc ctataatatc    7920
aagttgtagc cagtgtagtc cttggtccat tctggatctc agcatcttgc tcaaagatct    7980
ctccaagatt tcggaatgat cctccattag ctcaccaata aaacattaa gatcctggtc     8040
atggatgttg gggttgaagg gcaggagttt cctggtccct tcaataaggt atcctgagtc    8100
aacaactaag gggatttcaa catgctcagg ccctatatgc gtgaaatcat gttcctccag    8160
gtccaggatc tcctcattca ataagacgga caagggtatc acatcaggaa tgggggaact    8220
atccctcaag tagtcacaaa tattttcagt ggacagcaac caaattgatg tggtttccct    8280
tttaaaccat gtagatgtct gtgcaactct ccagcaatct ttaattgcgg atctttgaac    8340
actaccactg taagttacat caagggaatg aggcttgaat aatccacctt ccaacaccac    8400
cccctttgaaa aggaggtgga gactaaattt ctctttcaat gattcaccct gacttctcac    8460
ctgaaaattt actgtgacag aaatttgaac gctcccaaca ctgaggtcgg caaaagcttc    8520
```

```
aagcagctca cttaccgact caaagacgtg ctgctcggtt aatcctgatg ctatgagctg   8580
tcctaagttt agaattgctg gtgcacattc aaaatccagc caagcataac ctgagtaaag   8640
atcatgcctg tacatgggtc tttcaacacc cttataaata accttttcta taaaagaaga   8700
aaaggggccg aggttgtcaa gcccttccga ctcaggaatt gaagatctat gtggaaacca   8760
agtaaaagaa cctaaagtcc tgcttgttgc aacgaatggt ctgatgaagg actcaaagta   8820
gatttgtctc aggaaatttt gtaccacatc ataagtggtc caccccttt catccgtgat   8880 tgggagatga gacctctcat gtgctattgc taaatctgaa gacagaacca cataatgctc   8940
ttctctcttc cacttgacaa catgagaaat taatgacatt gcctcacaat tcacatctag   9000
aaccacacaa agatcaagaa acttaatcct tggtgtccac ctcattttcg ttgatgctag   9060
gtcactcatg aagggcaaga ggtgtctctc aaatagagat gggtaaagtc ttctgaatga   9120
gtgaataata tggttaaacc ccaccttgtc ttccaagagt tttgtggtag tgggcttcat   9180
tgggaaatag tcacatggct tgaagggaat tgaggatgt ttctccttca ctttgggttc   9240
acccaacacc caggaaccca gctcaagtga tgtagataag gctatgcaga agtaatccca   9300
aaggacaggt ctcaagaaac ctaacgcttc ctcagctgcc tttgtgtgct ccttacccaa   9360
gatccaaaga tcgacgccct taactttcaa gctggaaaca gaatccaatg ctgacagtct   9420
tgaaactaat gatttatat aggcggtgga cctatctgag aatcgaacac atttgctacc    9480
tagtgtcttg caaagaccta tgaaacctga tgctatccca ctctgaaagg cacttttgtt   9540
gacggcttca cagagcaact tttgtgcccc tcttgtgaaa ttagaggata acttgctttg   9600
caatgttttc accaaggtag gcagtttttc ttccccgagt tcaacagcac ctgtgtaaat   9660
gaccttctgt ctcatgacca tctttaaagg gtgatgagtt gtcaaattaa gccaacacac   9720
cgataaatcc tcttctgaga gggtgtcatc accaacaagg ctggtaagtt tcttgaagga   9780
atctgcgggg tctcctgaca agtagatggc tgtgaattct tcatgaagct ctcctaattt   9840
cagcttatta aaaactgtcc ttaggacctt cctaactttc tgagtgcttt ctggtaggat   9900
tgcctcaatg ttcctcataa tcctatagcc cctattgcca tcaacccaat ctttaacatc   9960
agaatccaaa acaacaaga aaggatcaat gggatattgt gcatatctaa gtagattcag    10020
tgttctctcc tgaatagcgt tacatagtgt gacaggcaca ccattggcca ctgactgatc   10080
aatgatagtg tcaatagttt cagctaattg atgtggctcc ttacacttaa cgttgtggag   10140
ggcggcagcc acgaatttcg ttaacaatgg aacttcatca ccccagacat aaaaccttga   10200
tttgaactca gcaacaaatg aaccaataac actctttgga ctgatgaatt tattcaattg   10260
atcacttagg aaatagtgaa attctagaat ggcttggaat tcctcaggct catttgagag   10320
taaatctgaa agatccttgc caaatagtga tatttgatca tcactagagg tatatgaatc   10380
aacttcatct tcaaatagac acttaatgca ataatttatg aatctctcac tcactagacc   10440
gtagaagtca gaagcattgt gcaagatccc ttgccccatg tcaattattg agctgagatg   10500
tgatggtatc ctgttttgtt taaagtattc aaagaagaaa gcttctgttg acgtttggtg   10560
gagtgatttt ttcaaaccta acctagactt aagataagat ctcatcattg cattcacaac   10620
attgaaaggt acctcaatta acttgtgaat gtgccacgac agcaaagtgg acacgtaatc   10680
cttacttttt atgtcctcta tatcatctcc tgtctcccat cgcaaatttt gaagaaacac   10740
caggaaaaga aaagggggaca tcataggccc ccacttgctg tgatcgaggc tataagagac   10800
ctgacctagt gaaacattca atttcatggc tagaatggca ttgtggaatt ccttttcatt   10860
```

```
attaagacag ctccctctat attgcttagt tagtgcctca aaataatcct caattaggcg   10920
tgtgaacatt tttgtcctca ggtcacctat ataaagttcc ctgttccctc caacttgttc   10980
tttgtaagat aaggaaaact tgagccttcc agtatcagga cccaaggatg tgtatgactg   11040
tggggattct tgactgtaaa aacataggtt ctttagaact gcagttgtac aatttgtcaa   11100
tgacagtgct ttacctaatg cctcagaatt gctctctctt tcactgatcc taacatcatt   11160
catcagcctt tctctatcaa tcttgaagtt taagcatttg tttttgtaat ggctgtattt   11220
tccagccaat ttccctgcat tcatctgaag aagtagtgac ttgaagcact gaaaaaactg   11280
ctggtcattg aatgttctgg tggagacagc ttgggtgatg catgttattg ggcaagagtc   11340
caaggaatcc aaatagaaat actttgacct taactccaaa tccttaaaaa agcctttgca   11400
gatcatctca taagcatctc caggtagtag tgactcatca aaatcttcca ccatgtggtg   11460
tgctatctct gcctggatca gtctgtagta aacacagccc acatcttcag tacctaaaac   11520
cttcctcaag tctgtcaagg acttctcctc tgacccattt cccacaggga acttcctgtc   11580
atatctatac ttctcaagga cgacatcaac agatttcttc acatcctcta gacagtcaag   11640
tgcacaacta ccaagaata  actcatctaa ttcgtcagga gccccttgtg aattgggatt   11700
tgaggaacct gacttcttcc ccacaacaag gtcactaatg ccttttgca  ccttataatc   11760
ataatcctcc ttactcaaga ggtatttagt tttcctctgg aatacctctg atagctggca   11820
aacagaagca gccactagtt tatcatgatc gtaattaagt atcctctctc cgtcagtata   11880
cttattcaca accacacttt tgttgcttgc aaggtcaaga gctgttgcac acccagcagt   11940
aactaatgga tctttaaacc cacttaggtc atctcctttc ttgaaaagag agccattgtt   12000
aaaagaagac gtcatcattg agaagaattt tcttgacaca ccaggaactt tataagatat   12060
tctgttgtta ctcatactgg tttctttgga taaaaatttg tttgctgatt caagcagcag   12120
catcctttca tcttcatccc cctcttcaga tgggttgatg ttaatactgt caaactccaa   12180
cttgggctcc aaatacttct caaagcactt aatctgatct gtcaacctat ctggagtttc   12240
cttagttata aaatgacaca tgtatgatag gtttaacaca aacttaaatc tattagtcaa   12300
catagtgctc acccccttcac ccaggatgat gttgagaatg ctcctcacca cactatacaa   12360
gaggtgctcc ggctctgtta tgagatcctc cctcaacttt tccattaact gcttatggtg   12420
gaagtctgaa acaaaggcca ttatgaagta tcgcagacct tgcaagaact tctgtgctct   12480
tttgctaggg ttcacaagta tgaggatcat ggtgattttg agcaataatt ttaaagtttt   12540
ttgttgatct ctgagttcta tacattcaga caaccaactc atcatggtgt tgatagtctc   12600
atagataaca cagtgtgaga aaattgcagg aaaaaaccct tttggatctg catagaatga   12660
acaaatctcc cccttctcag gattgttaat ggcataacat tttgagcact ctcctgtttt   12720
ctgataaatt aagttgaaat tcccgcttcc catgataaag ctttgattaa aagcttcctt   12780
acaacgtaca cgtttgtacc ttgcagcacc atactcattt tgcctcactt tggctactga   12840
tgatgtcttc attgaattca ccaatgccaa agagatgcta gatagtcttc tcaggtcttc   12900
tatggaatca gcttccaact caataagagg gtagggaat  tgattcccct cttctttctc   12960
atagctcatt gttggctgaa tccctctttt ctccattaac ataagcctct cgtaactgtc   13020
ctcctccagt atatcttcct cttaacata  atctctaaag cacaaactgg cagaggataa   13080
tgcctctttg gccttgtga  ggagtttgtt tatgatgtca aagaatataa gctcagatct   13140
ctgacacaga gttcctacac ctcccttctt cttcattgca ctcaccattc tcctttcaat   13200
ccactttta  aggtcctttt gtgtttcttg tagtgacacc aatctgtcgt tcacacttaa   13260
```

-continued

```
gaatgaggag ccaagccatt ctgatcctaa cagctcgccg tgacatttaa gatcctttaa  13320
gtgggccaaa aggatgattg cgtcaaaagt cagcattagt tttcttctgg tgttcaataa  13380
ctttagtgat tttattttat tcaacagtga cttccatcca ggcacagagc tttggaagtg  13440
attctgcaag cagctgtctc gatcaactcc ctcttgccta taacggtcgt agtcaccata  13500
gagcgctgtt accataggcg aggattttac aaacctctct tttagaggat caatctctga  13560
gggtgtgtcc ccctctctgt caatataaag gttgttgaaa tctctcaaga gctgtcgcct  13620
atctgtcctg acaaattgtc tttctatctc accctcttta agcttattcc taaaagcatg  13680
aaattctgat acaatctctt ttttcacatc aagaatggac atttttgttat tgatgcctct  13740 gtggcagagc tccaacaccc tctcataatg atcagatcga aatctgtcaa aacattgag  13800 gctctcaatg cccgatgttc tcactcctgc ttttgttaaa gattcacaaa gccttgagta  13860
ctcagattct tcaaacattt ttgatgactg ctgcgagaat tcaagtaagc taaataggat  13920
atgcctaaac ctctcattgg cccattctgg aaacaaatca gtgtagaaat tggttctgcc  13980
gtctatcaag ggcaacagaa tgatgtcaac agatgataag tcaggcttta aagactctag  14040
cttaatggta tcttctttat acttttgctc aaagtttatt ggtgaagtcc tgacaaagca  14100
ttccagtaat attaatgtgt tcccactgaa tttgaatcca tctggcacca caatggtag   14160 accagggcac agaacacctt gtctctgcag aaggatttca acagaaaggt cttctgagtt  14220
gtgctcacaa ccattggctt tgcaactgtc tatctcaata cagagtgaca caacttaag   14280 gccctcaatt aatagcattc tcggctctgt ctgaactagg aaggctagct tctgttttga  14340
aagcctctca tcctctaaga ggtacctgct cacaagatct ttgctctcgg acagcaactc  14400
ctccatcacc acacacttgt tcctcagaag agagagtcac aatgcctagg atcctcggtg  14460
cg                                                                14462
```

<210> SEQ ID NO 3
<211> LENGTH: 489
<212> TYPE: PRT
<213> ORGANISM: Mopeia mammarenavirus

<400> SEQUENCE: 3

```
Met Gly Gln Ile Val Thr Phe Phe Gln Glu Val Pro His Ile Leu Glu
1               5                   10                  15

Glu Val Met Asn Ile Val Leu Met Thr Leu Ser Ile Leu Ala Ile Leu
                20                  25                  30

Lys Gly Ile Tyr Asn Val Met Thr Cys Gly Ile Gly Leu Ile Thr
            35                  40                  45

Phe Leu Phe Leu Cys Gly Arg Ser Cys Ser Ser Ile Tyr Lys Asp Asn
        50                  55                  60

Tyr Glu Phe Phe Ser Leu Asp Leu Asp Met Ser Ser Leu Asn Ala Thr
65                  70                  75                  80

Met Pro Leu Ser Cys Ser Lys Asn Asn Ser His His Tyr Ile Gln Val
                85                  90                  95

Gly Asn Glu Thr Gly Leu Glu Leu Thr Leu Thr Asn Thr Ser Ile Ile
                100                 105                 110

Asp His Lys Phe Cys Asn Leu Ser Asp Ala His Arg Arg Asn Leu Tyr
            115                 120                 125

Asp Lys Ala Leu Met Ser Ile Leu Thr Thr Phe His Leu Ser Ile Pro
        130                 135                 140

Asp Phe Asn Gln Tyr Glu Ala Met Ser Cys Asp Phe Asn Gly Gly Lys
```

```
            145                 150                 155                 160
        Ile Ser Ile Gln Tyr Asn Leu Ser His Ser Asn Tyr Val Asp Ala Gly
                        165                 170                 175

Asn His Cys Gly Thr Ile Ala Asn Gly Ile Met Asp Val Phe Arg Arg
                        180                 185                 190

Met Tyr Trp Ser Thr Ser Leu Ser Val Ala Ser Asp Ile Ser Gly Thr
                        195                 200                 205

Gln Cys Ile Gln Thr Asp Tyr Lys Tyr Leu Ile Ile Gln Asn Thr Ser
                        210                 215                 220

Trp Glu Asp His Cys Met Phe Ser Arg Pro Ser Pro Met Gly Phe Leu
        225                 230                 235                 240

Ser Leu Leu Ser Gln Arg Thr Arg Asn Phe Tyr Ile Ser Arg Arg Leu
                        245                 250                 255

Leu Gly Leu Phe Thr Trp Thr Leu Ser Asp Ser Glu Gly Asn Asp Met
                        260                 265                 270

Pro Gly Gly Tyr Cys Leu Thr Arg Ser Met Leu Ile Gly Leu Asp Leu
                        275                 280                 285

Lys Cys Phe Gly Asn Thr Ala Ile Ala Lys Cys Asn Gln Ala His Asp
                        290                 295                 300

Glu Glu Phe Cys Asp Met Leu Arg Leu Phe Asp Phe Asn Lys Gln Ala
        305                 310                 315                 320

Ile Ser Lys Leu Arg Ser Glu Val Gln Gln Ser Ile Asn Leu Ile Asn
                        325                 330                 335

Lys Ala Val Asn Ala Leu Ile Asn Asp Gln Leu Val Met Arg Asn His
                        340                 345                 350

Leu Arg Asp Leu Met Gly Ile Pro Tyr Cys Asn Tyr Ser Lys Phe Trp
                        355                 360                 365

Tyr Leu Asn Asp Thr Arg Thr Gly Arg Thr Ser Leu Pro Lys Cys Trp
                        370                 375                 380

Leu Val Thr Asn Gly Ser Tyr Leu Asn Glu Thr Gln Phe Ser Thr Glu
        385                 390                 395                 400

Ile Glu Gln Glu Ala Asn Asn Met Phe Thr Asp Met Leu Arg Lys Glu
                        405                 410                 415

Tyr Glu Lys Arg Gln Ser Thr Thr Pro Leu Gly Leu Val Asp Leu Phe
                        420                 425                 430

Val Phe Ser Thr Ser Phe Tyr Leu Ile Ser Val Phe Leu His Leu Ile
                        435                 440                 445

Lys Ile Pro Thr His Arg His Ile Lys Gly Lys Pro Cys Pro Lys Pro
                        450                 455                 460

His Arg Leu Asn His Met Ala Ile Cys Ser Cys Gly Phe Tyr Lys Gln
        465                 470                 475                 480

Pro Gly Leu Pro Thr Gln Trp Lys Arg
                        485

<210> SEQ ID NO 4
<211> LENGTH: 570
<212> TYPE: PRT
<213> ORGANISM: Mopeia mammarenavirus

<400> SEQUENCE: 4

Met Ser Asn Ser Lys Glu Val Lys Ser Phe Leu Trp Thr Gln Ser Leu
1               5                   10                  15

Arg Arg Glu Leu Ser Gly Tyr Cys Ser Asn Ile Lys Ile Gln Val Ile
                20                  25                  30
```

-continued

```
Lys Asp Ala Gln Ala Leu Leu His Gly Leu Asp Phe Ser Glu Val Ala
             35                  40                  45

Asn Val Gln Arg Leu Met Arg Lys Glu Lys Arg Asp Asp Ser Asp Leu
 50                  55                  60

Lys Arg Leu Arg Asp Leu Asn Gln Ala Val Asn Asn Leu Val Glu Leu
 65                  70                  75                  80

Lys Ser Val Gln Gln Lys Asn Val Leu Arg Val Gly Thr Leu Thr Ser
                 85                  90                  95

Asp Asp Leu Leu Val Leu Ala Ala Asp Leu Asp Arg Leu Lys Ala Lys
                100                 105                 110

Val Ile Arg Gly Glu Arg Pro Leu Ala Ala Gly Val Tyr Met Gly Asn
             115                 120                 125

Leu Thr Ala Gln Gln Leu Glu Gln Arg Arg Val Leu Leu Gln Met Val
         130                 135                 140

Gly Met Gly Gly Gly Phe Arg Ala Gly Asn Thr Leu Gly Asp Gly Ile
145                 150                 155                 160

Val Arg Val Trp Asp Val Arg Asn Pro Glu Leu Leu Asn Asn Gln Phe
                 165                 170                 175

Gly Thr Met Pro Ser Leu Thr Ile Ala Cys Met Cys Lys Gln Gly Gln
             180                 185                 190

Ala Asp Leu Asn Asp Val Ile Gln Ser Leu Ser Asp Leu Gly Leu Val
         195                 200                 205

Tyr Thr Ala Lys Tyr Pro Asn Met Ser Asp Leu Asp Lys Leu Ser Gln
    210                 215                 220

Thr His Pro Ile Leu Gly Ile Ile Glu Pro Lys Lys Ser Ala Ile Asn
225                 230                 235                 240

Ile Ser Gly Tyr Asn Phe Ser Leu Ser Ala Val Lys Ala Gly Ala
                 245                 250                 255

Cys Leu Ile Asp Gly Gly Asn Met Leu Glu Thr Ile Lys Val Thr Lys
             260                 265                 270

Ser Asn Leu Glu Gly Ile Leu Lys Ala Ala Leu Lys Val Lys Arg Ser
         275                 280                 285

Leu Gly Met Phe Val Ser Asp Thr Pro Gly Glu Arg Asn Pro Tyr Glu
    290                 295                 300

Asn Leu Leu Tyr Lys Leu Cys Leu Ser Gly Glu Gly Trp Pro Tyr Ile
305                 310                 315                 320

Ala Ser Arg Thr Ser Ile Val Gly Arg Ala Trp Asp Asn Thr Thr Val
                 325                 330                 335

Asp Leu Ser Gly Asp Val Gln Gln Asn Ala Lys Pro Asp Lys Gly Asn
             340                 345                 350

Ser Asn Arg Leu Ala Gln Ala Gln Gly Met Pro Ala Gly Leu Thr Tyr
         355                 360                 365

Ser Gln Thr Met Glu Leu Lys Asp Ser Met Leu Gln Leu Asp Pro Asn
    370                 375                 380

Ala Lys Thr Trp Ile Asp Ile Glu Gly Arg Pro Glu Asp Pro Val Glu
385                 390                 395                 400

Ile Ala Ile Tyr Gln Pro Asn Asn Gly Gln Tyr Ile His Phe Tyr Arg
                 405                 410                 415

Glu Pro Thr Asp Ile Lys Gln Phe Lys Gln Asp Ser Lys His Ser His
             420                 425                 430

Gly Ile Asp Ile Gln Asp Leu Phe Ser Val Gln Pro Gly Leu Thr Ser
         435                 440                 445

Ala Val Ile Glu Ser Leu Pro Lys Asn Met Val Leu Ser Cys Gln Gly
```

```
                450              455              460
Ala Asp Asp Ile Arg Lys Leu Leu Asp Ser Gln Asn Arg Arg Asp Ile
465                  470                  475                  480

Lys Leu Ile Asp Val Ser Met Gln Lys Asp Ala Arg Lys Phe Glu
                485                  490                  495

Asp Lys Ile Trp Asp Glu Tyr Lys His Leu Cys Arg Met His Thr Gly
                500                  505                  510

Ile Val Thr Gln Lys Lys Arg Gly Gly Lys Glu Glu Val Thr Pro
                515                  520                  525

His Cys Ala Leu Leu Asp Cys Leu Met Phe Glu Ala Ala Val Ile Gly
                530                  535                  540

Ser Pro Gln Ile Pro Thr Pro Arg Pro Val Leu Ser Arg Asp Leu Val
545                  550                  555                  560

Phe Arg Thr Gly Pro Pro Arg Val Val Leu
                565                  570

<210> SEQ ID NO 5
<211> LENGTH: 103
<212> TYPE: PRT
<213> ORGANISM: Mopeia mammarenavirus

<400> SEQUENCE: 5

Met Gly Lys Thr Gln Ser Lys Gly Gln Pro Ser Thr Asn Leu Leu Lys
1               5                   10                  15

Glu Thr Glu Pro Arg His Pro Val Ile Pro Asp Ala Arg Gly Thr Gly
                20                  25                  30

Pro Glu Phe Cys Lys Ser Cys Trp Phe Glu Arg Arg Gly Leu Val Arg
            35                  40                  45

Cys Asn Asp His Tyr Leu Cys Leu Asn Cys Leu Thr Leu Leu His Thr
50                  55                  60

Val Ser Asp Arg Cys Pro Ile Cys Lys His Lys Leu Pro Phe Arg Leu
65                  70                  75                  80

Glu Leu Gln Thr Gln Pro Thr Ala Pro Pro Glu Ile Pro Pro Ser Gln
                85                  90                  95

Asn Pro Pro Pro Tyr Ser Pro
            100

<210> SEQ ID NO 6
<211> LENGTH: 2237
<212> TYPE: PRT
<213> ORGANISM: Mopeia mammarenavirus

<400> SEQUENCE: 6

Met Glu Glu Leu Leu Ser Glu Ser Lys Asp Leu Val Ser Arg Tyr Leu
1               5                   10                  15

Leu Glu Asp Glu Arg Leu Ser Lys Gln Lys Leu Ala Phe Leu Val Gln
                20                  25                  30

Thr Glu Pro Arg Met Leu Leu Ile Glu Gly Leu Lys Leu Leu Ser Leu
                35                  40                  45

Cys Ile Glu Ile Asp Ser Cys Lys Ala Asn Gly Cys Glu His Asn Ser
50                  55                  60

Glu Asp Leu Ser Val Glu Ile Leu Leu Gln Arg Gln Gly Val Leu Cys
65                  70                  75                  80

Pro Gly Leu Pro Phe Val Val Pro Asp Gly Phe Lys Phe Ser Gly Asn
                85                  90                  95

Thr Leu Ile Leu Leu Glu Cys Phe Val Arg Thr Ser Pro Ile Asn Phe
```

```
                100              105               110
Glu Gln Lys Tyr Lys Glu Asp Thr Ile Lys Leu Glu Ser Leu Lys Pro
            115                 120             125

Asp Leu Ser Ser Val Asp Ile Ile Leu Leu Pro Leu Ile Asp Gly Arg
130             135                 140

Thr Asn Phe Tyr Thr Asp Leu Phe Pro Glu Trp Ala Asn Glu Arg Phe
145                 150             155                 160

Arg His Ile Leu Phe Ser Leu Leu Glu Phe Ser Gln Gln Ser Ser Lys
                165             170             175

Met Phe Glu Glu Ser Glu Tyr Ser Arg Leu Cys Glu Ser Leu Thr Lys
            180             185             190

Ala Gly Val Arg Thr Ser Gly Ile Glu Ser Leu Asn Val Leu Thr Asp
        195             200             205

Ser Arg Ser Asp His Tyr Glu Arg Val Leu Glu Leu Cys His Arg Gly
    210             215             220

Ile Asn Asn Lys Met Ser Ile Leu Asp Val Lys Lys Glu Ile Val Ser
225             230             235             240

Glu Phe His Ala Phe Arg Asn Lys Leu Lys Glu Gly Glu Ile Glu Arg
                245             250             255

Gln Phe Val Arg Thr Asp Arg Arg Gln Leu Leu Arg Asp Phe Asn Asn
            260             265             270

Leu Tyr Ile Asp Arg Glu Gly Asp Thr Pro Ser Glu Ile Asp Pro Leu
        275             280             285

Lys Glu Arg Phe Val Lys Ser Ser Pro Met Val Thr Ala Leu Tyr Gly
    290             295             300

Asp Tyr Asp Arg Tyr Arg Gln Glu Gly Val Asp Arg Asp Ser Cys Leu
305             310             315             320

Gln Asn His Phe Gln Ser Ser Val Pro Gly Trp Lys Ser Leu Leu Asn
                325             330             335

Lys Ile Lys Ser Leu Lys Leu Leu Asn Thr Arg Arg Lys Leu Met Leu
            340             345             350

Thr Phe Asp Ala Ile Ile Leu Leu Ala His Leu Lys Asp Leu Lys Cys
        355             360             365

His Gly Glu Leu Leu Gly Ser Glu Trp Leu Gly Ser Ser Phe Leu Ser
    370             375             380

Val Asn Asp Arg Leu Val Ser Leu Gln Glu Thr Gln Lys Asp Leu Lys
385             390             395             400

Lys Trp Ile Glu Arg Arg Met Val Ser Ala Met Lys Lys Gly Gly
                405             410             415

Val Gly Thr Leu Cys Gln Arg Ser Glu Leu Ile Phe Phe Asp Ile Ile
            420             425             430

Asn Lys Leu Leu Thr Lys Ala Lys Glu Ala Leu Ser Ser Ala Ser Leu
        435             440             445

Cys Phe Arg Asp Tyr Val Lys Glu Glu Asp Ile Leu Glu Glu Asp Ser
    450             455             460

Tyr Glu Arg Leu Met Leu Met Glu Lys Arg Gly Ile Gln Pro Thr Met
465             470             475             480

Ser Tyr Glu Lys Glu Glu Gly Asn Gln Phe Pro Tyr Pro Leu Ile Glu
                485             490             495

Leu Glu Ala Asp Ser Ile Glu Asp Leu Arg Arg Leu Ser Ser Ile Ser
            500             505             510

Leu Ala Leu Val Asn Ser Met Lys Thr Ser Ser Val Ala Lys Val Arg
        515             520             525
```

```
Gln Asn Glu Tyr Gly Ala Ala Arg Tyr Lys Arg Val Arg Cys Lys Glu
        530                 535                 540

Ala Phe Asn Gln Ser Phe Ile Met Gly Ser Gly Asn Phe Asn Leu Ile
545                 550                 555                 560

Tyr Gln Lys Thr Gly Glu Cys Ser Lys Cys Tyr Ala Ile Asn Asn Pro
                565                 570                 575

Glu Lys Gly Glu Ile Cys Ser Phe Tyr Ala Asp Pro Lys Arg Phe Phe
                580                 585                 590

Pro Ala Ile Phe Ser His Cys Val Ile Tyr Glu Thr Ile Asn Thr Met
                595                 600                 605

Met Ser Trp Leu Ser Glu Cys Ile Glu Leu Arg Asp Gln Gln Lys Thr
        610                 615                 620

Leu Lys Leu Leu Leu Lys Ile Thr Met Ile Leu Ile Leu Val Asn Pro
625                 630                 635                 640

Ser Lys Arg Ala Gln Lys Phe Leu Gln Gly Leu Arg Tyr Phe Ile Met
                645                 650                 655

Ala Phe Val Ser Asp Phe His His Lys Gln Leu Met Glu Lys Leu Arg
                660                 665                 670

Glu Asp Leu Ile Thr Glu Pro Glu His Leu Leu Tyr Ser Val Val Arg
                675                 680                 685

Ser Ile Leu Asn Ile Ile Leu Gly Glu Gly Val Ser Thr Met Leu Thr
                690                 695                 700

Asn Arg Phe Lys Phe Val Leu Asn Leu Ser Tyr Met Cys His Phe Ile
705                 710                 715                 720

Thr Lys Glu Thr Pro Asp Arg Leu Thr Asp Gln Ile Lys Cys Phe Glu
                725                 730                 735

Lys Tyr Leu Glu Pro Lys Leu Glu Phe Asp Ser Ile Asn Ile Asn Pro
                740                 745                 750

Ser Glu Glu Gly Asp Glu Asp Glu Arg Met Leu Leu Leu Glu Ser Ala
                755                 760                 765

Asn Lys Phe Leu Ser Lys Glu Thr Ser Met Ser Asn Asn Arg Ile Ser
770                 775                 780

Tyr Lys Val Pro Gly Val Ser Arg Lys Phe Phe Ser Met Met Thr Ser
785                 790                 795                 800

Ser Phe Asn Asn Gly Ser Leu Phe Lys Lys Gly Asp Asp Leu Ser Gly
                805                 810                 815

Phe Lys Asp Pro Leu Val Thr Ala Gly Cys Ala Thr Ala Leu Asp Leu
                820                 825                 830

Ala Ser Asn Lys Ser Val Val Asn Lys Tyr Thr Asp Gly Glu Arg
                835                 840                 845

Ile Leu Asn Tyr Asp His Asp Lys Leu Val Ala Ala Ser Val Cys Gln
850                 855                 860

Leu Ser Glu Val Phe Gln Arg Lys Thr Lys Tyr Leu Leu Ser Lys Glu
865                 870                 875                 880

Asp Tyr Asp Tyr Lys Val Gln Lys Ala Ile Ser Asp Leu Val Val Gly
                885                 890                 895

Lys Lys Ser Gly Ser Ser Asn Pro Asn Ser Gln Gly Ala Pro Asp Glu
                900                 905                 910

Leu Asp Glu Leu Phe Leu Asp Ser Cys Ala Leu Asp Cys Leu Glu Asp
                915                 920                 925

Val Lys Lys Ser Val Asp Val Leu Glu Lys Tyr Arg Tyr Asp Arg
930                 935                 940
```

-continued

```
Lys Phe Pro Val Gly Asn Gly Ser Glu Glu Lys Ser Leu Thr Asp Leu
945                 950                 955                 960

Arg Lys Val Leu Gly Thr Glu Asp Val Gly Cys Val Tyr Tyr Arg Leu
                965                 970                 975

Ile Gln Ala Glu Ile Ala His His Met Val Glu Asp Phe Asp Glu Ser
            980                 985                 990

Leu Leu Pro Gly Asp Ala Tyr Glu Met Ile Cys Lys Gly Phe Phe Lys
        995                 1000                1005

Asp Leu Glu Leu Arg Ser Lys Tyr Phe Tyr Leu Asp Ser Leu Asp
    1010                1015                1020

Ser Cys Pro Ile Thr Cys Ile Thr Gln Ala Val Ser Thr Arg Thr
    1025                1030                1035

Phe Asn Asp Gln Gln Phe Gln Cys Phe Lys Ser Leu Leu Leu
    1040                1045                1050

Gln Met Asn Ala Gly Lys Leu Ala Gly Lys Tyr Ser His Tyr Lys
    1055                1060                1065

Asn Lys Cys Leu Asn Phe Lys Ile Asp Arg Glu Arg Leu Met Asn
    1070                1075                1080

Asp Val Arg Ile Ser Glu Arg Glu Ser Asn Ser Glu Ala Leu Gly
    1085                1090                1095

Lys Ala Leu Ser Leu Thr Asn Cys Thr Thr Ala Val Leu Lys Asn
    1100                1105                1110

Leu Cys Phe Tyr Ser Gln Glu Ser Pro Gln Ser Tyr Thr Ser Leu
    1115                1120                1125

Gly Pro Asp Thr Gly Arg Leu Lys Phe Ser Leu Ser Tyr Lys Glu
    1130                1135                1140

Gln Val Gly Gly Asn Arg Glu Leu Tyr Ile Gly Asp Leu Arg Thr
    1145                1150                1155

Lys Met Phe Thr Arg Leu Ile Glu Asp Tyr Phe Glu Ala Leu Thr
    1160                1165                1170

Lys Gln Tyr Arg Gly Ser Cys Leu Asn Asn Glu Lys Glu Phe His
    1175                1180                1185

Asn Ala Ile Leu Ala Met Lys Leu Asn Val Ser Leu Gly Gln Val
    1190                1195                1200

Ser Tyr Ser Leu Asp His Ser Lys Trp Gly Pro Met Met Ser Pro
    1205                1210                1215

Phe Leu Phe Leu Val Phe Leu Gln Asn Leu Arg Trp Glu Thr Gly
    1220                1225                1230

Asp Asp Ile Glu Asp Ile Lys Ser Lys Asp Tyr Val Ser Thr Leu
    1235                1240                1245

Leu Ser Trp His Ile His Lys Leu Ile Glu Val Pro Phe Asn Val
    1250                1255                1260

Val Asn Ala Met Met Arg Ser Tyr Leu Lys Ser Arg Leu Gly Leu
    1265                1270                1275

Lys Lys Ser Leu His Gln Thr Ser Thr Glu Ala Phe Phe Phe Glu
    1280                1285                1290

Tyr Phe Lys Gln Asn Arg Ile Pro Ser His Leu Ser Ser Ile Ile
    1295                1300                1305

Asp Met Gly Gln Gly Ile Leu His Asn Ala Ser Asp Phe Tyr Gly
    1310                1315                1320

Leu Val Ser Glu Arg Phe Ile Asn Tyr Cys Ile Lys Cys Leu Phe
    1325                1330                1335

Glu Asp Glu Val Asp Ser Tyr Thr Ser Ser Asp Asp Gln Ile Ser
```

```
              1340                1345                1350

Leu Phe Gly Lys Asp Leu Ser Asp Leu Leu Ser Asn Glu Pro Glu
    1355                1360                1365

Glu Phe Gln Ala Ile Leu Glu Phe His Tyr Phe Leu Ser Asp Gln
    1370                1375                1380

Leu Asn Lys Phe Ile Ser Pro Lys Ser Val Ile Gly Ser Phe Val
    1385                1390                1395

Ala Glu Phe Lys Ser Arg Phe Tyr Val Trp Gly Asp Glu Val Pro
    1400                1405                1410

Leu Leu Thr Lys Phe Val Ala Ala Leu His Asn Val Lys Cys
    1415                1420                1425

Lys Glu Pro His Gln Leu Ala Glu Thr Ile Asp Thr Ile Ile Asp
    1430                1435                1440

Gln Ser Val Ala Asn Gly Val Pro Val Thr Leu Cys Asn Ala Ile
    1445                1450                1455

Gln Glu Arg Thr Leu Asn Leu Leu Arg Tyr Ala Gln Tyr Pro Ile
    1460                1465                1470

Asp Pro Phe Leu Leu Phe Leu Asp Ser Asp Val Lys Asp Trp Val
    1475                1480                1485

Asp Gly Asn Arg Gly Tyr Arg Ile Met Arg Asn Ile Glu Ala Ile
    1490                1495                1500

Leu Pro Glu Ser Thr Gln Lys Val Arg Lys Val Leu Arg Thr Val
    1505                1510                1515

Phe Asn Lys Leu Lys Leu Gly Glu Leu His Glu Phe Thr Ala
    1520                1525                1530

Ile Tyr Leu Ser Gly Asp Pro Ala Asp Ser Phe Lys Lys Leu Thr
    1535                1540                1545

Ser Leu Val Gly Asp Asp Thr Leu Ser Glu Glu Asp Leu Ser Val
    1550                1555                1560

Cys Trp Leu Asn Leu Thr Thr His His Pro Leu Lys Met Val Met
    1565                1570                1575

Arg Gln Lys Val Ile Tyr Thr Gly Ala Val Glu Leu Gly Glu Glu
    1580                1585                1590

Lys Leu Pro Thr Leu Val Lys Thr Leu Gln Ser Lys Leu Ser Ser
    1595                1600                1605

Asn Phe Thr Arg Gly Ala Gln Lys Leu Leu Cys Glu Ala Val Asn
    1610                1615                1620

Lys Ser Ala Phe Gln Ser Gly Ile Ala Ser Gly Phe Ile Gly Leu
    1625                1630                1635

Cys Lys Thr Leu Gly Ser Lys Cys Val Arg Phe Ser Asp Arg Ser
    1640                1645                1650

Thr Ala Tyr Ile Lys Ser Leu Val Ser Arg Leu Ser Ala Leu Asp
    1655                1660                1665

Ser Val Ser Ser Leu Lys Val Lys Gly Val Asp Leu Trp Ile Leu
    1670                1675                1680

Gly Lys Glu His Thr Lys Ala Ala Glu Glu Ala Leu Gly Phe Leu
    1685                1690                1695

Arg Pro Val Leu Trp Asp Tyr Phe Cys Ile Ala Leu Ser Thr Ser
    1700                1705                1710

Leu Glu Leu Gly Ser Trp Val Leu Gly Glu Pro Lys Val Lys Glu
    1715                1720                1725

Lys Thr Ser Ser Ile Pro Phe Lys Pro Cys Asp Tyr Phe Pro Met
    1730                1735                1740
```

```
Lys Pro Thr Thr Thr Lys Leu Leu Glu Asp Lys Val Gly Phe Asn
    1745                1750                1755

His Ile Ile His Ser Phe Arg Arg Leu Tyr Pro Ser Leu Phe Glu
    1760                1765                1770

Arg His Leu Leu Pro Phe Met Ser Asp Leu Ala Ser Thr Lys Met
    1775                1780                1785

Arg Trp Thr Pro Arg Ile Lys Phe Leu Asp Leu Cys Val Val Leu
    1790                1795                1800

Asp Val Asn Cys Glu Ala Met Ser Leu Ile Ser His Val Val Lys
    1805                1810                1815

Trp Lys Arg Glu Glu His Tyr Val Val Leu Ser Ser Asp Leu Ala
    1820                1825                1830

Ile Ala His Glu Arg Ser His Leu Pro Ile Thr Asp Glu Arg Val
    1835                1840                1845

Val Thr Thr Tyr Asp Val Val Gln Asn Phe Leu Arg Gln Ile Tyr
    1850                1855                1860

Phe Glu Ser Phe Ile Arg Pro Phe Val Ala Thr Ser Arg Thr Leu
    1865                1870                1875

Gly Ser Phe Thr Trp Phe Pro His Arg Ser Ser Ile Pro Glu Ser
    1880                1885                1890

Glu Gly Leu Asp Asn Leu Gly Pro Phe Ser Ser Phe Ile Glu Lys
    1895                1900                1905

Val Ile Tyr Lys Gly Val Glu Arg Pro Met Tyr Arg His Asp Leu
    1910                1915                1920

Tyr Ser Gly Tyr Ala Trp Leu Asp Phe Glu Cys Ala Pro Ala Ile
    1925                1930                1935

Leu Asn Leu Gly Gln Leu Ile Ala Ser Gly Leu Thr Glu Gln His
    1940                1945                1950

Val Phe Glu Ser Val Ser Glu Leu Leu Glu Ala Phe Ala Asp Leu
    1955                1960                1965

Ser Val Gly Ser Val Gln Ile Ser Val Thr Val Asn Phe Gln Val
    1970                1975                1980

Arg Ser Gln Gly Glu Ser Leu Lys Glu Lys Phe Ser Leu His Leu
    1985                1990                1995

Leu Phe Lys Gly Val Val Leu Glu Gly Gly Leu Phe Lys Pro His
    2000                2005                2010

Ser Leu Asp Val Thr Tyr Ser Gly Ser Val Gln Arg Ser Ala Ile
    2015                2020                2025

Lys Asp Cys Trp Arg Val Ala Gln Thr Ser Thr Trp Phe Lys Arg
    2030                2035                2040

Glu Thr Thr Ser Ile Trp Leu Leu Ser Thr Glu Asn Ile Cys Asp
    2045                2050                2055

Tyr Leu Arg Asp Ser Ser Pro Ile Pro Asp Val Ile Pro Leu Ser
    2060                2065                2070

Val Leu Leu Asn Glu Glu Ile Leu Asp Leu Glu Glu His Asp Phe
    2075                2080                2085

Thr His Ile Gly Pro Glu His Val Glu Ile Pro Leu Val Val Asp
    2090                2095                2100

Ser Gly Tyr Leu Ile Glu Gly Thr Arg Lys Leu Leu Pro Phe Asn
    2105                2110                2115

Pro Asn Ile His Asp Gln Asp Leu Asn Val Phe Ile Gly Glu Leu
    2120                2125                2130
```

```
Met Glu Asp His Ser Glu Ile Leu Glu Arg Ser Leu Ser Lys Met
    2135                2140                2145

Leu Arg Ser Arg Met Asp Gln Gly Leu His Trp Leu Gln Leu Asp
    2150                2155                2160

Ile Ile Gly Val Val Gly Arg Cys Met Pro Gly Tyr Glu Asn
    2165                2170                2175

Phe Leu Thr Arg Val Phe Ser Gly Ile Asp Phe Trp Ala Asp Phe
    2180                2185                2190

Lys Gly Tyr Ser Leu Cys Tyr Ser Arg Ser Gln Ala Ser Leu Met
    2195                2200                2205

Ile Gln Ser Ser Glu Gly Lys Phe Arg Leu Arg Gly Arg Leu Cys
    2210                2215                2220

Arg Pro Leu Phe Glu Glu Val Gly Pro Pro Leu Asp Ile Glu
    2225                2230                2235

<210> SEQ ID NO 7
<211> LENGTH: 15
<212> TYPE: PRT
<213> ORGANISM: Mopeia mammarenavirus

<400> SEQUENCE: 7

Pro Asn Ala Lys Thr Trp Ile Asp Ile Glu Gly Arg Pro Glu Asp
1               5                   10                  15

<210> SEQ ID NO 8
<211> LENGTH: 7
<212> TYPE: PRT
<213> ORGANISM: Mopeia mammarenavirus

<400> SEQUENCE: 8

Asp Glu Gly His Asp His Asp
1               5

<210> SEQ ID NO 9
<211> LENGTH: 7
<212> TYPE: PRT
<213> ORGANISM: Mopeia mammarenavirus

<400> SEQUENCE: 9

Ala Glu Ala His Asp His Asp
1               5

<210> SEQ ID NO 10
<211> LENGTH: 7
<212> TYPE: PRT
<213> ORGANISM: Mopeia mammarenavirus

<400> SEQUENCE: 10

Ala Ala Ala His Asp His Asp
1               5

<210> SEQ ID NO 11
<211> LENGTH: 7
<212> TYPE: PRT
<213> ORGANISM: Mopeia mammarenavirus

<400> SEQUENCE: 11

Ala Ala Ala Ala Asp His Asp
1               5

<210> SEQ ID NO 12
<211> LENGTH: 7
```

```
<212> TYPE: PRT
<213> ORGANISM: Mopeia mammarenavirus

<400> SEQUENCE: 12

Ala Ala Ala Ala Ala His Asp
1               5

<210> SEQ ID NO 13
<211> LENGTH: 7
<212> TYPE: PRT
<213> ORGANISM: Mopeia mammarenavirus

<400> SEQUENCE: 13

Ala Ala Ala Ala Ala Ala Asp
1               5

<210> SEQ ID NO 14
<211> LENGTH: 7
<212> TYPE: PRT
<213> ORGANISM: Mopeia mammarenavirus

<400> SEQUENCE: 14

Ala Ala Ala Ala Ala His Ala
1               5

<210> SEQ ID NO 15
<211> LENGTH: 7
<212> TYPE: PRT
<213> ORGANISM: Mopeia mammarenavirus

<400> SEQUENCE: 15

Ala Ala Ala Ala Ala Ala Ala
1               5

<210> SEQ ID NO 16
<211> LENGTH: 491
<212> TYPE: PRT
<213> ORGANISM: Lassa mammarenavirus

<400> SEQUENCE: 16

Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
                20                  25                  30

Lys Gly Leu Tyr Asn Phe Ala Thr Cys Gly Leu Val Gly Leu Val Thr
            35                  40                  45

Phe Leu Leu Leu Cys Gly Arg Ser Cys Thr Thr Ser Leu Tyr Lys Gly
        50                  55                  60

Val Tyr Glu Leu Gln Thr Leu Glu Leu Asn Met Glu Thr Leu Asn Met
65                  70                  75                  80

Thr Met Pro Leu Ser Cys Thr Lys Asn Asn Ser His His Tyr Ile Met
                85                  90                  95

Val Gly Asn Glu Thr Gly Leu Glu Leu Thr Leu Thr Asn Thr Ser Ile
                100                 105                 110

Ile Asn His Lys Phe Cys Asn Leu Ser Asp Ala His Lys Lys Asn Leu
            115                 120                 125

Tyr Asp His Ala Leu Met Ser Ile Ile Ser Thr Phe His Leu Ser Ile
        130                 135                 140

Pro Asn Phe Asn Gln Tyr Glu Ala Met Ser Cys Asp Phe Asn Gly Gly
145                 150                 155                 160
```

```
Lys Ile Ser Val Gln Tyr Asn Leu Ser His Ser Tyr Ala Gly Asp Ala
                165                 170                 175

Ala Asn His Cys Gly Thr Val Ala Asn Gly Val Leu Gln Thr Phe Met
            180                 185                 190

Arg Met Ala Trp Gly Ser Tyr Ile Ala Leu Asp Ser Gly Arg Gly
        195                 200                 205

Asn Trp Asp Cys Ile Met Thr Ser Tyr Gln Tyr Leu Ile Ile Gln Asn
    210                 215                 220

Thr Thr Trp Glu Asp His Cys Gln Phe Ser Arg Pro Ser Pro Ile Gly
225                 230                 235                 240

Tyr Leu Gly Leu Leu Ser Gln Arg Thr Arg Asp Ile Tyr Ile Ser Arg
                245                 250                 255

Arg Leu Leu Gly Thr Phe Thr Trp Thr Leu Ser Asp Ser Glu Gly Lys
            260                 265                 270

Asp Thr Pro Gly Gly Tyr Cys Leu Thr Arg Trp Met Leu Ile Glu Ala
        275                 280                 285

Glu Leu Lys Cys Phe Gly Asn Thr Ala Val Ala Lys Cys Asn Glu Lys
    290                 295                 300

His Asp Glu Glu Phe Cys Asp Met Leu Arg Leu Phe Asp Phe Asn Lys
305                 310                 315                 320

Gln Ala Ile Gln Arg Leu Lys Ala Glu Ala Gln Met Ser Ile Gln Leu
                325                 330                 335

Ile Asn Lys Ala Val Asn Ala Leu Ile Asn Asp Gln Leu Ile Met Lys
            340                 345                 350

Asn His Leu Arg Asp Ile Met Gly Ile Pro Tyr Cys Asn Tyr Ser Lys
        355                 360                 365

Tyr Trp Tyr Leu Asn His Thr Thr Thr Gly Arg Thr Ser Leu Pro Lys
    370                 375                 380

Cys Trp Leu Val Ser Asn Gly Ser Tyr Leu Asn Glu Thr His Phe Ser
385                 390                 395                 400

Asp Asp Ile Glu Gln Gln Ala Asp Asn Met Ile Thr Glu Met Leu Gln
                405                 410                 415

Lys Glu Tyr Met Glu Arg Gln Gly Lys Thr Pro Leu Gly Leu Val Asp
            420                 425                 430

Leu Phe Val Phe Ser Thr Ser Phe Tyr Leu Ile Ser Ile Phe Leu His
        435                 440                 445

Leu Val Lys Ile Pro Thr His Arg His Ile Val Gly Lys Ser Cys Pro
    450                 455                 460

Lys Pro His Arg Leu Asn His Met Gly Ile Cys Ser Cys Gly Leu Tyr
465                 470                 475                 480

Lys Gln Pro Gly Val Pro Val Lys Trp Lys Arg
                485                 490

<210> SEQ ID NO 17
<211> LENGTH: 454
<212> TYPE: PRT
<213> ORGANISM: Lujo mammarenavirus

<400> SEQUENCE: 17

Met Gly Gln Ile Val Ala Val Phe Gln Ala Ile Pro Glu Ile Leu Asn
1               5                   10                  15

Glu Ala Ile Asn Ile Val Ile Val Ile Ile Met Phe Thr Leu Ile
                20                  25                  30

Lys Gly Val Phe Asn Leu Tyr Lys Ser Gly Leu Phe Gln Leu Val Ile
            35                  40                  45
```

```
Phe Leu Leu Leu Cys Gly Lys Arg Cys Asp Ser Ser Leu Leu Ser Gly
     50                  55                  60

Phe Asn Leu Glu Thr Val His Phe Asn Met Ser Leu Leu Ser Ser Ile
 65                  70                  75                  80

Pro Met Val Ser Glu Gln Gln His Cys Ile Gln His Asn His Ser Ser
                 85                  90                  95

Ile Thr Phe Ser Leu Leu Thr Asn Lys Ser Asp Leu Glu Lys Cys Asn
                100                 105                 110

Phe Thr Arg Leu Gln Ala Val Asp Arg Val Ile Phe Asp Leu Phe Arg
             115                 120                 125

Glu Phe His His Arg Val Gly Asp Phe Pro Val Thr Ser Asp Leu Lys
 130                 135                 140

Cys Ser His Asn Thr Ser Tyr Arg Val Ile Glu Tyr Glu Val Thr Lys
145                 150                 155                 160

Glu Ser Leu Pro Arg Leu Gln Glu Ala Val Ser Thr Leu Phe Pro Asp
                 165                 170                 175

Leu His Leu Ser Glu Asp Arg Phe Leu Gln Ile Gln Ala His Asp Asp
             180                 185                 190

Lys Asn Cys Thr Gly Leu His Pro Leu Asn Tyr Leu Arg Leu Leu Lys
         195                 200                 205

Glu Asn Ser Glu Thr His Tyr Lys Val Arg Lys Leu Met Lys Leu Phe
 210                 215                 220

Gln Trp Ser Leu Ser Asp Glu Thr Gly Ser Pro Leu Pro Gly Gly His
225                 230                 235                 240

Cys Leu Glu Arg Trp Leu Ile Phe Ala Ser Asp Ile Lys Cys Phe Asp
                 245                 250                 255

Asn Ala Ala Ile Ala Lys Cys Asn Lys Glu His Asp Glu Glu Phe Cys
             260                 265                 270

Asp Met Leu Arg Leu Phe Asp Tyr Asn Lys Ala Ser Ile Ala Lys Leu
         275                 280                 285

Arg Gly Glu Ala Ser Ser Ile Asn Leu Leu Ser Gly Arg Ile Asn
 290                 295                 300

Ala Ile Ile Ser Asp Thr Leu Met Arg Ser Ser Leu Lys Arg Leu
305                 310                 315                 320

Met Gly Ile Pro Tyr Cys Asn Tyr Thr Lys Phe Trp Tyr Leu Asn His
                 325                 330                 335

Thr Lys Leu Gly Ile His Ser Leu Pro Arg Cys Trp Leu Val Ser Asn
             340                 345                 350

Gly Ser Tyr Leu Asn Glu Thr Lys Phe Thr His Asp Met Glu Asp Glu
         355                 360                 365

Ala Asp Lys Leu Leu Thr Glu Met Leu Lys Lys Glu Tyr Val Arg Arg
370                 375                 380

Gln Glu Lys Thr Pro Ile Thr Leu Met Asp Ile Leu Met Phe Ser Val
385                 390                 395                 400

Ser Phe Tyr Met Phe Ser Val Thr Leu Cys Ile Cys Asn Ile Pro Thr
                 405                 410                 415

His Arg His Ile Thr Gly Leu Pro Cys Pro Lys Pro His Arg Leu Arg
             420                 425                 430

Lys Asn Gly Thr Cys Ala Cys Gly Phe Phe Lys Ser Ile Asn Arg Ser
         435                 440                 445

Thr Gly Trp Ala Lys His
     450
```

<210> SEQ ID NO 18
<211> LENGTH: 496
<212> TYPE: PRT
<213> ORGANISM: Machupo mammarenavirus

<400> SEQUENCE: 18

```
Met Gly Gln Leu Ile Ser Phe Phe Gln Glu Ile Pro Val Phe Leu Gln
1               5                   10                  15

Glu Ala Leu Asn Ile Ala Leu Val Ala Val Ser Leu Ile Ala Val Ile
            20                  25                  30

Lys Gly Ile Ile Asn Leu Tyr Lys Ser Gly Leu Phe Gln Phe Ile Phe
        35                  40                  45

Phe Leu Leu Leu Ala Gly Arg Ser Cys Ser Asp Gly Thr Phe Lys Ile
50                  55                  60

Gly Leu His Thr Glu Phe Gln Ser Val Thr Leu Thr Met Gln Arg Leu
65                  70                  75                  80

Leu Ala Asn His Ser Asn Glu Leu Pro Ser Leu Cys Met Leu Asn Asn
                85                  90                  95

Ser Phe Tyr Tyr Met Arg Gly Val Asn Thr Phe Leu Ile Arg Val
            100                 105                 110

Ser Asp Ile Ser Val Leu Met Lys Glu Tyr Asp Val Ser Ile Tyr Glu
            115                 120                 125

Pro Glu Asp Leu Gly Asn Cys Leu Asn Lys Ser Asp Ser Ser Trp Ala
130                 135                 140

Ile His Trp Phe Ser Asn Ala Leu Gly His Asp Trp Leu Met Asp Pro
145                 150                 155                 160

Pro Met Leu Cys Arg Asn Lys Thr Lys Lys Glu Gly Ser Asn Ile Gln
                165                 170                 175

Phe Asn Ile Ser Lys Ala Asp Asp Ala Arg Val Tyr Gly Lys Lys Ile
            180                 185                 190

Arg Asn Gly Met Arg His Leu Phe Arg Gly Phe His Asp Pro Cys Glu
        195                 200                 205

Glu Gly Lys Val Cys Tyr Leu Thr Ile Asn Gln Cys Gly Asp Pro Ser
210                 215                 220

Ser Phe Asp Tyr Cys Gly Val Asn His Leu Ser Lys Cys Gln Phe Asp
225                 230                 235                 240

His Val Asn Thr Leu His Phe Leu Val Arg Ser Lys Thr His Leu Asn
                245                 250                 255

Phe Glu Arg Ser Leu Lys Ala Phe Phe Ser Trp Ser Leu Thr Asp Ser
            260                 265                 270

Ser Gly Lys Asp Met Pro Gly Gly Tyr Cys Leu Glu Glu Trp Met Leu
        275                 280                 285

Ile Ala Ala Lys Met Lys Cys Phe Gly Asn Thr Ala Val Ala Lys Cys
290                 295                 300

Asn Gln Asn His Asp Ser Glu Phe Cys Asp Met Leu Arg Leu Phe Asp
305                 310                 315                 320

Tyr Asn Lys Asn Ala Ile Lys Thr Leu Asn Asp Glu Ser Lys Lys Glu
                325                 330                 335

Ile Asn Leu Leu Ser Gln Thr Val Asn Ala Leu Ile Ser Asp Asn Leu
            340                 345                 350

Leu Met Lys Asn Lys Ile Lys Glu Leu Met Ser Ile Pro Tyr Cys Asn
        355                 360                 365

Tyr Thr Lys Phe Trp Tyr Val Asn His Thr Leu Thr Gly Gln His Thr
370                 375                 380
```

```
Leu Pro Arg Cys Trp Leu Ile Arg Asn Gly Ser Tyr Leu Asn Thr Ser
385                 390                 395                 400

Glu Phe Arg Asn Asp Trp Ile Leu Glu Ser Asp His Leu Ile Ser Glu
                405                 410                 415

Met Leu Ser Lys Glu Tyr Ala Glu Arg Gln Gly Lys Thr Pro Ile Thr
            420                 425                 430

Leu Val Asp Ile Cys Phe Trp Ser Thr Ile Phe Phe Thr Ala Ser Leu
        435                 440                 445

Phe Leu His Leu Val Gly Ile Pro Thr His Arg His Leu Lys Gly Glu
    450                 455                 460

Ala Cys Pro Leu Pro His Lys Leu Asp Ser Phe Gly Gly Cys Arg Cys
465                 470                 475                 480

Gly Lys Tyr Pro Arg Leu Lys Lys Pro Thr Ile Trp His Lys Arg His
                485                 490                 495

<210> SEQ ID NO 19
<211> LENGTH: 479
<212> TYPE: PRT
<213> ORGANISM: Guanarito mammarenavirus

<400> SEQUENCE: 19

Met Gly Gln Leu Ile Ser Phe Phe Gln Asp Ile Pro Ile Phe Phe Glu
1               5                   10                  15

Glu Ala Leu Asn Val Ala Leu Ala Val Val Thr Leu Leu Ala Ile Ile
            20                  25                  30

Lys Gly Ile Val Asn Val Trp Lys Ser Gly Ile Leu Gln Leu Phe Val
        35                  40                  45

Phe Leu Val Leu Ala Gly Arg Ser Cys Ser Phe Lys Val Gly His His
    50                  55                  60

Thr Asn Phe Glu Ser Phe Thr Val Lys Leu Gly Gly Val Phe His Glu
65                  70                  75                  80

Leu Pro Ser Leu Cys Arg Val Asn Asn Ser Tyr Ser Leu Ile Arg Leu
                85                  90                  95

Ser His Asn Ser Asn Gln Ala Leu Ser Val Glu Tyr Val Asp Val His
            100                 105                 110

Pro Val Leu Cys Ser Ser Ser Pro Thr Ile Leu Asp Asn Tyr Thr Gln
        115                 120                 125

Cys Ile Lys Gly Ser Pro Glu Phe Asp Trp Ile Leu Gly Trp Thr Ile
    130                 135                 140

Lys Gly Leu Gly His Asp Phe Leu Arg Asp Pro Arg Ile Cys Cys Glu
145                 150                 155                 160

Pro Lys Lys Thr Thr Asn Ala Glu Phe Thr Phe Gln Leu Asn Leu Thr
                165                 170                 175

Asp Ser Pro Glu Thr His His Tyr Arg Ser Lys Ile Glu Val Gly Ile
            180                 185                 190

Arg His Leu Phe Gly Asn Tyr Ile Thr Asn Asp Ser Tyr Ser Lys Met
        195                 200                 205

Ser Val Val Met Arg Asn Thr Thr Trp Glu Gly Gln Cys Ser Asn Ser
    210                 215                 220

His Val Asn Thr Leu Arg Phe Leu Val Lys Asn Ala Gly Tyr Leu Val
225                 230                 235                 240

Gly Arg Lys Pro Leu Ala Phe Phe Ser Trp Ser Leu Ser Asp Pro Lys
                245                 250                 255

Gly Asn Asp Met Pro Gly Gly Tyr Cys Leu Glu Arg Trp Met Leu Val
```

```
                260             265             270
Ala Gly Asp Leu Lys Cys Phe Gly Asn Thr Ala Val Ala Lys Cys Asn
            275                 280                 285

Leu Asn His Asp Ser Glu Phe Cys Asp Met Leu Arg Leu Phe Asp Phe
        290                 295                 300

Asn Lys Asn Ala Ile Glu Lys Leu Asn Asn Gln Thr Lys Thr Ala Val
305                 310                 315                 320

Asn Met Leu Thr His Ser Ile Asn Ser Leu Ile Ser Asp Asn Leu Leu
                325                 330                 335

Met Arg Asn Lys Leu Lys Glu Ile Leu Lys Val Pro Tyr Cys Asn Tyr
            340                 345                 350

Thr Arg Phe Trp Tyr Ile Asn His Thr Lys Ser Gly Glu His Ser Leu
        355                 360                 365

Pro Arg Cys Trp Leu Val Ser Asn Gly Ser Tyr Leu Asn Glu Ser Asp
        370                 375                 380

Phe Arg Asn Glu Trp Ile Leu Glu Ser Asp His Leu Ile Ala Glu Met
385                 390                 395                 400

Leu Ser Lys Glu Tyr Gln Asp Arg Gln Gly Lys Thr Pro Leu Thr Leu
                405                 410                 415

Val Asp Leu Cys Phe Trp Ser Ala Ile Phe Phe Thr Thr Ser Leu Phe
            420                 425                 430

Leu His Leu Val Gly Phe Pro Thr His Arg His Ile Gln Gly Asp Pro
        435                 440                 445

Cys Pro Leu Pro His Arg Leu Asp Arg Asn Gly Ala Cys Arg Cys Gly
        450                 455                 460

Arg Phe Gln Lys Leu Gly Lys Gln Val Thr Trp Lys Arg Lys His
465                 470                 475

<210> SEQ ID NO 20
<211> LENGTH: 484
<212> TYPE: PRT
<213> ORGANISM: Chapare mammarenavirus

<400> SEQUENCE: 20

Met Gly Gln Leu Val Ser Phe Phe Gln Glu Ile Pro Asn Ile Ile Gln
1               5                   10                  15

Glu Ala Ile Asn Ile Ala Leu Ile Ala Val Ser Leu Ile Ala Ile Leu
            20                  25                  30

Lys Gly Leu Val Asn Leu Trp Lys Ser Gly Leu Phe Gln Leu Leu Val
        35                  40                  45

Phe Leu Ile Leu Ala Gly Arg Ser Cys Ser Phe Lys Ile Gly Arg Ser
    50                  55                  60

Thr Glu Leu Gln Asn Ile Thr Ile Asn Met Leu Lys Val Phe Glu Asp
65                  70                  75                  80

His Pro Ile Ser Cys Thr Val Asn Lys Thr Leu Tyr Tyr Ile Arg Glu
                85                  90                  95

Ser Glu Asn Ala Thr Trp Cys Val Glu Ile Ala Ala Leu Asp Met Ser
            100                 105                 110

Val Leu Leu Ser Pro His Asp Pro Arg Val Met Gly Asn Leu Ser Asn
        115                 120                 125

Cys Val His Pro Asp Ile Lys His Arg Ser Glu Leu Leu Gly Leu Leu
    130                 135                 140

Glu Trp Ile Leu Arg Ala Leu Lys Tyr Asp Phe Leu Asn Tyr Pro Pro
145                 150                 155                 160
```

```
Leu Leu Cys Glu Lys Val Thr Ser Ser Val Asn Glu Thr Arg Ile Gln
            165                 170                 175

Ile Asn Val Ser Asp Ser Ala Gly Ser His Asp Phe Lys Glu Thr Met
        180                 185                 190

Leu Gln Arg Leu Ala Ile Leu Phe Gly Thr Lys Leu Met Phe Asp Lys
        195                 200                 205

Thr Pro Lys Gln Phe Ile Val Ile Arg Asn Gln Thr Trp Val Asn Gln
    210                 215                 220

Cys Lys Ser Asn His Val Asn Thr Leu His Leu Met Met Ala Asn Ala
225                 230                 235                 240

Gly His Ala Val Lys Leu Arg Arg Leu Gln Gly Val Phe Thr Trp Thr
            245                 250                 255

Ile Thr Asp Ala Ala Gly Asn Asp Met Pro Gly Gly Tyr Cys Leu Glu
        260                 265                 270

Arg Trp Met Leu Val Thr Ser Asp Leu Lys Cys Phe Gly Asn Thr Ala
        275                 280                 285

Leu Ala Lys Cys Asn Leu Asn His Asp Ser Glu Phe Cys Asp Met Leu
    290                 295                 300

Lys Leu Phe Glu Phe Asn Lys Lys Ala Ile Glu Ser Leu Asn Asp Asn
305                 310                 315                 320

Thr Lys Asn Lys Val Asn Leu Leu Thr His Ser Ile Asn Ala Leu Ile
            325                 330                 335

Ser Asp Asn Leu Leu Met Lys Asn Arg Leu Lys Glu Leu Leu Asp Thr
        340                 345                 350

Pro Tyr Cys Asn Tyr Thr Lys Phe Trp Tyr Val Asn His Thr Ile Thr
        355                 360                 365

Gly Glu His Ser Leu Pro Arg Cys Trp Met Val Lys Asn Asn Ser Tyr
    370                 375                 380

Leu Asn Glu Ser Glu Phe Arg Asn Asp Trp Ile Leu Glu Ser Asp His
385                 390                 395                 400

Leu Leu Ser Glu Met Leu Asn Lys Glu Tyr Phe Asp Arg Gln Gly Lys
            405                 410                 415

Thr Pro Ile Thr Leu Val Asp Ile Cys Phe Trp Ser Thr Leu Phe Phe
        420                 425                 430

Thr Thr Thr Leu Phe Leu His Leu Val Gly Phe Pro Thr His Arg His
        435                 440                 445

Ile Gln Gly Glu Pro Cys Pro Leu Pro His Lys Leu Asn Ser Asn Gly
    450                 455                 460

Gly Cys Arg Cys Gly Arg Tyr Pro Glu Leu Lys Lys Pro Thr Thr Trp
465                 470                 475                 480

His Arg Lys His

<210> SEQ ID NO 21
<211> LENGTH: 488
<212> TYPE: PRT
<213> ORGANISM: Sabia mammarenavirus

<400> SEQUENCE: 21

Met Gly Gln Leu Phe Ser Phe Phe Glu Glu Val Pro Asn Ile Ile His
1               5                   10                  15

Glu Ala Ile Asn Ile Ala Leu Ile Ala Val Ser Leu Ile Ala Ala Leu
            20                  25                  30

Lys Gly Met Ile Asn Leu Trp Lys Ser Gly Leu Phe Gln Leu Ile Phe
        35                  40                  45
```

Phe Leu Thr Leu Ala Gly Arg Ser Cys Ser Phe Arg Ile Gly Arg Ser
 50                  55                  60

Thr Glu Leu Gln Asn Ile Thr Phe Asp Met Leu Lys Val Phe Glu Asp
 65                  70                  75                  80

His Pro Thr Ser Cys Met Val Asn His Ser Thr Tyr Val His Glu
                 85                  90                  95

Asn Lys Asn Ala Thr Trp Cys Leu Glu Val Ser Val Thr Asp Val Thr
            100                 105                 110

Leu Leu Met Ala Glu His Asp Arg Gln Val Leu Asn Asn Leu Ser Asn
            115                 120                 125

Cys Val His Pro Ala Val Glu His Arg Ser Arg Met Val Gly Leu Leu
            130                 135                 140

Glu Trp Ile Phe Arg Ala Leu Lys Tyr Asp Phe Asn His Asp Pro Thr
145                 150                 155                 160

Pro Leu Cys Gln Lys Gln Thr Ser Thr Val Asn Glu Thr Arg Val Gln
                165                 170                 175

Ile Asn Ile Thr Glu Gly Phe Gly Ser His Gly Phe Glu Asp Thr Ile
            180                 185                 190

Leu Gln Arg Leu Gly Val Leu Phe Gly Ser Arg Ile Ala Phe Ser Asn
            195                 200                 205

Ile Gln Asp Leu Gly Lys Lys Arg Phe Leu Leu Ile Arg Asn Ser Thr
            210                 215                 220

Trp Lys Asn Gln Cys Glu Met Asn His Val Asn Ser Met His Leu Met
225                 230                 235                 240

Leu Ala Asn Ala Gly Arg Ser Ser Gly Ser Arg Arg Pro Leu Gly Ile
                245                 250                 255

Phe Ser Trp Thr Ile Thr Asp Ala Val Gly Asn Asp Met Pro Gly Gly
            260                 265                 270

Tyr Cys Leu Glu Arg Trp Met Leu Val Thr Ser Asp Leu Lys Cys Phe
            275                 280                 285

Gly Asn Thr Ala Leu Ala Lys Cys Asn Leu Asp His Asp Ser Glu Phe
            290                 295                 300

Cys Asp Met Leu Lys Leu Phe Glu Phe Asn Lys Lys Ala Ile Glu Thr
305                 310                 315                 320

Leu Asn Asp Asn Thr Lys Asn Lys Val Asn Leu Thr His Ser Ile
                325                 330                 335

Asn Ala Leu Ile Ser Asp Asn Leu Leu Met Lys Asn Arg Leu Lys Glu
            340                 345                 350

Leu Leu Asn Thr Pro Tyr Cys Asn Tyr Thr Lys Phe Trp Tyr Val Asn
            355                 360                 365

His Thr Ala Ser Gly Glu His Ser Leu Pro Arg Cys Trp Leu Val Arg
            370                 375                 380

Asn Asn Ser Tyr Leu Asn Glu Ser Glu Phe Arg Asn Asp Trp Ile Ile
385                 390                 395                 400

Glu Ser Asp His Leu Leu Ser Glu Met Leu Asn Lys Glu Tyr Ile Asp
                405                 410                 415

Arg Gln Gly Lys Thr Pro Leu Thr Leu Val Asp Ile Cys Phe Trp Ser
            420                 425                 430

Thr Leu Phe Phe Thr Thr Thr Leu Phe Leu His Leu Val Gly Phe Pro
            435                 440                 445

-continued

```
Thr His Arg His Ile Arg Gly Glu Pro Cys Pro Leu Pro His Arg Leu
    450                 455                 460

Asn Ser Arg Gly Gly Cys Arg Cys Gly Lys Tyr Pro Glu Leu Lys Lys
465                 470                 475                 480

Pro Ile Thr Trp His Lys Asn His
                485
```